(12) United States Patent
Liang et al.

(10) Patent No.: US 6,908,930 B2
(45) Date of Patent: Jun. 21, 2005

(54) 4-SUBSTITUTED 7-AZA-INDOLIN-2-ONES AND THEIR USE AS PROTEIN KINASE INHIBITORS

(75) Inventors: Congxin Liang, Sunnyvale, CA (US); Li Sun, Foster City, CA (US); Chung Chen Wei, Foster City, CA (US); Peng Cho Tang, Moraga, CA (US); Gerald McMahon, Kenwood, CA (US); Klaus Peter Hirth, San Francisco, CA (US); Jingrong Cui, Albany, CA (US)

(73) Assignee: Sugen, Inc., San Diego, CA (US)

( * ) Notice: Subject to any disclaimer, the term of this patent is extended or adjusted under 35 U.S.C. 154(b) by 0 days.

(21) Appl. No.: 10/622,787

(22) Filed: Jul. 21, 2003

(65) Prior Publication Data

US 2004/0053924 A1 Mar. 18, 2004

Related U.S. Application Data

(62) Division of application No. 09/741,737, filed on Dec. 21, 2000, now Pat. No. 6,610,688.
(60) Provisional application No. 60/171,288, filed on Dec. 21, 1999.

(51) Int. Cl.$^7$ ................... C07D 471/04; A61K 31/437

(52) U.S. Cl. ...................................... 514/300; 546/113

(58) Field of Search ........................ 514/300; 546/113

(56) References Cited

U.S. PATENT DOCUMENTS

| | | | |
|---|---|---|---|
| 5,719,135 A | 2/1998 | Buzzetti et al. | |
| 5,811,432 A | 9/1998 | Marfat et al. | |
| 5,916,891 A | 6/1999 | Adams et al. | |
| 5,955,592 A | 9/1999 | Ullrich et al. | |

FOREIGN PATENT DOCUMENTS

| | | |
|---|---|---|
| WO | WO 87/04928 A1 | 8/1987 |
| WO | WO 91/09598 A1 | 7/1991 |
| WO | WO 93/20078 A1 | 10/1993 |
| WO | WO 96/16964 A1 | 6/1996 |
| WO | WO 97/13771 A1 | 4/1997 |
| WO | WO 98/02437 A1 | 1/1998 |
| WO | WO 98/02438 A1 | 1/1998 |
| WO | WO 98/23613 A1 | 6/1998 |
| WO | WO 99/21859 A1 | 5/1999 |
| WO | WO 99/37622 A1 | 7/1999 |

OTHER PUBLICATIONS

Wolff, Manfred E. "Burger'Medicinal Chemistry, 5ed, Part I", John Wiley & Sons, 1995, pp. 975–977.*
West, Anthony R., Solid State Chemistry and its Applications, Wiley, New York, 1988, pp. 358 & 365.*
Alexander J. Bridges, Chem. Rev., 101 (8), 2541–2571, 2001.*
Cohen EE, Rosen F, Stadler WM, Recant W, Stenson K, Huo D, Vokes EE, J Clin Oncol. 2003 May 15;21(10):1980–7.*
Banker, G.S. et al, "Modern Pharmaceutics, 3ed.", Marcel Dekker, New York, 1996, p. 596.*
Akbasak et al., "Oncogenes: cause or consequence in the development of glial tumors," *Journal of the Neurological Sciences*, 1992, pp. 119–133, vol. 111, Elsevier Science Publishers B.V.
Arteaga et al., "Blockade of the Type I Somatomedin Receptor Inhibits Growth of Human Breast Cancer Cells in Athymic Mice," *Journal of Clinical Investigation*, Nov. 1989, pp. 1418–1423, vol. 84, The American Society for Clinical Investigation, Inc.
Baserga, "Oncogenes and the Strategy of Growth Factors," *Cell Minireview*, Dec. 19, 1994, pp. 927–930, vol. 79, Cell Press.
Baserga, "The Insulin–like Growth Factor I Receptor: A Key to Tumor Growth?" *Cancer Research*, Jan. 15, 1995, pp. 249–252, vol. 55.
Bolen et al., "The Src family of tyrosine protein kinases in hemopoietic signal transduction," *The FASEB Journal*, Dec. 1992, pp. 3403–3409, vol. 6, Bristol–Myers Squibb.
Brott et al., "MEK2 is a Kinase Related to MEK1 and is Differentially Expressed in Murine Tissues," *Cell Growth & Differentiation*, Nov. 1993, pp. 921–929, vol. 4, American Association of Cancer Research.
Campbell et al., "Evidence for Involvement of the Growth Hormone Receptor–associated Tyrosine Kinase in Actions of Growth Hormone." *The Journal of Biological Chemistry*, 1993, pp. 7427–7434, vol. 268, No. 10, The American Society for Biochemistry and Molecular Biology, Inc.

(Continued)

Primary Examiner—Thomas C. McKenzie
(74) Attorney, Agent, or Firm—Peter C. Richardson; Bryan C. Zielinski; Vincent P. Liptak

(57) ABSTRACT

This invention relates to 4-substituted 7-aza-indolin-2-ones and their use as protein kinase inhibitors. Particular 4-substituted 7-aza-indolin-2-ones disclosed herein are of Formula 1

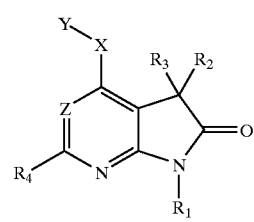

and pharmaceutically acceptable salts, solvates, clathrates, and prodrugs thereof, wherein $R_1$, $R_2$, $R_3$, $R_4$, X, Y, and Z are defined herein. The invention further relates to pharmaceutical compositions and dosage forms comprising compounds of Formula 1 and to methods of their use for the treatment and/or prevention of diseases such as, but not limited to, cancer.

12 Claims, No Drawings

OTHER PUBLICATIONS

Cance et al., "Novel Protein Kinases Expressed in Human Breast Cancer," *International Journal of Cancer*, 1993, pp. 571–577, vol. 54, Wiley–Lisa, Inc.

Cleaveland et al., "A Microtiter–Based Assay for the Detection of Protein Tyrosine Kinase Activity," *Analytical Biochemistry*, 1990, pp. 249–253, vol. 190, Academic Press, Inc.

Coppola, D. et al., "A Functional Insulin–Like Growth Factor I Receptor is Required for the Mitogenic and Transforming Activities of the Epidermal Growth Factor Receptor," *Molecular and Cellular Biology*, Jul. 1994, pp. 4588–4595, vol. 14, No. 7, American Society for Microbiology.

Damasio, "Alzheimer's disease and related dementias," *Cecil Textbook of Medicine*, 20$^{th}$ Edition, 1996, pp. 1992–1996, vol. 2.

Davis et al., Chapter 47, "Animal Cells: Cultivation, Growth Regulation, Transformation," *Microbiology* 4$^{th}$ Ed., 1990, pp. 838–841, © J. B. Lippincott Company.

Dickson et al., "Tyrosine kinase receptor—nuclear protooncogene interactions in breast cancer," *Cancer Treatment Research*, 1992, pp. 249–273, vol. 61, 1991 Kluwer Academic Publishers, Boston.

Donato et al., "Tumor Necrosis Factor Regulates Tyrosine Phosphorylation in Epidermal Growth Factor Receptors in A431 Carcinoma Cells: Evidence for a Distinct Mechanism," *Cell Growth and Differentiation*, May 1992, pp. 259–268, vol. 3.

Farley et al., "Development of Solid–Phase Enzyme–Linked Immunosorbent Assays for the Determination of Epidermal Growth Factor Receptor and pp60$^{c-src}$ Tyrosine Protein Kinase Activity," *Analytical Biochemistry*, 1992, pp. 151–157, vol. 203, Academic Press, Inc.

Floege et al., "Factors involved in the regulation of mesangial cell proliferation in vitro and in vivo," *Kidney International*, 1993, pp. S–47–S–54, vol. 43, Suppl. 39, International Society of Nephrology.

Goldring et al., "Cytokines and Cell Growth Control," *Critical Reviews in Eukaryotic Gene Expression*, 1991, pp. 301–326, vol. 1, No. 4.

Hansen et al., "Application of two–dimensional gel analysis to identification and characterization of tyrosine phosphorylated substrates for growth factor receptors," *Electrophoresis*, 1993, pp. 112–126, vol. 14, VCH Verlagsgesellschaft mbH, D–6940 Weinheim, 1993.

Katagiri et al., "Tyrosine–Phosphorylation of Tubulin during Monocytic Differentiation of HL–60 Cells," *The Journal of Immunology*, Jan. 15, 1993, pp. 585–593, vol. 150, No. 2, The American Association of Immunologists.

Korc et al., "Overexpression of the Epidermal Growth Factor Receptor in Human Pancreatic Cancer is Associated with Concomitant Increases in the Levels of Epidermal Growth Factor and Transforming Growth Factor Alpha," *Journal of Clinical Investigation*, Oct. 1992, pp. 1352–1360, vol. 90, The American Society for Clinical Investigation, Inc.

Layzer, "Degenerative diseases of the nervous system," *Cecil Textbook of Medicine*, 20$^{th}$ Edition, 1996, pp. 2050–2057, vol. 2.

Lazaro et al., "Description of an Enzyme–Linked Immunosorbent Assay for the Detection of Protein Tyrosine Kinase," *Biochemistry*, 1991, pp. 257–261, vol. 192, Academic Press, Inc.

Lee et al., "Intracellular Retention of Membrane–anchored v–sis Protein Abrogates Autocrine Signal Transdution," *The Journal of Cell Biology*, Sep. 1992, pp. 1057–1070, vol. 118, The Rockefeller University Press.

Macauley et al., "Autocrine Function for Insulin–like Growth Factor I in Human Small Cell Lung Cancer Cell Lines and Fresh Tumor Cells," *Cancer Research*, Apr. 15, 1990, pp. 2511–2517, vol. 50.

Peraldi et al., "Dephosphorylation of human insulin–like growth factor I (IGF–I) receptors by membrane–associated tyrosine phosphatases," *Biochem. J.*, 1992, pp. 71–78, vol. 285.

Plowman et al., "Receptor Tyrosine Kinases as Targets for Drug Intervention," *DN&P*, Aug. 1994, pp. 334–339, vol. 7, No. 6.

Sandbert–Nordqvist et al., "Characterization of insulin–like Growth Factor 1 in Human Primary Brain Tumors," *Cancer Research*, Jun. 1, 1993, pp. 2475–2478, vol. 53.

Schraag et al., "Standardization of an Enzyme–Linked Immunosorbent Assay for the Determination of Protein Tyrosine Kinase Activity," *Analytical Biochemistry*, 1993, pp. 233–239, vol. 211, Academic Press, Inc.

Simone, "Oncology: Introduction," *Cecil Textbook of Medicine*, 20$^{th}$ Edition, 1996, pp. 1004–1010, vol. 1.

Slamon et al., "Studies of the HER–2/neu Proto–oncogene in Human Breast and Ovarian Cancer," *Science Reports*, May 12, 1989, pp. 707–712, vol. 244, American Association for the Advancement of Science.

Torp et al., "Expression of the epidermal growth factor receptor gene in human brain metastases," *APMIS*, 1992, pp. 713–719, vol. 100, The Institute of Cancer Research.

Traxler et al., "Review: Oncologic Endocrine & Metabolic Protein Tyrosine Kinase Inhibitors in Cancer Treatment," *Exp. Opin. Ther. Patents*, 1997, pp. 571–588, vol. 7, No. 6.

Tuzi et al., "Expression of growth factor receptors in human brain tumours," *British Journal of Cancer*, 1993, pp. 227–233, vol. 63.

* cited by examiner

4-SUBSTITUTED 7-AZA-INDOLIN-2-ONES AND THEIR USE AS PROTEIN KINASE INHIBITORS

CROSS-REFERENCE TO RELATED APPLICATIONS

This application is a divisional of U.S. application Ser. No. 09/741,737, filed Dec. 21, 2000, now U.S. Pat. No. 6,610,688 and claims priority to Provisional Application Ser. No. 60/171,288, filed Dec. 21, 1999.

1. FIELD OF THE INVENTION

This invention relates to protein kinase inhibitors, pharmaceutical compositions and dosage forms comprising them, and methods of their use for the treatment and prevention of diseases such as, but not limited to, cancer.

2. BACKGROUND OF THE INVENTION

Cellular signal transduction is a mechanism whereby external stimuli that regulate cellular processes are relayed from receptors at the surface of a cell to its interior. One of the key biochemical mechanisms of signal transduction involves the reversible phosphorylation of proteins. The phosphorylation state of a protein, which can affect its conformation, enzymatic activity, and cellular location, is modified through the reciprocal actions of protein kinases ("PKs") and protein phosphatases. The regulation, or lack of regulation, of protein kinases can thus have a dramatic effect on cellular behavior.

During cellular signal transduction, the function of each receptor kinase is determined by its pattern of expression, ligand availability, and the array of downstream signal transduction pathways that are activated by it. One example of a pathway includes a cascade of Growth Factor receptor tyrosine kinases ("RTKs"), such as EGF-R, PDGF-R, VEGF-R, IGF1-R, and the Insulin receptor, that deliver signals via phosphorylation to other kinases, such as Src tyrosine kinase and Raf, Mek, and Erk serine/threosine kinases. See, e.g., Davis, B. D., et al., *Microbiology* 838–841 (4$^{th}$ ed., 1990); and Brott, B. K., et al., *Cell Growth Differ.* 4(11):921–929 (1993). Each of these kinases play related, but functionally distinct, roles. The loss of regulation of the Growth Factor signaling pathway is a frequent occurrence in disease states such as cancer.

Aberrant expression of, or mutations in, protein kinases have been shown to lead to either uncontrolled cell proliferation (for example, malignant tumour growth) or to defects in key developmental processes. Protein kinases have been implicated as targets in central nervous system disorders (such as Alzheimer's), inflammatory disorders (such as psoriasis), bone diseases (such as osteoporosis), atheroscieroses, restenosis, thrombosis, metabolic disorders (such as diabetes), and infectious diseases (such as viral and fungal infections).

Because the regulation and/or inhibition of protein kinases can aid in the treatment and/or prevention of a variety of diseases, significant research has been directed at discovering compounds that affect protein kinase activity. This research is similar to that which may have led to discovery of the compounds disclosed by PCT application WO 91/09598 and U.S. Pat. No. 5,811,432, which are of the formula

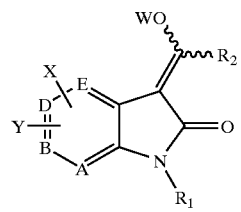

wherein one of A, B, D, and E is nitrogen and the others are carbon; X and Y can be, for example, halogen or hydroxy; $R_1$ is $(C_1-C_6)$alkyl or an amide; $R_2$ is $(C_1-C_8)$alkyl, preferably $(C_3-C_8)$alkyl; and W is, for example, hydrogen or $(CO_2-C_{10})$alkanoyl. These compounds, which are not reported to be kinase inhibitors, are allegedly inhibitors of prostaglandin $H_2$ synthase, 5-lipoxygenase, and interleukin-1 biosynthesis, and allegedly are anti-inflammatory and analgesic agents.

Examples of compounds that are allegedly protein kinase inhibitors are disclosed by PCT application WO 97/13771. These compounds are of the formula

wherein X is nitrogen or CH; $R_2$, Y, $R_3$, and $R_5$ are each selected from a large number of moieties; the group

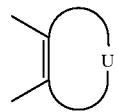

represents, for example, a 5-membered heterocyclic ring; and each $R_1$ independently represents a 5- or 6-membered heterocyclic ring.

PCT application WO 98/02437 discloses compounds similar in structure to those described above, i.e.:

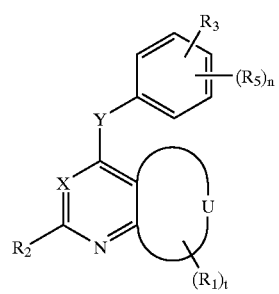

As above, $R_1$ represents a 5- or 6-membered heterocyclic ring. These compounds are also allegedly protein tyrosine kinase inhibitors.

PCT application WO 98/02438 discloses compounds of the formula:

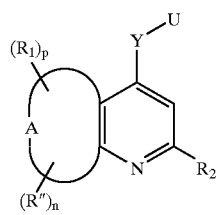

wherein X is nitrogen or CH; $R_1$, $R_2$, and Y are each selected from a large number of moieties; U is a 5- to 10-membered mono or bicyclic ring system; the group

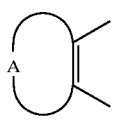

represents, for example, a 5-membered heterocyclic ring; and R" represents a phenyl group or a 5- or 6-membered heterocyclic ring. These compounds are also allegedly protein tyrosine kinase inhibitors.

PCT application WO 98/23613 discloses compounds of the formula:

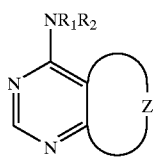

wherein Z can be a group of the formula

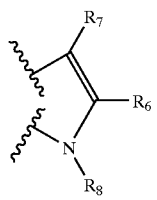

and $R_6$ is H, halogen, cyano, alkyl, or substituted alkyl. These compounds can allegedly be used in the treatment of hyperpoliferative diseases such as cancer.

PCT application WO 99/21859 discloses compounds of the formula:

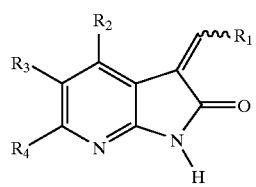

wherein the R groups are variously defined. These compounds are reportedly useful as protein kinase inhibitors.

PCT application WO 99/37622 discloses a compound of the formula:

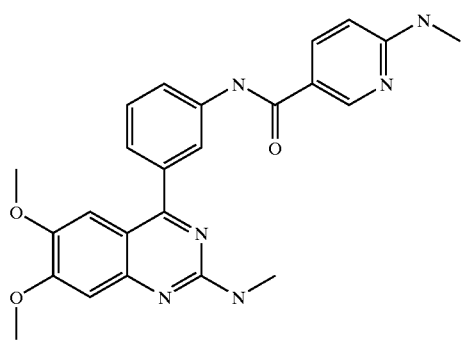

which is allegedly useful as a PDE4 and TNF-α antagonist.

U.S. Pat. No. 5,916,891 discloses a compound of the formula:

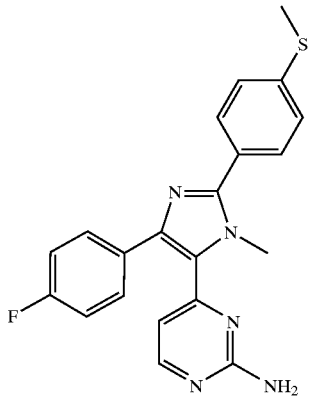

which is a derivative of the compound of formula:

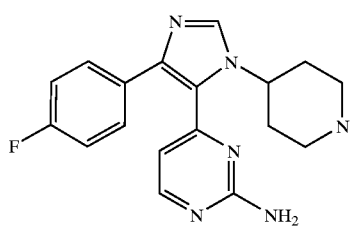

which is allegedly a p38/Raf inhibitor. Both of these compounds share structural features with rofecoxib, which is sold by Merck under the tradename Vioxx® and which has the formula:

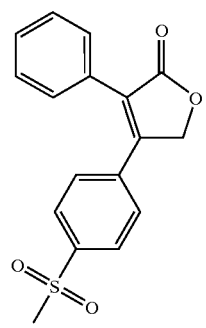

and celecoxib, which is sold by Monsanto and which has the formula:

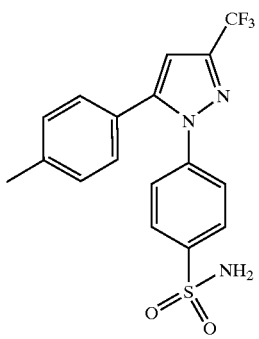

Final examples of compounds that are allegedly useful as protein kinase inhibitors are disclosed in PCT applications WO 87/04928 and WO 96/16964.

Despite the large number of compounds that reportedly inhibit protein kinase activity, a need still exists for compounds that can be used in the treatment and/or prevention of cancer and other diseases in humans. This is due, in part, to bioavailability, toxicity, and other problems which render many of the known protein kinase inhibitors unsuited for clinical development.

This invention is therefore directed in part to compounds which modulate protein kinase ("PK") signal transduction by affecting the enzymatic activity of tyrosine kinases and thereby interfering with the signals transduced by them. More particularly, the present invention is directed to compounds which modulate the RTK, cellular tyrosine kinase ("CTK") and/or serine/threonine kinase ("STK") mediated signal transduction pathways as a therapeutic approach to treat many kinds of solid tumors, including but not limited to carcinoma, sarcomas including Kaposi's sarcoma, leukemia, erythroblastoma, glioblastoma, meningioma, astrocytoma, melanoma and myoblastoma. Other specific indications related to these include, but are not limited to, brain cancers, bladder cancers, ovarian cancers, gastric cancers, pancreas cancers, colon cancers, blood cancers, lung cancers, bone cancers and leukemias.

Further examples, without limitation, of the types of disorders related to unregulated PK activity that the compounds described herein may be usefull in preventing, treating and/or studying, are cell proliferative disorders, fibrotic disorders and metabolic disorders. Cell proliferative disorders, which may be prevented, treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis. Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., *Kidney International* 43:47S–54S (1993).

As noted previously, PKs have been associated with such cell proliferative disorders. For example, some members of the RTK family have been associated with the development of cancer. Some of these receptors, like the EGFR (Tuzi et al., *Br. J. Cancer* 63:227–233 (1991); Torp et al., *APMIS* 100:713–719(1992)) HER2/neu (Slamon et al., *Science* 244:707–712 (1989)) and PDGFR (Kumabe et al., *Oncogene*, 7:627–633 (1992)) are over-expressed in many tumors and/or are persistently activated by autocrine loops. In fact, in the most common and severe cancers these receptor over-expressions have been demonstrated Akbasak and Suner-Akbasak et al., *J. Neurol. Sci.*, 111:119–133 (1992); Dickson et al., *Cancer Treatment Res.* 61:249–273 (1992); Korc et al., *J. Clin. Invest.* 90:1352–1360 (1992)) and autocrine loops (Lee and Donoghue, *J. Cell. Biol.*, 118:1057–1070 (1992); Korc et al., supra; Akbasak and Suner-Akbasak et al., supra). For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma, lung, ovarian, melanoma and prostate. The RTK c-met has been generally associated with hepatocarcinogenesis and thus hepatocellular carcinoma. C-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkins disease, Burkitts disease, and the lymphoma cell line. Flk has been associated with a broad spectrum of tumors including without limitation mammary, ovarian and lung tumors as well as gliomas such as gtioblastoma. IGF-IR, in addition to being implicated in nutritional support and in type-II diabetes, has also been associated with several types of cancers. For example, IGF-I has been implicated as an autocrine growth stimulator for several tumor types, e.g., human breast cancer carcinoma cells (Arteaga et al., *J. Clin. Invest.* 84:1418–1423 (1989)) and small lung tumor cells (Macauley et al., *Cancer Res.*, 50:2511–2517 (1990)). In addition, IGF-I, integrally involved in the normal growth and differentiation of the nervous system, appears to be an autocrine stimulator of human gliomas. Sandberg-Nordqvist et al., *Cancer Res.* 53:2475–2478 (1993). The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, *Eukaryotic Gene Expression*, 1:301–326 (1991). In a series of recent publications, Baserga even suggests that IGF-IR plays a central role in the mechanisms of transformation and, as such, could be a preferred target for therapeutic interventions for a broad spectrum of human malignancies. Baserga, *Cancer Res.*, 55:249–252 (1995); Baserga, *Cell*, 79:927–930 (1994); Coppola et al., *Mol. Cell. Biol.*, 14:4588–4595 (1994). STKs have been implicated in many types of cancer including notably breast cancer. Cance, et al., *Int. J. Cancer*, 54:571–77 (1993).

The association between abnormal PK activity and disease are not restricted to cancer, however. For example, RTKs have been associated with diseases such as psoriasis, diabetes mellitus, endometriosis, angiogenesis, atheromatous plaque development, Alzheimer's disease, epidermal hyperproliferation and neurodegenerative diseases, age-related macular degeneration, hemangiomas. For example, EGFR is indicated in corneal and dermal wound healing. Defects in the Insulin-R and the IGF-1R have been indicated in type-II diabetes mellitus. A more complete correlation between specific RTKs and their therapeutic indications is set forth in Plowman et al., *DN&P* 7:334–339 (1994). As noted previously, not only RTKs but CTKs as well including, but not limited to, src, abl, fps, yes, fyn, lyn, lck, blk, hck, fgr and yrk (reviewed by Bolen et al., *FASEB J.*, 6:3403–3409 (1992)) are involved in the proliferative and metabolic signal transduction pathway and thus would be expected, and in fact have been shown, to be involved in many PTK-mediated disorders to which the present invention is directed. For example, mutated src (v-src) has been demonstrated as an oncoprotein ($pp60^{v-src}$) in chicken. Moreover, its cellular homolog, the proto-oncogene $pp60^{c-src}$ transmits oncogenic signals of many receptors. For example, over-expression of EGFR or HER2/neu in tumors leads to the constitutive activation of $pp60^{c?src}$, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders. Similarly, Zap70 is implicated in T-cell signaling.

PKs have been implicated in other diseases and disorders. For example, STKs have been associated with inflamation, autoimmune disease, immunoresponses, and hyperproliferation disorders such as restinosis, fibrosis, psoriasis, osteoarthritis and rheumatoid arthritis. PKs have also been implicated in embryo implantation and the compounds of this invention may provide an effective method of preventing embryo implantation. Finally, both RTKs and CTKs are currently suspected as being involved in hyperimmune disorders.

3. SUMMARY OF THE INVENTION

This invention encompasses novel 4-substituted 7-azaindolin-2-ones, pharmaceutical compositions and dosage forms comprising them, methods of their use as protein kinase inhibitors, and methods of their use for the treatment and/or prevention of disease.

A first embodiment of the invention encompasses a compound of Formula 1

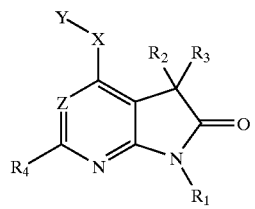

or a pharmaceutically acceptable salt, solvate, clathrate, or prodrug thereof, wherein:

$R_1$ is H or methyl;

each of $R_2$ and $R_3$ is independently H, halogen, ($C_1$–$C_3$) alkyl, or ($C_1$–$C_3$)alkoxy; or $R_1$ and $R_3$ taken together form an optionally substituted methylindene or a 3- to 7-membered ring optionally comprising 0–3 heteroatoms;

$R_4$ is H, methyl, trifluoromethyl, ($C_1$–$C_4$)alkyl, alkoxy, amido, amino, or optionally substituted aryl;

X is a chemical bond, ethynyl, —O—, —S—, —S(O)—, —S($O_2$)—, —$NR_5$C(O)—, or —$NR_5$—, wherein $R_5$ is H, methyl, or substituted methylene;

Y is a 5- to 10-membered mono or bicyclic, saturated, unsaturated, or aromatic ring comprising 0–3 heteroatoms and optionally substituted; and Z is N or $CR_6$, wherein $R_6$ is H, halogen, nitro, cyano, alkoxyl, sulfonamide, amino, or amide.

Preferred compounds of Formula 1 are those wherein X is a chemical bond, —O—, —S—, or —$NR_5$—.

Additional preferred compounds of Formula 1 are those wherein Y is selected from the group consisting of phenyl, indolyl, indolinyl, 1H-indazolyl, 2,3-dihydro-1H-indazolyl, 1H-benzimidazolyl, 2,3-dihydro-1H-benzimidazolyl, benzotriazolyl, pyridyl, pyrimidyl, 4-substituted piperazin-1-yl, morpholino, piperidinyl, pyrrolidin-1-yl, furanyl, thiophenyl, pyrrolyl, pyrazolyl, imidazolyl, pyridopyrrolyl, pyridazopyrrolyl, pyrimidopyrrolyl, pyrazopyrrolyl, pyridofuranyl, and derivatives thereof.

Additional preferred compounds of Formula 1 are those wherein Z is N or CH.

Additional preferred compounds of Formula 1 are those wherein $R_2$ and $R_3$ are both H, halogen, or methyl.

Additional preferred compounds of Formula 1 are those wherein $R_2$ and $R_3$ are taken together to form a ring selected from the group consisting of 1,3-dioxolane, 1,3-dioxane, cyclopropyl, cyclobutyl, cyclopentyl, and cyclohexyl.

Additional preferred compounds of Formula 1 are those wherein $R_2$ and $R_3$ are taken together to form an optionally substituted methylindene selected from those of Formulas 1a-1n:

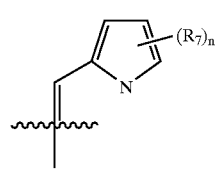

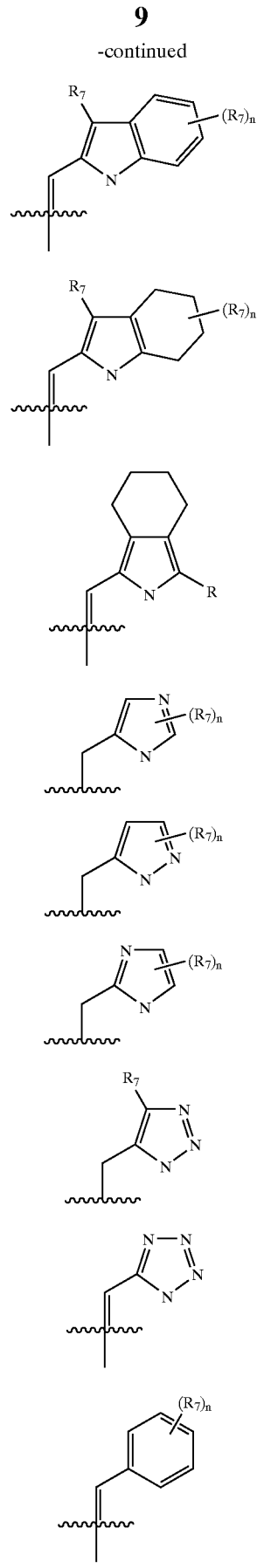

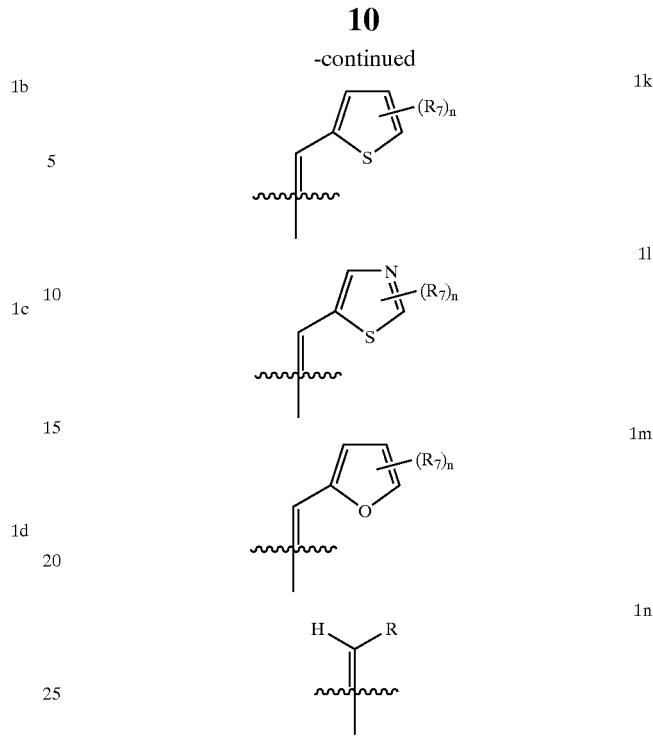

wherein:

n is an integer of 0–3;

each $R_7$ is independently H, alkyl, carboxylic acid, amine, halogen, nitro, cyano, $X_1$, $X_2$—(C—$C_4$)alkyl-$R_8$, $X_2$—($C_1$-$C_4$)alkenyl-$R_8$, or $X_2$—($C_1$-$C_4$)alkynyl-$R_8$;

$X_1$ is —C(O)N$R_9$—, —N$R_9$C(O)—, —C(O)O—, C(O)$R_{11}$, —OC(O)—, —O—, —N$R_9$—, —S—, —S($O_2$), or —S($O_2$)N$R_9$—;

$X_2$ is a chemical bond, —C(O)N$R_9$—, —N$R_9$C(O)—, —C(O)O—, C(O)$R_{11}$, —OC(O)—, —O—, —N$R_9$—, —S—, —S($O_2$), or —S($O_2$)N$R_9$—;

$R_8$ is selected from the group consisting of hydrogen, dialkylamino, carboxyl, hydoxyl, alkoxy, sulfonamide, urea, carbamate, diol, alkylsulphonyl, and $R_{10}$;

$R_9$ is H or ($C_1$–$C_3$)alkyl;

$R_{10}$ is an optionally substituted 5- or 6-membered saturated, unsaturated, or aromatic heterocycle comprising from 1 to 4 heteroatoms; and $R_{11}$ is an optionally substituted 5- or 6-membered saturated heterocyclic ring.

In more preferred compounds of the invention, $R_7$ is $X_2$—($C_1$–$C_4$)alkyl-$R_8$, $X_2$—($C_1$-$C_4$)alkenyl-$R_8$, or $X_2$—($C_1$-$C_4$)alkynyl-$R_8$, and $R_8$ is selected from the group consisting of alkylsulfonyl, alkoxy, carboxyl, morpholino, 1-alkyl-piperazin-4-yl, pyrrolidinyl, piperidinyl, pyridyl, imidazolo, triazolo, tetrazolo, and thiazolo.

Additional preferred compounds of the invention are those of Formula 1 wherein $R_4$ is H, methyl, or trifluoromethyl.

Additional preferred compounds of the invention are those of Formula 1 wherein if Z is CH, $R_1$ is $CH_3$ or $R_3$ and $R_2$ do not form an optionally substituted methylindene.

Specific preferred compounds of the invention are those of Formulas 3–54:

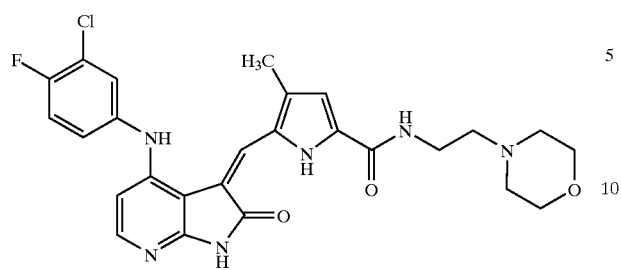
3
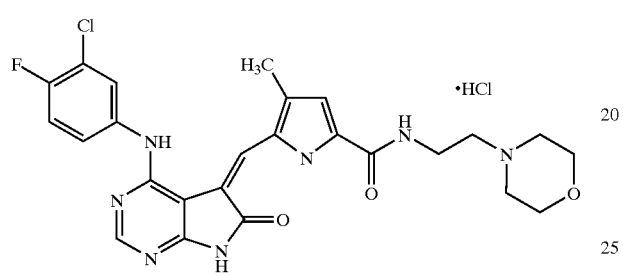
4
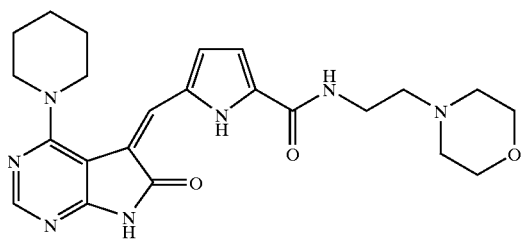
5
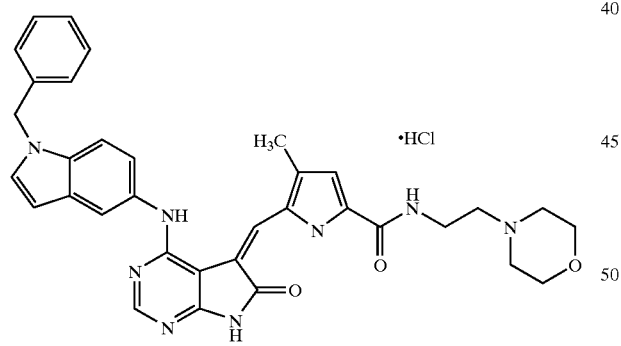
6
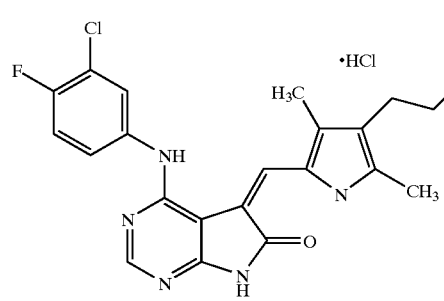
7
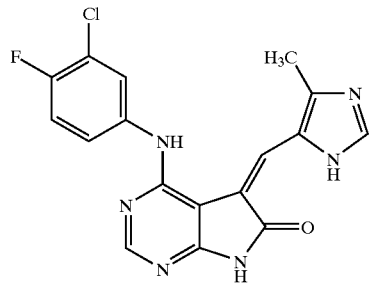
8
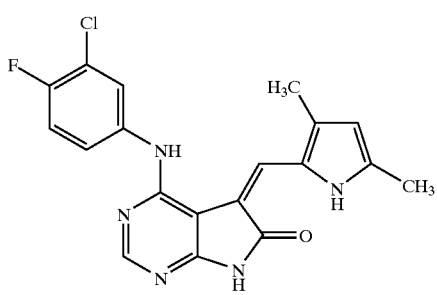
9
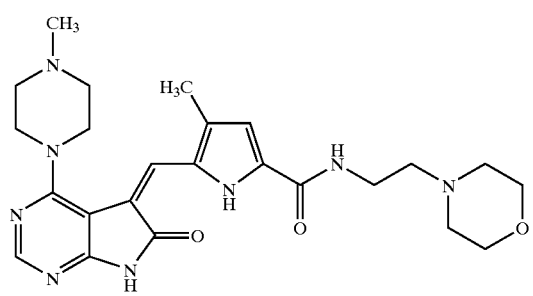
10
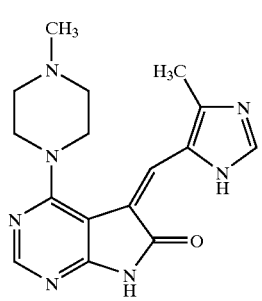
11
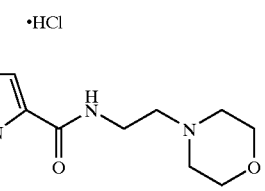
12

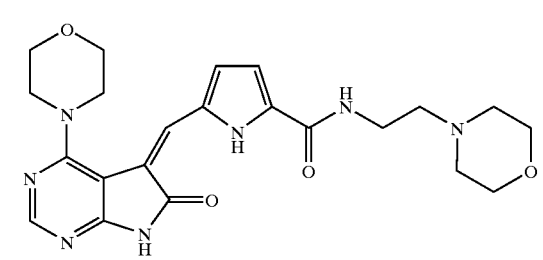
13
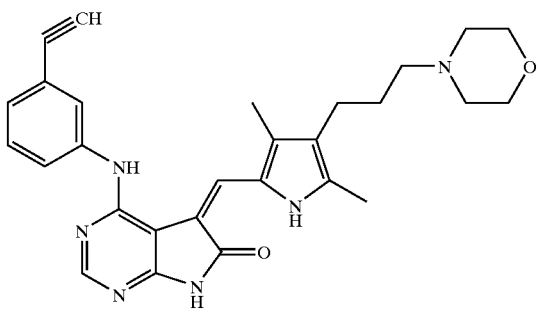
18
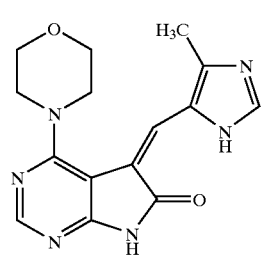
14
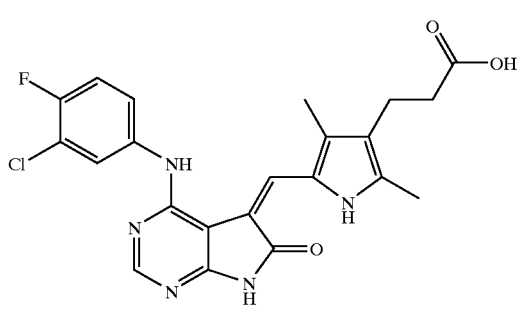
19
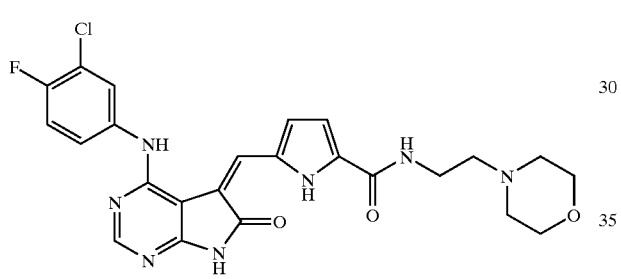
15
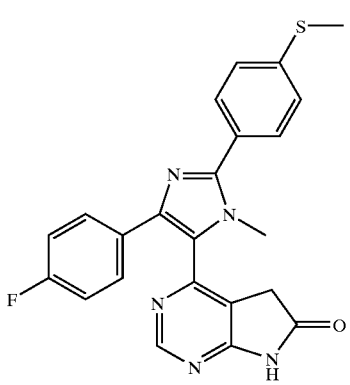
20
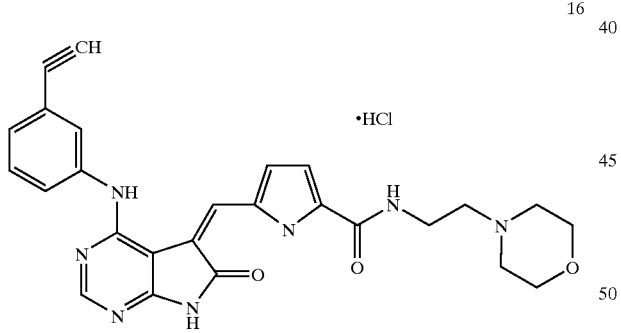
16
·HCl
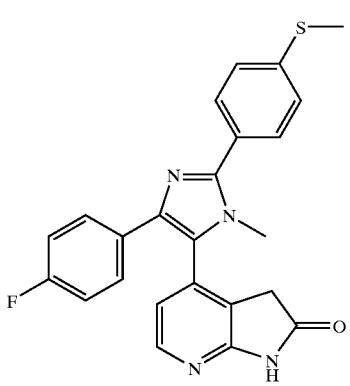
21
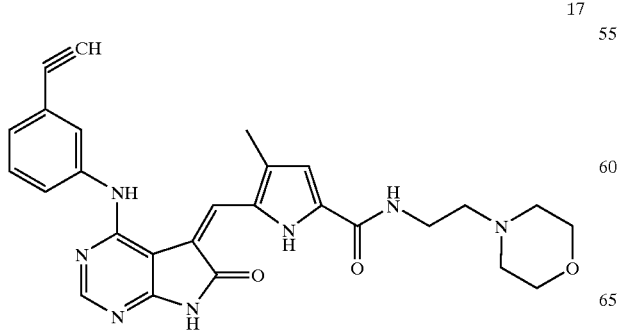
17

22
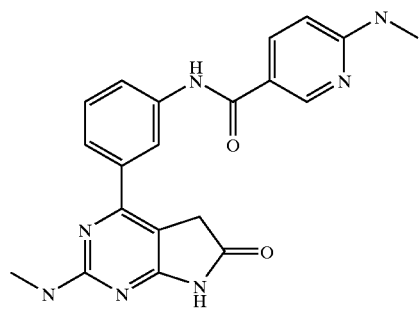
23
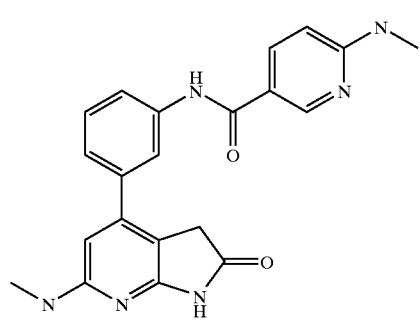
24
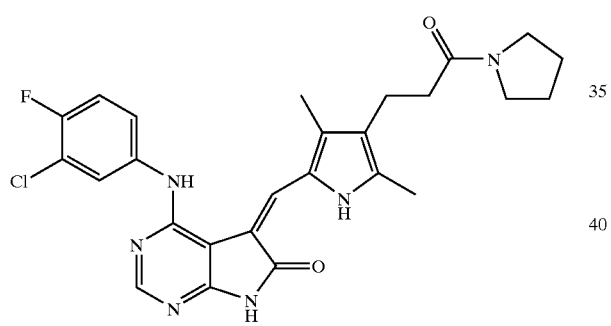
25
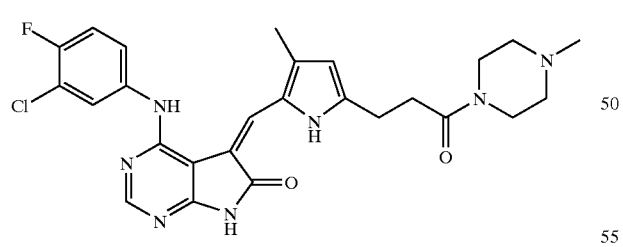
26
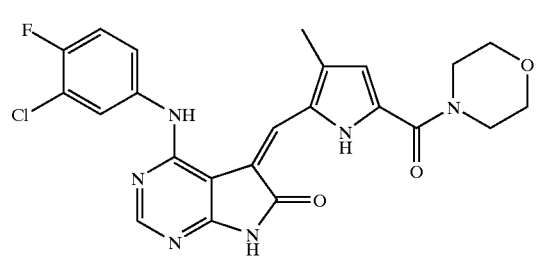
27
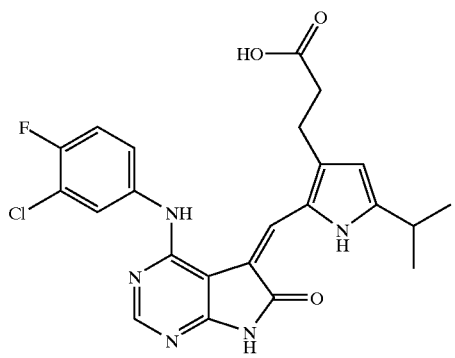
28
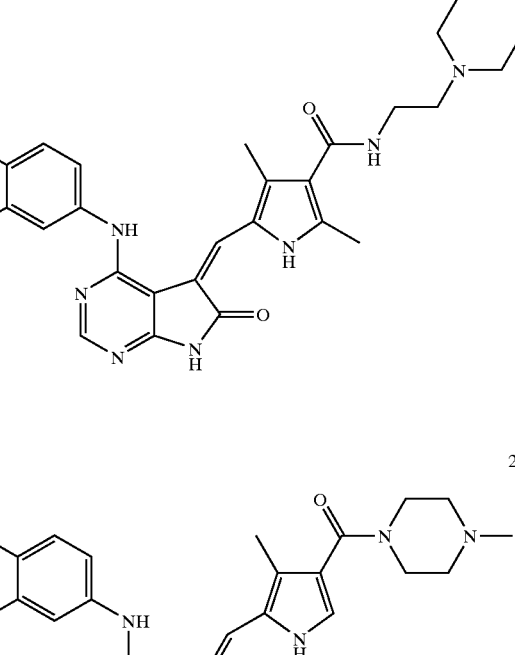
29
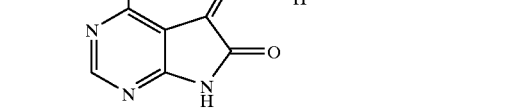
30
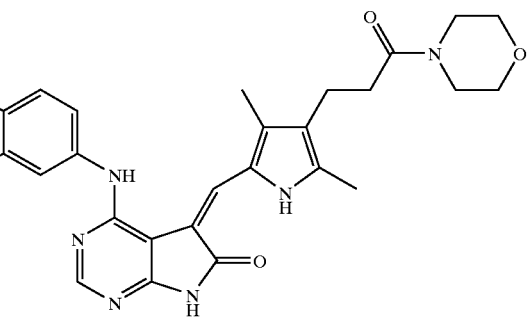

31
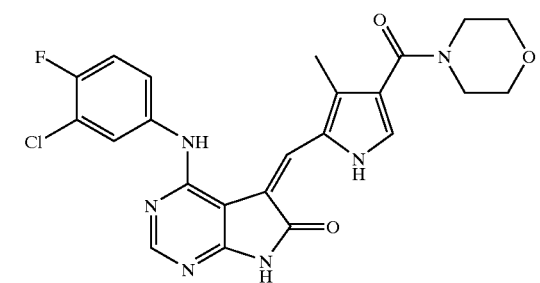
32
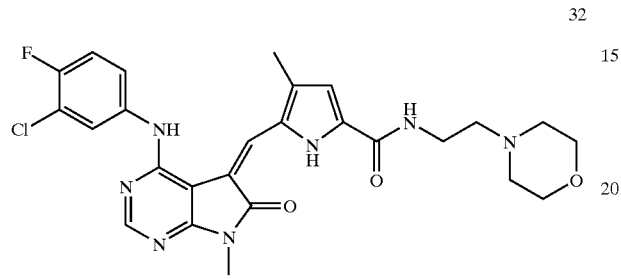
33
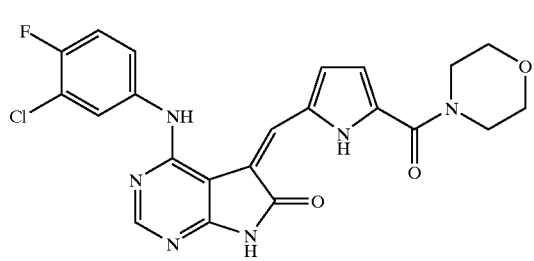
34
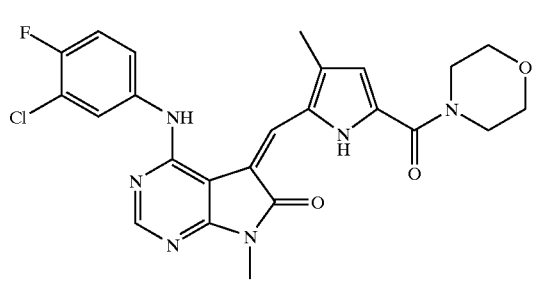
35
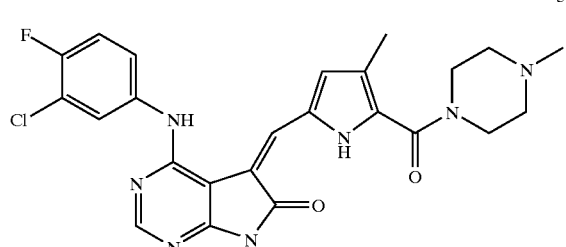
36
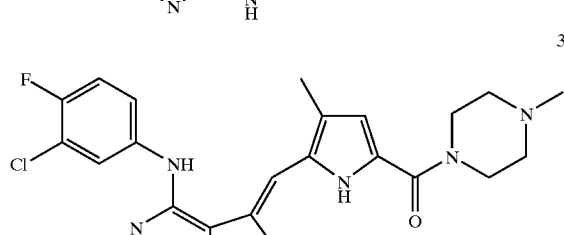
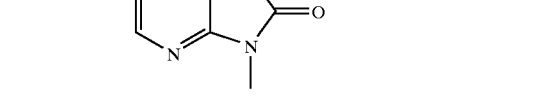
37
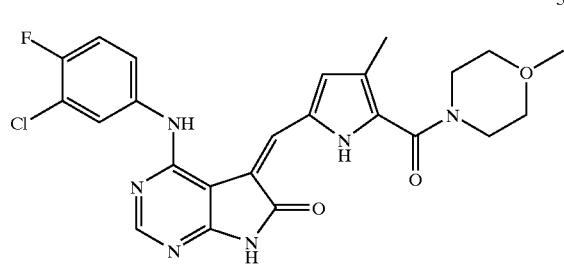
38
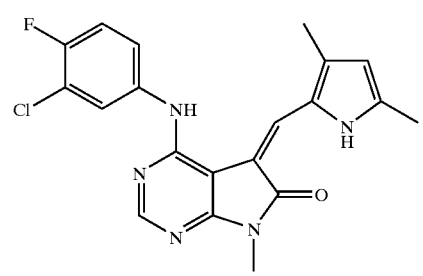
39
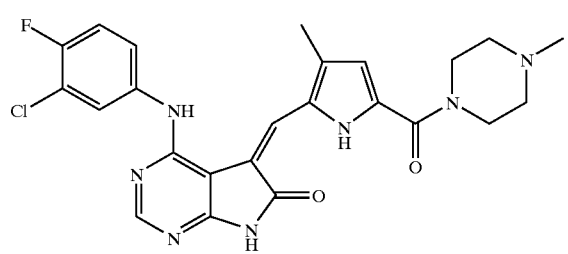
40
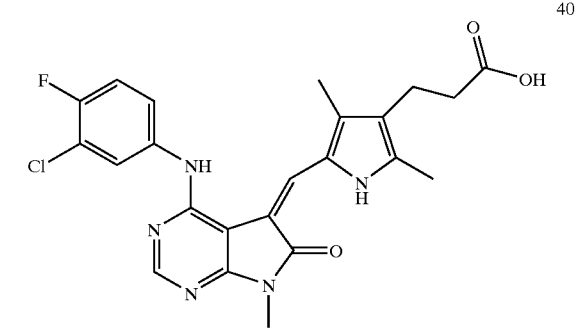
41
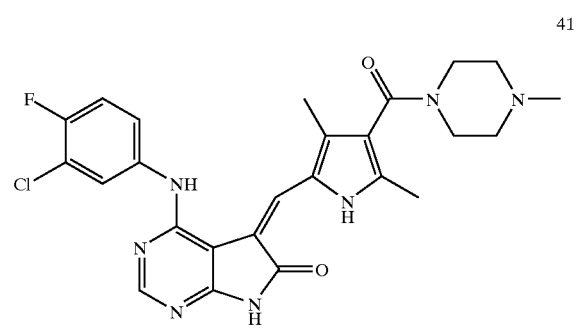

-continued
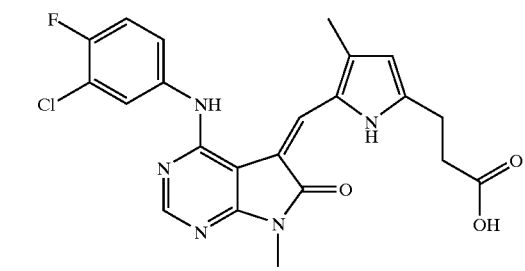
42
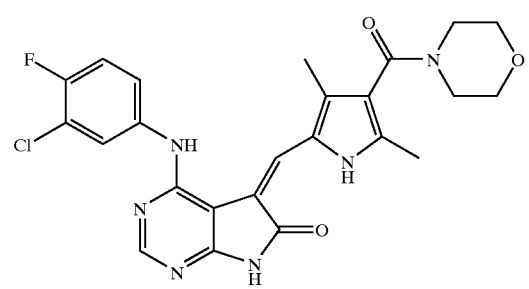
43
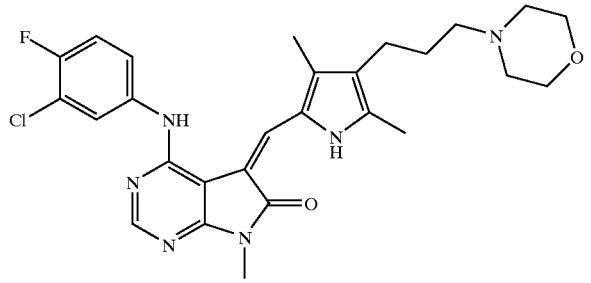
44
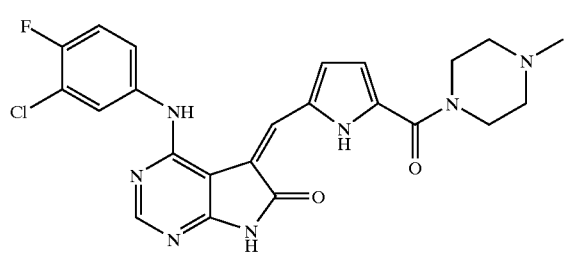
45
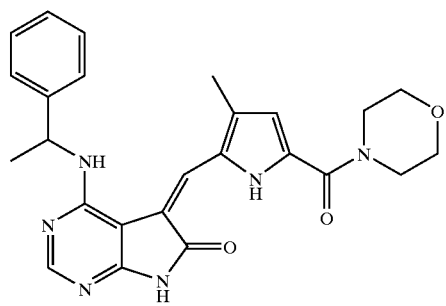
46
-continued
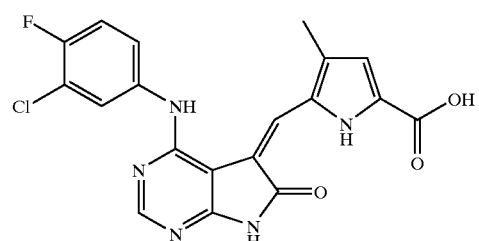
47
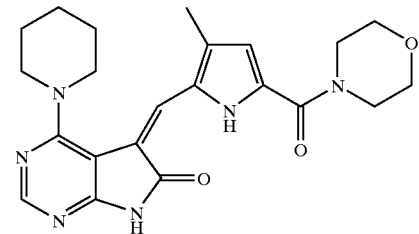
48
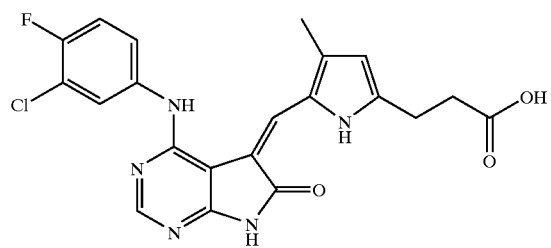
49
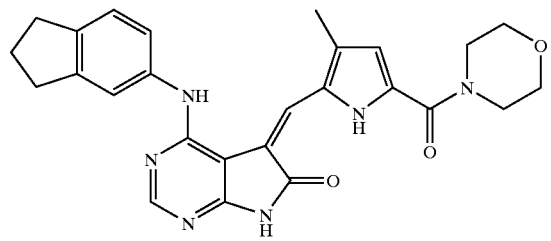
50
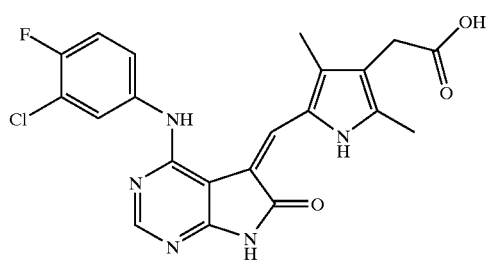
51
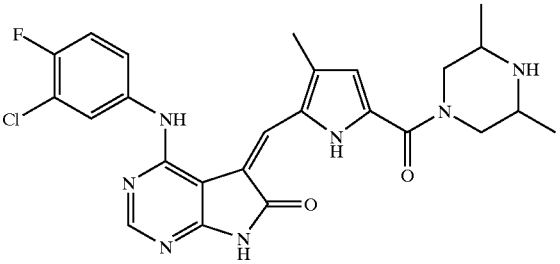
52

53

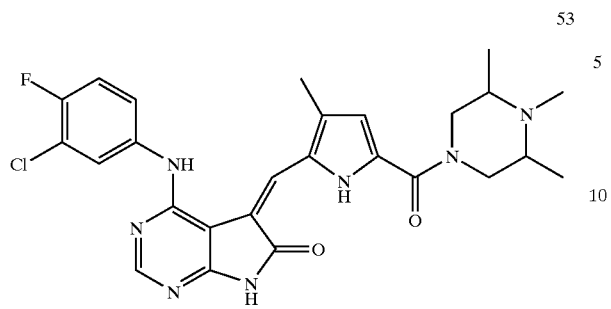

54

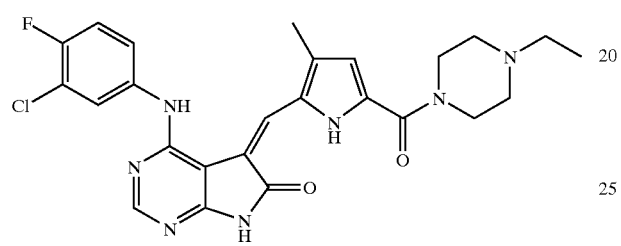

55

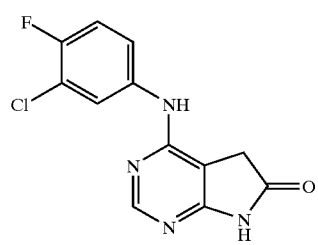

56

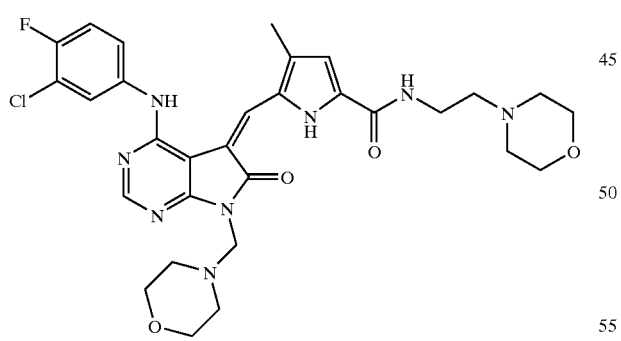

57

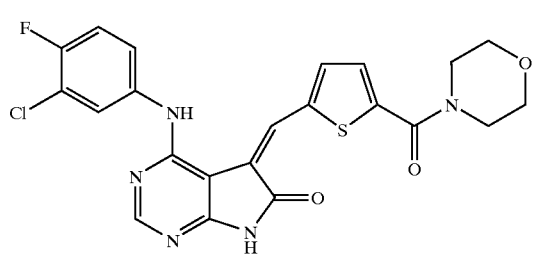

58

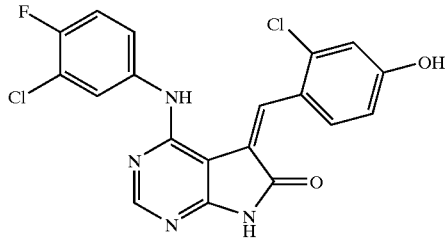

and pharmaceutically acceptable salts, solvates, clathrates, and prodrugs thereof. Preferred pharmaceutically acceptable salts of the compounds of the invention are hydrochloride salts.

A second embodiment of the invention encompasses a method of preparing a compound of Formula 2:

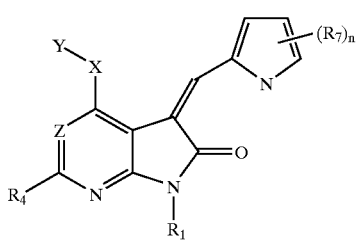

2 wherein X, Y, Z, $R_1$, $R_4$, $R_7$, and n are defined above, which comprises reacting a compound of the formula:

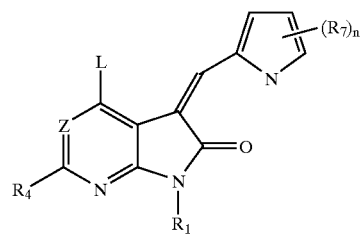

wherein L is a leaving group with a compound of formula YXH under conditions sufficient to form a compound of Formula 2. Preferred leaving groups include, but are not limited to, Br, Cl, $SCH_3$, and $S(O)CH_3$. In a preferred method of this embodiment, the reaction is performed in a solvent. Preferred solvents are polar. More preferred solvents include, but are not limited to, alcohols, DMF, DMSO, and mixtures thereof. In another preferred method of this embodiment, the reaction is catalyzed by a catalyst such as, but are not limited to, AgOTf, $Pd(Ph_3)_4$, and p-TsOH.

A third embodiment of the invention encompasses a method of preparing a compound of Formula 2 which comprises reacting a compound of the formula:

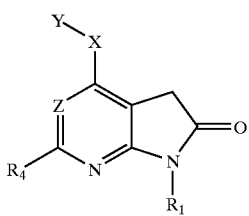

with a compound of the formula:

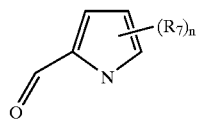

under conditions sufficient to form a compound of Formula 2. In a preferred method of this embodiment, the reaction is performed in a solvent. Preferred solvents are polar. More preferred solvents include, but are not limited to, alcohols, DMF, DMSO, and mixtures thereof. In another preferred method of this embodiment, the reaction is catalyzed by a base. Preferred bases include, but are not limited to, pyridine and piperidine.

A fourth embodiment of the invention encompasses a pharmaceutical composition comprising a compound of Formula 1, or a pharmaceutically acceptable salt, solvate, clathrate, or prodrug thereof, and a pharmaceutically acceptable carrier. This embodiment further encompasses dosage forms suitable for oral, transdermal, topical, parenterat (e.g., subcutaneous, intrathecal, intramuscular, and intravenous), or mucosal (e.g., rectal, vaginal, and nasal) administration. Therefore, solid, lyophilized, injectable and transdermal topical formulations are contemplated herein.

A fifth embodiment of the invention encompasses a method of regulating, modulating, or inhibiting protein kinase activity which comprises contacting a compound of Formula 1, or a pharmaceutically acceptable salt or solvate thereof, with a protein kinase. In a preferred method of this embodiment, the protein kinase is a protein tyrosine kinase. Preferably the contact is made in cell culture (in vitro) or in a human, animal or bird (in vivo).

In another preferred method of this embodiment, the protein kinase is selected from the group consisting of abl, ATK, bcr-abl, Blk, Brk, Btk, c-fms, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, GSK, Gst-Flk1, Hck, Her-2, Her-4, IGF-1R, INS-R, Jak, JNK, KDR, Lck, Lyn, MEK, p38, PANHER, PDGFR, PLK, PKC, PYK2, Raf, Rho, ros, SRC, $tie_1$, $tie_2$, TRK, UL97, VEGFR, Yes, and Zap70.

In a more preferred method of this embodiment, the protein kinase is selected from the group consisting of PANHER, EGFR, Her-2, Her-4, PDGFR, SRC, Lck, cdk2, p38, Raf, and Rho.

In an even more preferred method of this embodiment, the protein kinase is selected from the group consisting of PANHER, CDK2, PDGFR, p38, and Raf.

A sixth embodiment of the invention encompasses a method of treating or preventing a disease characterized by unregulated protein kinase activity which comprises administering to a patient (e.g., a mammal, preferably a human) in need of such treatment or prevention a therapeutically or prophylactically effective amount of a compound of Formula 1, or a pharmaceutically acceptable salt, solvate, clathrate, or prodrug thereof.

In a preferred method of this embodiment, the disease characterized by unregulated protein kinase activity is selected from the group consisting of: blood vessel proliferative disorders such as, but not limited to, arthritis and restenosis; fibrotic disorders such as, but not limited to, hepatic cirrhosis and atherosclerosis; mesangial cell proliferative disorders such as, but not limited to, glomerulonephritis, diabetic nephropathy, malignant nephrosclerosis, thrombotic microangiopathy syndromes, organ transplant rejection, and glomerulopathies; metabolic disorders such as, but not limited to, psoriasis, diabetes mellitus, chronic wounds, inflammation, and neurodegenerative diseases; auto-immune diseases; allergies; asthma; thrombosis; nervous system diseases; and cancer.

In a more preferred method of this embodiment, the disease characterized by unregulated protein kinase activity is cancer. Examples of cancers include, but are not limited to, breast, stomach, ovary, colon, lung (including non-small cell), brain, larynx, lymphatic system, genitourinary tract (including bladder and prostate), ovarian, gastric, bone, and pancreatic cancer.

3.1. Definitions

As used herein, the term "halogen" includes fluorine, chlorine, bromine, and iodine.

As used herein, the term "alkyl" includes saturated monovalent hydrocarbon radicals having straight, cyclic, or branched moieties, and combinations thereof.

As used herein, the term "alkenyl" includes monovalent hydrocarbon radicals having straight, cyclic, or branched moieties, and combinations thereof which comprise at least one carbon-carbon double bond.

As used herein, the term "alkynyl" includes saturated monovalent hydrocarbon radicals having straight, cyclic, or branched moieties, and combinations thereof which comprise at least one carbon-carbon triple bond.

As used herein to describe a compound or moiety, the term "derivative" means a compound or moiety wherein the degree of saturation of at least one bond has been changed (e.g., a single bond has been changed to a double or triple bond) or wherein at least one hydrogen atom is replaced with a different atom or a chemical moiety. Examples of different atoms and chemical moieties include, but are not limited to, halogen, oxygen, nitrogen, sulfur, hydroxy, methoxy, alkyl, amine, amide, ketone, and aldehyde.

As used herein to describe a compound or moiety, the term "substituted" means a compound or moiety wherein at least one hydrogen atom is replaced with a different atom or a chemical moiety. Examples of different atoms and chemical moieties include, but are not limited to, halogen, oxygen, nitrogen, sulfur, hydroxy, methoxy, alkyl, amine, amide, ketone, and aldehyde.

As used herein, the term "heteroatom" means an atom selected from the group consisting of O, S, and N.

As used herein, the term "methylindene" means an optionally substituted carbon-carbon double bond.

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of compounds of Formula 1 that comprise biohydrolyzable moieties such as amides, esters, carbamates, carbonates, or ureides. Such biohydrolyzable moieties may be linked, for example, to a peptide.

As used herein, the terms "biohydrolyzable carbamate," "biohydrolyzable carbonate," and "biohydrolyzable ureide" mean a carbamate, carbonate, or ureide, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, the term "disease characterized by unregulated protein kinase activity" means a disease or condition caused or aggravated by abnormal kinase activity. Examples of such diseases or conditions include, but are not limited to, uncontrolled cell proliferation (e.g., malignant tumour growth) or to defects in key developmental processes. Specific examples include, but are not limited to, central nervous system disorders, inflammatory disorders, bone diseases, atheroscieroses, restenosis, thrombosis, metabolic disorders, and infectious diseases.

As used herein, the term "treat" includes the amelioration, reduction, or eradication of the symptoms of disease.

4. DETAILED DESCRIPTION OF THE INVENTION

This invention encompasses compounds that affect the activity of one or more protein kinases. The invention further encompasses compounds that are useful in methods of regulating, modulating, and/or inhibiting protein kinases of both the receptor and non-receptor types. The invention further provides methods of treating and preventing diseases and disorders that are related to unregulated protein kinase activity in birds and animals, and particularly in mammals such as humans.

Compounds of the invention are those of Formula 1

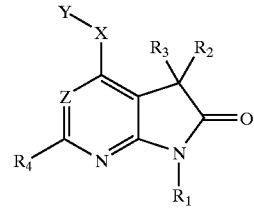

and pharmaceutically acceptable salts, solvates, clathrates, and prodrugs thereof, wherein $R_1$, $R_2$, $R_3$, $R_4$, X, Y, and Z are defined herein. It should be appreciated that certain compounds of the invention may have one or more chiral centers or axes, thus the invention further encompasses racemic and optically pure enantiomers of compounds of Formula 1. The invention also encompasses crystalline and amorphous forms as well as lyophilized, non-lyophilized, and sterile compositions of compounds of Formula 1.

Pharmaceutically acceptable salts of compounds of Formula 1 include salts of acidic or basic moieties. The compounds of the invention that are basic in nature are capable of forming a wide variety of salts with various inorganic and organic acids. Acids that can be used to prepare pharmaceutically acceptable acid addition salts of such basic compounds are those that form non-toxic acid addition salts, i.e., salts that contain pharmacologically acceptable anions such as, but not limited to, hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate [i.e., 1,1'-methylene-bis-(2-hydroxy-3-naphthoate)]. Compounds of the invention that comprise a basic moiety, such as an amino group, can form pharmaceutically acceptable salts with various amino acids in addition to the acids mentioned above.

Compounds of the invention that are acidic in nature are capable of forming base addition salts with various pharmacologically acceptable cations. Examples of such salts include, but are not limited to, the alkali metal or alkaline earth metal salts, e.g., calcium, magnesium, sodium, and potassium salts.

4.1. Synthesis

Compounds of the invention can be readily prepared from 4-chloro-1,3-dihydro-pyrrolo[2,3-b]pyridin-2-one or 4-chloro-5,7-dihydro-pyrrolo[2,3-d]pyrimidine-6-one or other commercially or readily accessible starting material. A preferred method of preparing 4-chloro-1,3-dihydro-pyrrolo[2,3-b]pyridin-2-one is shown in Scheme 1:

Scheme 1

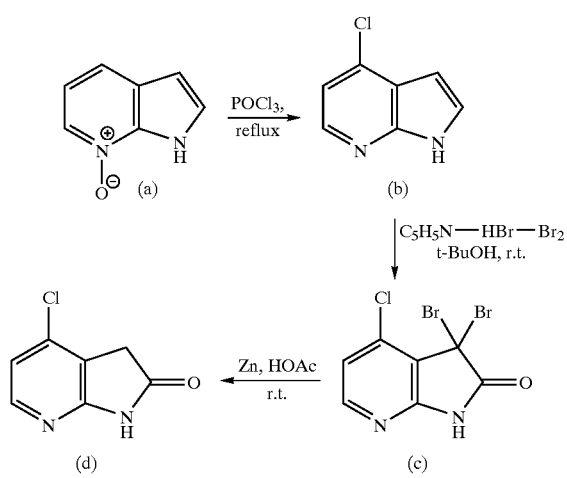

According to Scheme 1, compound (a) is chlorinated to provide compound (b). Although a variety of reaction conditions known to those skilled in the art can be used to chlorinate compound (a), the use of POCl₃ is preferred. Compound (b) is then converted to compound (c) using C₅H₅N—HBr—Br₂ in t-butanol. This reaction is preferably run at room temperature for about four hours, although those skilled in the art will recognize that the solvent and the reaction temperature and time can be varied to maximize the yield of compound (c). Finally, 4-chloro-1,3-dihydro-pyrrolo[2,3-b]pyridin-2-one (compound (d)) is formed by replacing the bromine atoms bound to compound (c) with hydrogen atoms. This is readily accomplished using zinc in acetic acid, although other methods known to those skilled in the art can also be used.

A preferred method of preparing 4-chloro-5,7-dihydro-pyrrolo[2,3-d]pyrimidine-6-one is described in Scheme 2:

Scheme 2

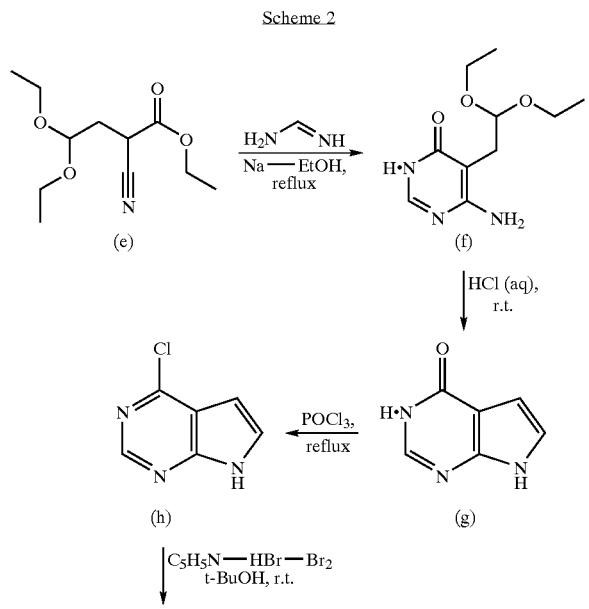

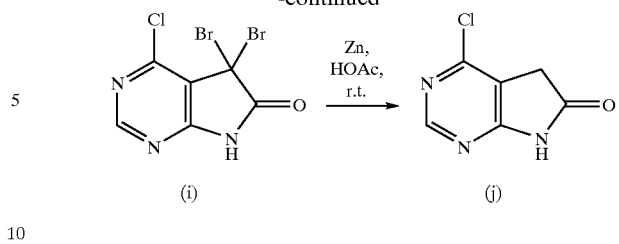

According to Scheme 2, compound (e) is reacted with formamidine hydrochloride under basic conditions to provide compound (f). Compound (f) is then cyclized under acidic conditions, preferably using 1N aqueous HCl, to provide compound (g). The keto moiety of compound (g) is next replaced with a chlorine using, for example, POCl₃. The resulting compound (h) is then converted to compound (i) using C₅H₅N—HBr—Br₂ in t-butanol. This reaction is preferably run at room temperature for about four hours, although those skilled in the art will recognize that the solvent and the reaction temperature and time can be varied to maximize the yield of compound (i). Finally, 4-chloro-5,7-dihydro-pyrrolo[2,3-d]pyrimidine-6-one (compound (j)) is formed by replacing the bromine atoms bound to compound (i) with hydrogen atoms. This is readily accomplished using zinc in acetic acid, although other methods known to those skilled in the art can also be used.

Compounds of the invention are readily prepared from 4-chloro-1,3-dihydro-pyrrolo[2,3-b]pyridin-2-one and 4-chloro-5,7-dihydro-pyrrolo[2,3-d]pyrimidine-6-one. A preferred method is shown in Scheme 3, wherein each of X, Y, Z, R₁, R₄, R₇, L, and n are defined herein:

Scheme 3

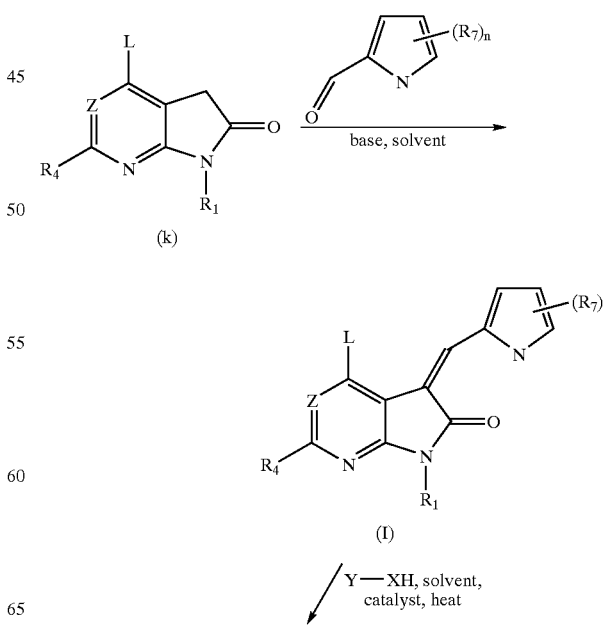

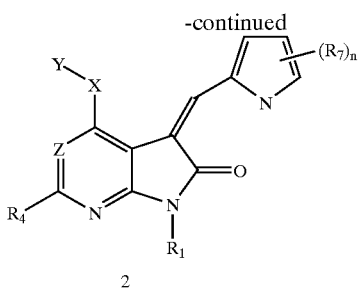

2

According to Scheme 3, the starting material (k) is coupled with a derivative of pyrrole under suitable reaction conditions to yield compound (l). The leaving group L is then replaced with the moiety XY to provide compound 2.

Another preferred method of preparing compounds of the invention is shown in

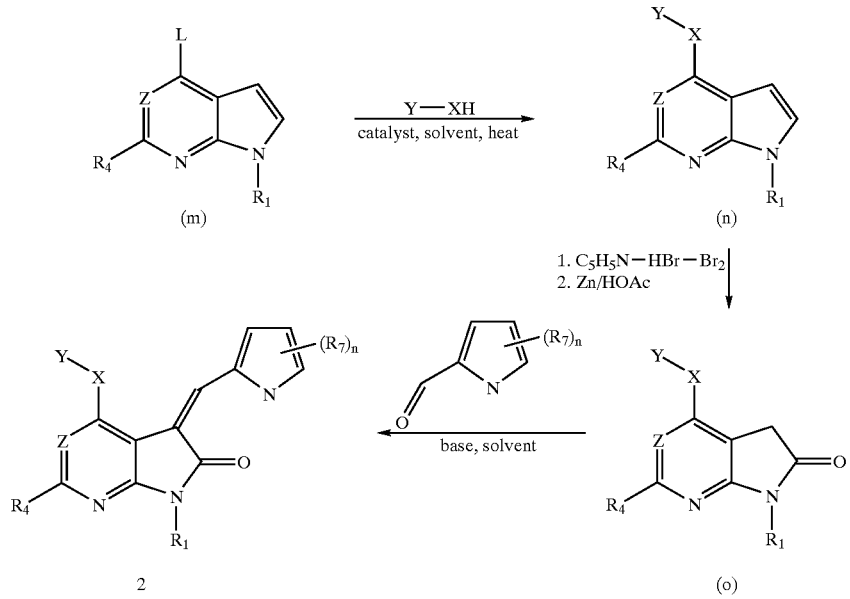

According to Scheme 4, compound (m) is coupled with XY to form compound (n). Compound (n) is then converted to compound (o) using $C_5H_5N$—HBr—$Br_2$ in t-butanol. This reaction is preferably run at room temperature for about four hours, although those skilled in the art will recognize that the solvent and the reaction temperature and time can be varied to maximize the yield of compound (o). Finally, compound (o) is coupled with a derivative of pyrrole under suitable reaction conditions to yield compound 2.

4.2. Biological Activity

The ability of a compound of the invention to affect the activity of a protein kinase can be readily determined using methods well known to those skilled in the art. For example, a compound can be contacted (in vitro or in vivo) with cells that express a kinase of interest, after which: (a) phenotypic changes in the cell culture can be scored as compared to control cells that were not exposed to the compound; or (b) cell lysates can be prepared to assess phosphorylated proteins.

This latter approach is illustrated by several methodologies. A common technique involves incubating cells with a ligand and radioactive phosphate, lysing the cells, separating cellular components using an SDS-polyacrylamide gel (SDS-PAGE) technique, in either one or two dimensions, and then detecting the presence of phosphorylated proteins by exposing X-ray film. A similar technique involves separating cellular components using SDS-PAGE, transferring the separated components to a solid support such as a sheet of nitrocellulose, and then detecting the presence of phosphorylated tyrosines using an antiphosphotyrosine antibody (anti-PY). The anti-PY can be detected by labeling it with a radioactive substance, which then requires scanning the labeled nitrocellulose with a piece of specialized equipment designed to detect radioactivity or exposure of X-ray film. Alternatively, the anti-PY can be labeled with an enzyme, such as horseradish peroxidase, and detected by subsequent addition of a colourometric substrate for the enzyme. A further alternative involves detecting the anti-PY by reacting it with a second antibody that recognizes the anti-PY and is labeled with either a radioactive moiety or an enzyme as previously described. Examples of these and similar techniques are described in Hansen et al., *Electrophoresis* 14:112–126 (1993); Campbell et al., *J. Biol. Chem.* 268:7427–7434 (1993); Donato et al., *Cell Growth and Diff.* 3:258–268 (1992); and Katagiri et al., *J. Immunol.* 150:585–593 (1993).

Other, ELISA-type, assays that can be used to determine the biological activity of a compound of the invention are disclosed by Peraldi et al., *J. Biochem.* 285:71–78 (1992); Schraag et al., *Analytical Biochemistry* 211:233–239 (1993); Cleavland, *Analytical Biochemistry* 190:249–253 (1990); Farley, *Analytical Biochemistry* 203:151–157 (1992); and Lázaro, *Analytical Biochemistry* 192:257–261 (1991).

A preferred method of determining the ability of a compound of the invention to affect protein kinase activity is disclosed by U.S. patent application Ser. No. 08/234,440, which is incorporated herein by reference. According to this method, a target cell that expresses a kinase and is phosphorylated or dephosphorylated during signal transduction is exposed to a compound of the invention. The target cell is thereafter lysed to release cellular contents, which include the protein substrate. The substrate is isolated by contacting the cell lysate with a substrate-specific antibody immobilized on a solid support and subsequently washing away other cellular components. An immunoassay is performed on the isolated substrate to detect the presence or absence of phosphotyrosine residues on the substrate as compared to lysates of control target cells that were not exposed to the compound of interest. Other preferred methods of measuring the biological effects of compounds of the invention are described below in Examples 20–24.

4.3. Pharmaceutical Compositions and Methods of Treatment

Compounds of the invention (herein also referred to as "active ingredients" or "active compounds") can be used to regulate, modulate, or inhibit protein kinase activity. They can thus be used in the treatment and/or prevention of a disease or disorder in birds and animals. Preferred patients are, mammals, and particularly humans. Examples of diseases and disorders that can be treated or prevented by methods of the invention include, but are not limited to, blood vessel proliferative disorders such as, but not limited to, arthritis and restenosis; fibrotic disorders such as, but not limited to, hepatic cirrhosis and atherosclerosis; mesangial cell proliferative disorders such as, but not limited to, glomerulonephritis, diabetic nephropathy, malignant nephrosclerosis, thrombotic microangiopathy syndromes, organ transplant rejection, and glomerulopathies; metabolic disorders such as, but not limited to, psoriasis, diabetes mellitus, chronic wounds, inflammation, and neurodegenerative diseases; auto-immune diseases; allergies; asthma; thrombosis; nervous system diseases; and cancer. Examples of cancers include, but are not limited to, breast, stomach, ovary, colon, lung (including non-small cell lung cancer), brain, larynx, lymphatic system, genitourinary tract (including bladder and prostate), ovarian, gastric, bone, and pancreatic cancer.

4.3.1. Routes of Administration and Dosage Forms

Compounds of the invention can be administered to a patient by any suitable route, including, but not limited to, oral, transdermal, topical, parenteral (e.g., subcutaneous, intrathecal, intramuscular, and intravenous), and mucosal (e.g., rectal, vaginal, and nasal) routes. Dosage forms encompassed by the invention include, but are not limited to, tablets, caplets, capsules, troches, dispersions, suspensions, suppositories, solutions, creams, patches, solutions, lyophilized solids suitable for reconstitution into solutions, and aerosols (e.g., in the form of minipumps).

A compound of the invention can be administered in a local rather than systemic manner by, for example, injection of the compound directly into a solid tumor, often in a depot or sustained release formulation. A compound can further be administered in a targeted drug delivery system, for example, in a liposome coated with tumor-specific antibody. The tiposome will be targeted to, and taken up selectively by, the tumor.

Pharmaceutical compositions of the invention can be manufactured in a manner well known to those skilled in the art, e.g., by means of conventional mixing, dissolving, granulating, dragee-making, levigating, emulsifying, encapsulating, entrapping, or lyophilizing processes. Pharmaceutical compositions can thus be formulated using one or more physiologically acceptable carriers comprising excipients and auxiliaries that facilitate processing of the active compounds into pharmaceutically acceptable preparations. Proper formulation is dependent upon the route of administration chosen.

For injection, an active ingredient can be formulated in an aqueous solution, preferably in a physiologically compatible buffer such as Hanks's solution, Ringer's solution, or physiological saline buffer. For transmucosal administration, penetrants appropriate to the barrier to be permeated are used in the formulation. Such penetrants are generally known in the art.

For oral administration, an active ingredient can be combined with one or more of the many pharmaceutically acceptable carriers well known in the art. Such carriers enable compounds of the invention to be formulated as, for example, tablets, pills, dragees, capsules, liquids, gels, syrups, slurries, and suspensions for oral ingestion by a patient. Pharmaceutical preparations for oral use can be obtained by admixing a compound of the invention with a solid excipient, optionally grinding the resulting mixture, processing the mixture into granules, and adding optional suitable auxiliaries to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as cross-linked polyvinyl pyrrolidone, agar, or alginic acid or a salt thereof such as sodium alginate.

Dragee cores, which can be lactose-free, are provided with suitable coatings to provide tablets of the invention. For this purpose, concentrated sugar solutions, can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be orally administered include push-fit capsules made of gelatin, as well as soft, sealed capsules made of gelatin and a plasticizer such as glycerol or sorbitol. The push-fit capsules can contain an active ingredient in admixture with fillers such as lactose, binders such as starches, and/or lubricants such as talc or magnesium stearate and, optionally, stabilizers. In soft capsules, the active compound can be dissolved or suspended in any suitable liquid, such as fatty oils, liquid paraffin, or liquid polyethylene glycols. Stabilizers can also be added. All formulations for oral administration should be in dosages suitable for such administration.

For buccal administration, dosage forms of the invention can take the form of tablets or lozenges formulated in conventional manner.

For administration by inhalation, active ingredients of the invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, or carbon dioxide. In the case of a pressurized aerosol, the dosage unit can be determined by providing a valve to deliver a metered amount. Capsules and cartridges of, for example, gelatin for use in an inhaler or insufflator can be formulated to contain a powder mix of the compound and a suitable powder base such as lactose or starch.

Compounds of the invention can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions.

Active ingredients of the invention can also be in powder form for constitution with a suitable vehicle, e.g., sterile pyrogen-free water, before use.

Compounds of the invention can also be formulated in rectal compositions such as suppositories or retention enemas containing, for example, conventional suppository bases such as cocoa butter or other glycerides. The compounds disclosed herein can further be formulated as depot preparations. Such long acting formulations can be administered by implantation (e.g., subcutaneous or intramuscular) or by intramuscular injection. Thus, for example, an active ingredient can be formulated with suitable polymeric or hydrophobic materials (for example as an emulsion in an acceptable oil) or ion exchange resins, or as a sparingly soluble derivative, for example as a sparingly soluble salt.

A preferred pharmaceutical carrier for compounds of the invention that are hydrophobic is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other tow-toxicity nonpolar surfactants can be used instead of polysorbate 80; the fraction size of polyethylene glycol can be varied; other biocompatible polymers can replace polyethylene glycol, e.g., polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, compounds of the invention can be delivered using a sustained-release system, such as semipermeable matrices of solid hydrophobic polymers containing the therapeutic agent. A variety of sustained-release materials are well known by those skilled in the art. Sustained-release capsules can, depending on their chemical nature, release the compounds for a few weeks up to over 100 days. Depending on the chemical nature and the biological stability of the therapeutic reagent, additional strategies for protein stabilization can be employed.

Pharmaceutical compositions also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

In addition to the common dosage forms set out herein, the compounds of the invention can be administered by controlled release means and/or delivery devices including, but not limited to, Alzet® osmotic pumps which are available from Alza Corporation, Palo Alto, Calif. Suitable delivery devices are described in U.S. Pat. Nos. 3,536,809; 3,598,123; 3,845,770; 3,916,899; 3,944,064; and 4,008,719, the disclosures of which are incorporated herein by reference.

Compositions of the invention can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration. Compositions comprising a compound of the invention formulated in a compatible pharmaceutical carrier can also be prepared, placed in an appropriate container, and labeled for treatment of an indicated condition. Suitable conditions indicated on the label can include treatment of a tumor, such as a glioma or glioblastoma, atid inhibition of angiogenesis.

Pharmaceutical compositions suitable for use in this invention include compositions wherein the active ingredient(s) is contained in an effective amount to achieve its intended purpose. Determination of effective amounts is well within the capability of those skilled in the art, especially in light of the detailed disclosure provided herein.

4.3.2. Dosages

For any compound used in the methods of the invention, a therapeutically or prophylactically effective dose can be initially estimated from cell culture assays. For example, a dose can be formulated in animal models to achieve a circulating concentration range that includes the $IC_{50}$ as determined in cell culture (i e., the concentration of the test compound which achieves a half-maximal inhibition of the kinase activity). Such information can be used to more accurately determine useful doses in humans.

A therapeutically effective amount refers to that amount of a compound that results in amelioration of symptoms or a prolongation of survival in a patient. A prophylactically effective amount refers to that amount of a compound which is sufficient to prevent or slow the onset of a disease or condition. Toxicity and therapeutic efficacy of compounds of the invention can be determined by standard pharmaceutical procedures in cell cultures or experimental animals wherein the $LD_{50}$ (the dose lethal to 50% of the population) and the $ED_{50}$ (the dose therapeutically effective in 50% of the population) is determined. The dose ratio between toxic and therapeutic or prophylactic effects is the therapeutic index and it can be expressed as the ratio of $LD_{50}$ to $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration, and dosage can be chosen by the individual physician in view of the patient's condition. See, e.g., Fingl et al., *The Pharmacological Basis of Therapeutics* 1 (1975).

Dosage amount and interval can be adjusted individually to provide plasma levels of the active ingredient that are sufficient to maintain the kinase modulating effects, or minimal effective concentration (MEC). The MEC will vary for each compound, but can be estimated from in vitro data; e.g., the concentration necessary to achieve a 50–90% inhibition of the kinase using the assays described herein. Dosages necessary to achieve the MEC will depend on individual characteristics and route of administration, but high performance liquid chromatography (HPLC) assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

Usual patient dosages for systemic administration range from 1 to 2000 mg/day, commonly from 1 to 250 mg/day, and typically from 10 to 150 mg/day. Stated in terms of patient body weight, usual dosages range from 0.02 to 25 mg/kg/day, commonly from 0.02 to 3 mg/kg/day, typically from 0.2 to 1.5 mg/kg/day. Stated in terms of patient body surface areas, usual dosages range from 0.5 to 1200 mg/m²/day, commonly from 0.5 to 150 mg/m²/day, typically from 5 to 100 mg/m²/day. Usual average plasma levels should be maintained within 50 to 5000 µg/ml, commonly 50 to 1000 µg/ml, and typically 100 to 500 µg/ml, although in cases of local administration or selective uptake the effective local concentration of the drug can not be related to plasma concentration. As those skilled in the art will recognized, however, these dosages and plasma levels will vary with the patient, the disease treated (e.g., different cancers may require different dosages), the route of administration, and the particular active ingredient used. The dose, and perhaps the dosage frequency, will also vary according to the age, body weight, and response of the individual patient. It is thus recommended that infants, children, and patients over 65 years, and those with impaired renal, or hepatic function, initially receive low doses, and that they be titrated based on individual clinical response(s) and blood level(s).

Desirable blood levels can be maintained by a continuous infusion of the compound as ascertained by plasma levels measured by HPLC. It should be noted that the attending physician would know how and when to terminate, interrupt, or adjust therapy to lower dosage due to toxicity, or to bone marrow, liver, or kidney dysfunction. The attending physician would also know to adjust treatment to higher levels if the clinical response is not adequate (precluding toxicity).

Further advantages of the invention can be understood from the following non-limiting Examples.

5. EXAMPLES

5.1. Example 1

SYNTHESIS OF 4-CHLORO-1,3-DIHYDRO-PYRROLO[2,3-D]PYRIDIN-2-ONE

1H-Pyrrolo[2,3-b]pyridine 7-oxide (1.86 g, 13.9 mmol, literature reference: *J. Org. Chem.* 45(20):4045–8 (1980)) was dissolved in 10 mL of phosphorus oxychloride. The reaction mixture was refluxed for 6 hours, cooled to room temperature and concentrated. The residue was extracted with ethyl acetate/water. The organic layer was washed with brine to pH 6, dried over anhydrous sodium sulfate, concentrated and dried in a vacuum oven overnight to give 0.88 g (42%) of 4-chloro-1H-pyrrolo[2,3-b]pyridine as a tan solid. $^1$H NMR (360 MHz, DMSO-$d_6$) δ 11.99 (s, br, 1H, NH), 8.16 (d, J=5.15 Hz, 1H), 7.57 (t, br, J=3.38 Hz, 1H), 7.17 (d, J=5.15 Hz, 1H), 6.49 (dd, J=1.80, 3.38 Hz, 1H). MS m/e 153 [M$^+$].

To a stirred solution of 4-chloro-1H-pyrrolo[2,3-b] pyridine (0.4 g, 2.6 mmol) in t-butanol (25 mL) was added pyridinium bromide perbromide (PBPB, 2.5 g, 7.8 mmol) portionwise. The reaction mixture was stirred at room temperature for 3 hours and added another 0.39 g (3.1 mmol) of PBPB. The resultant reaction mixture was further stirred for 1 hour and extracted with ethyl acetate/water. The organic layer was washed with brine, dried over anhydrous magnesium sulfate and concentrated. Trituration of the crude product with dichloromethane gave 0.733 g (86%) of 3,3-dibromo-4-chloro-1,3-dihydro-pyrrolo[2,3-b]pyridin-2-one as a tan solid. $^1$H NMR (360 MHz, DMSO-$d_6$) δ 12.23 (s, br, NH), 8.20 (d, J=5.66 Hz, 1H), and 7.30 (d, J=5.66 Hz, 1H). MS m/e 326 [M$^+$].

A mixture of 3,3-dibromo-4-chloro-1,3-dihydro-pyrrolo [2,3-b]pyridin-2-one (0.745 g, 2.3 mmol), zinc dust (1.49 g, 23 mmol), acetic acid (10 mL) and methanol (10 mL) was stirred at room temperature for 2 hours. The reaction mixture was then diluted with brine and extracted with ethyl acetate. The organic layer was further washed with brine, dried over anhydrous sodium sulfate, concentrated and dried in a vacuum oven to give 0.3 g (78%) of 4-chloro-1,3-dihydro-pyrrolo[2,3-b]pyridin-2-one as a tan solid. $^1$H NMR (360 MHz, DMSO-$d_6$) δ 11.21 (s, br, NH), 8.01 (d, J=5.66 Hz, 1H), 7.23 (d, J=5.66 Hz, 1H), and 3.59 (s, 2H, CH$_2$). MS m/e 168 [M$^+$].

5.2. Example 2

SYNTHESIS OF 4-CHLORO-5,7-DIHYDRO-PYRROLO[2,3-D]PYRIMIDIN-6-ONE

To a solution of 45.2 mmol of sodium ethoxide (made in situ from sodium and absolute ethanol) in 40 mL of absolute ethanol was added formamidine hydrochloride (1.74 g, 21.5 mmol) and 2-cyano-4,4-diethoxy-butyric acid ethyl ester (2.47 g, 11 mmol, literature reference: Davoll, J., *J. Chem. Soc.* 131–138 (1960)). The mixture was refluxed for 6 hours, cooled to room temperature and filtered. The solid was washed with hot acetonitrile. The filtrate was neutralized with acetic acid to pH 6.5 and then evaporated to half of the volume. Ethyl acetate (50 mL) was added to the resultant filtrate. The precipitate was filtered, washed with EtOAc to give 1.6 g (66%) of 6-amino-5-(2,2-diethoxy-ethyl)-3H-pyrimidin-4-one as a white solid which was used without further purification. $^1$H NMR (300 MHz, DMSO-$d_6$) δ 11.46 (s, br, 1H, NH), 7.68 (s, 1H), 6.07 (s, br, 2H, NH$_2$), 4.54 (t, J=6.0 Hz, 1H, CH(OCH$_2$CH$_3$)$_2$), 3.53–5.62 (m, 2H, CH(OCH$_2$CH$_3$)$_2$), 3.31–3.49 (m, 2H, CH(OCH$_2$CH$_3$)$_2$), 2.50 (m, 2H, CH$_2$), and 1.05 (t, J=6.93 Hz, 6H, CH(OCH$_2$CH$_3$)$_2$).

6-Amino-5-(2,2-diethoxy-ethyl)-3H-pyrimidin-4-one (150 mg, 0.7 mmol) was dissolved in 5.0 mL of 1N HCl solution. The mixture was stirred at room temperature for 1 hour and the precipitate was filtered, washed with minimal amount of water and dried in a vacuum oven overnight to give 60 mg (64%) of 3,7-dihydro-pyrrolo[2,3-d]pyrimidin-4-one as a white solid. $^1$H NMR (360 MHz, DMSO-d$_6$) δ 11.83 (s, 1H, NH), 1.75 (s, 1H, NH), 7.80 (s, 1H), 7.01 (dd, J=2.65, 3.21 Hz, 1H), and 6.42 (dd, J=2.09, 3.21 Hz, 1H). MS m/e 134 [M+1]$^+$.

3,7-Dihydro-pyrrolo[2,3-d]pyrimidin-4-one (60 mg, 0.45 mmol) was reacted with 3.0 mL of phosphorus oxychloride to give 49 mg (70%) of 4-chloro-7H-pyrrolo[2,3-d]pyrimidine as an off-white solid. $^1$H NMR (300 MHz, DMSO-d$_6$) δ 12.57 (s, br, 1H, NH), 8.58 (s, 1H), 7.68 (dd, J=2.53, 3.36 Hz, 1H), and 6.59 (dd, J=1.86, 3.36 Hz, 1H). MS m/e 153 [M−1]$^+$.

4-Chloro-7H-pyrrolo[2,3-d]pyrimidine (245 mg, 1.65 mmol) was oxidized using PBPB to give 230 mg (42%) of 5,5-dibromo-4-chloro-5,7-dihydro-pyrrolo[2,3-d]pyrimidin-6-one as a white solid. It was then reduced using zinc dust to give 80 mg (42%) of 4-chloro-5,7-dihydro-pyrrolo[2,3-d]pyrimidin-6-one as a light tan solid.

5.3. Example 3

SYNTHESIS OF 5-[4-(3-CHLORO-4-FLUORO-PHENYLAMINO)-2-OXO-1,2-DIHYDRO-PYRROLO[2,3-B]PYRIDIN-3-YLIDENEMETHYL]-4-METHYL-1H-PYRROLE-2-CARBOXYLIC ACID (2-MORPHOLIN-4-YL-ETHYL)-AMIDE (FORMULA 3)

To ice-cold 3 mL (39.2 mmol) of N,N-dimethylformamide (DMF) was added phosphorus oxychloride (0.67 mL, 7.18 mmol) dropwise and the resultant mixture was stirred for 30 minutes. A solution of 1 g (6.53 mmol) of 4-methyl-1H-pyrrole-2-carboxylic acid ethyl ester in 3 mL of DMF was added to the reaction. After 1 hour, the reaction was warmed to room temperature for another 2.5 hours. The reaction mixture was diluted with water (100 mL) and basified to pH=11 with 1N sodium hydroxide solution. The precipitate was removed by filtration, rinsing with water and dried to afford 0.8 g (68%) of 5-formyl-4-methyl-1H-pyrrole-2-carboxylic acid ethyl ester as a white solid. $^1$H NMR (360 MHz, DMSO-d$_6$) d 12.6 (br s, 1H, NH), 9.78 (s, 1H, CHO), 6.68 (s, 1H), 4.26 (q, J=7.0 Hz, 2H, OCH$_2$CH$_3$), 2.28 (s, 3H, CH$_3$), 1.28 (t, J=7.0 Hz, 3H, OCH$_2$CH$_3$). MS 181 [M$^+$].

To a solution of 0.8 g (4.4 mmol) of 5-formyl-4-methyl-1H-pyrrole-2-carboxylic acid ethyl ester in 35 mL of water and 15 mL of ethanol was added 0.5 g (8.9 mmol) of potassium hydroxide. The reaction mixture was heated to 100° C. for 1 hour, cooled to room temperature, and evaporated ethanol. The water layer was acidified to pH=3 using 2N. hydrogen chloride solution. The precipitate was filtered and washed with water to afford 0.67 g (68%) of 5-formyl-4-methyl-1H-pyrrole-2-carboxylic acid as a tan solid. $^1$H NMR (360 MHz, DMSO-d$_6$) δ12.92 (br s, 1H, CO$_2$H), 12.48 (br s, 1H, NH), 9.76 (s, 1H, CHO-5), 6.63 (s, 1H), 2.28 (s, 3H, CH$_3$). MS m/z 152 [M−1].

To a suspension of 5-formyl-4-methyl-1H-pyrrole-2-carboxylic acid (2 g, 13 mmol) in acetonitrile was added 4-(2-aminoethyl)morpholine (1.9 mL, 14 mmol), EDC (2.7 g, 14 mmol), HOBt (1.9 g, 14 mmol) and triethylamine (3.6 mL, 26 mmol) sequentially. The reaction mixture was stirred at room temperature for 12 hours and concentrated at reduced pressure. The residue was dissolved in 300 mL of 1N hydrogen chloride solution. The aqueous layer was washed with 150 mL of ethyl acetate twice and basified with sodium bicarbonate. The product was then extracted with 250 mL of dichloromethane twice, dried over MgSO$_4$, and concentrated to afford 1.8 g (53%) of 5-formyl-4-methyl-1H-pyrrole-2-carboxylic acid (2-morpholin-4-yl-ethyl)-amide as a yellowish solid. $^1$H NMR (300 MHz, DMSO-d$_6$) d 12.19 (br s, 1H, NH), 9.72 (s, 1H, CHO), 8.29 (br t, J=6.6 Hz, 1H, CONH), 6.65 (d, J=1.7 Hz, 1H), 3.5 (m, 4H), 3.3 (m, 2H, CONHCH$_2$), 2.4 (m, 6H), 2.28 (s, 3H, CH$_3$). MS m/z 265 [M$^+$].

A reaction mixture of 4-chloro-1,3-dihydro-pyrrolo[2,3-b]pyridin-2-one (85 mg, 0.5 mmol), 5-formyl-4-methyl-1H-pyrrole-2-carboxylic acid (2-morpholin-4-yl-ethyl)-amide (125 mg, 0.5 mmol), 0.1 mL of piperidine and 10 mL of ethanol was stirred at room temperature overnight. The yellow precipitate was filtered after cooled with an ice bath, washed with cold ethanol and dried to give 185 mg (92%) of 5-(4-chloro-2-oxo-1,2-dihydro-pyrrolo[2,3-b]pyridin-3-ylidenemethyl)-4-methyl-1H-pyrrole-2-carboxylic acid (2-morpholin-4-yl-ethyl)-amide.

A mixture of 5-(4-chloro-2-oxo-1,2-dihydro-pyrrolo[2,3-b]pyridin-3-ylidenemethyl)-4-methyl-1H-pyrrole-2-carboxylic acid (2-morpholin-4-yl-ethyl)-amide (10 mg, 0.024 mmol), 3-chloro-4-fluoro-phenylamine (50 mg, 0.34 mmol), p-toluene sulfonic acid monohydrate (5 mg, 0.026 mmol) and 1 mL of 2-methoxyethyl ether was heated to 180–190° C. in a sealed tube for 6 hours, cooled to room temperature and concentrated. The residue was then purified using preparative TLC plates eluting with 10% methanol in dichloromethane to give 5-[4-(3-chloro-4-fluoro-phenylamino)-2-oxo-1,2-dihydro-pyrrolo[2,3-b]pyridin-3-ylidenemethyl]-4-methyl-1H-pyrrole-2-carboxylic acid (2-morpholin-4-yl-ethyl)-amide as an orange solid (yield is about 28%).

5.4. Example 4

SYNTHESIS OF 5-[4-(3-CHLORO-4-FLUORO-PHENYLAMINO)-6-OXO-6,7-DIHYDRO-PYRROLO[2,3-D]PYRIMIDIN-5-YLIDENEMETHYL]-4-METHYL-1H-PYRROLE-2-CARBOXYLIC ACID (2-MORPHOLIN-4-YL-ETHYL)-AMIDE HYDROCHLORIDE (FORMULA 4)

4-Chloro-5,7-dihydro-pyrrolo[2,3-d]pyrimidin-6-one (80 mg, 0.47 mmol) was condensed with 5-formyl-4-methyl-1H-pyrrole-2-carboxylic acid (2-morpholin-4-yl-ethyl)-amide (124 mg, 0.47 mmol) at room temperature to give 50 mg (26%) of 5-(4-chloro-6-oxo-6,7-dihydro-pyrrolo[2,3-d]pyrimidin-5-ylidenemethyl)-4-methyl-1H-pyrrole-2-carboxylic acid (2-morpholin-4-yl-ethyl)-amide as a yellow solid.

A mixture of 5-(4-chloro-6-oxo-6,7-dihydro-pyrrolo[2,3-d]pyrimidin-5-ylidenemethyl)-4-methyl-1H-pyrrole-2-carboxylic acid (2-morpholin-4-yl-ethyl)-amide (44 mg, 0.11 mmol), 3-chloro-4-fluoro-phenylamine (154 mg, 1.1 mmol) and p-toluenesulfonic acid monohydrate (10.1 mg, 0.053 mmol), 1-methyl-2-pyrrolidinone (2.5 mL) and 2-methoxyethyl ether (2.5 ml) was heated to 190° C. for 16 hours and concentrated. The residue was purified by reverse phase HPLC, then dissolved in 2N HCl and acetonitrile and freeze-dried to give 24 mg (39%) of 5-[4-(3-chloro-4-fluoro-phenylamino)-6-oxo-6,7-dihydro-pyrrolo[2,3-d]pyrimidin-5-ylidenemethyl]-4-methyl-1H-pyrrole-2-carboxylic acid (2-morpholin-4-yl-ethyl)-amide hydrochloride as a red solid. $^1$H NMR (360 MHz, DMSO-d$_6$) δ 13.46 (s, 1H, NH), 11.79 (s, 1H, NH), 10.74 (br s, 1H, HCl), 9.33 (s, 1H), 8.83 (t, J=5.5 Hz, 1H, NH), 8.33 (s, 1H, H-vinyl), 7.74 (dd, J=2.39, 6.68 Hz, 1H), 7.38–7.47 (m, 2H), 7.35 (t, J=9.03, 1H), 6.94 (s, br, 1H), 3.96 (dt, J=5.74, 11.37 Hz, 2H, CH$_2$), 3.80 (t, J=12.10 Hz, 2H, CH$_2$), 3.68 (dd, J=5.99 & 11.61 Hz, 2H, CH$_2$), 3.52 (d, br, J=12.44 Hz, 2H, CH$_2$), 3.29–3.31 (m, 2H, CH$_2$), 3.10–3.13 (m, 2H, CH$_2$), and 2.23 (s, 3H, CH$_3$). MS 526 [M$^+$].

5.5. Example 5

SYNTHESIS OF 5-(6-OXO-4-PIPERIDIN-1-YL-6, 7-DIHYDRO-PYRROLO[2,3-D]PYRIMIDIN-5-YLIDENEMETHYL)-1H-PYRROLE-2-CARBOXYLIC ACID (2-MORPHOLIN-4-YL-ETHYL)-AMIDE (FORMULA 5)

To a mixture of 4-chloro-5,7-dihydro-pyrrolo[2,3-d]pyrimidin-6-one (85 mg, 0.5 mmol) and 5-formyl-1H-pyrrole-2-carboxylic acid (2-morpholin-4-yl-ethyl)-amide (125 mg, 0.5 mmol) in ethanol (4 mL) was added 0.2 mL of piperidine. The mixture was stirred at room temperature for 20 hours. The yellow precipitate was filtered after cooled with an ice bath, washed with cold ethanol and dried to give 114 mg (50.6%) of the title compound. $^1$H NMR (300 MHz, DMSO-d$_6$) δ 13.23 (br s, 1H, NH), 11.68 (br s, 1H, NH), 8.39 (m, 1H, CONHCH$_2$), 8.32 (s, 1H, H-vinyl), 7.11 (s, 1H), 6.91–6.98 (m, 2H), 3.56 (m, 4H, 2×CH$_2$), 3.38 (m, 6H, 3×CH), 2.39–2.47 (m, 6H, 3×CH$_2$), 1.65 (m, 6H, 3×CH$_2$). MS 452.2 [M$^+$+1].

5.6. Example 6

SYNTHESIS OF 5-[4-(1-BENZYL-1H-INDOL-5-YLAMINO)-6-OXO-6,7-DIHYDRO-PYRROLO[2,3-D]PYRIMIDIN-5-YLIDENEMETHYL]-4-METHYL-1H-PYRROLE-2-CARBOXYLIC ACID (2-MORPHOLIN-4-YL-ETHYL)-AMIDE HYDROCHLORIDE (FORMULA 6)

The title compound (8% yield) was prepared from 5-(4-chloro-6-oxo-6,7-dihydro-pyrrolo[2,3-d]pyrimidin-5-ylidenemethyl)-4-methyl-1H-pyrrole-2-carboxylic acid (2-morpholin-4-yl-ethyl)-amide and 1-benzyl-1H-indol-5-ylamine according to the procedure described for Example 12. $^1$H NMR (360 MHz, DMSO-d$_6$) δ 13.44 (br s, 1H, NH), 11.79 (br s, 1H, NH), 10.97 (br s, 1H, HCl), 9.28 (br s, 1H), 8.85 (br s, 1H, CONHCH$_2$), 8.25 (s, 1H, H-vinyl), 7.1–7.5 (m, 10H), 6.89 (br s, 1H), 6.43 (s, 1H), 5.40 (s, 2H), 3.96 (m, 2H, CH$_2$), 3.84 (m, 2H, CH$_2$), 3.68 (m, 2H, CH$_2$), 3.52 (m, 2H, CH$_2$), 3.29 (m, 2H, CH$_2$), 3.12 (m, 2H, CH$_2$), 2.53 (s, 3H, CH$_3$).

5.7. Example 7

SYNTHESIS OF 4-(3-CHLORO-4-FLUORO-PHENYLAMINO)-5-[3,5-DIMETHYL-4-(3-MORPHOLIN-4-YL-PROPYL)-1H-PYRROL-2-YLMETHYLENE]-5,7-DIHYDRO-PYRROLO[2,3-D]PYRIMIDIN-6-ONE HYDROCHLORIDE (FORMULA 7)

To a mixture of 4-chloro-5,7-dihydro-pyrrolo[2,3-d]pyrimidin-6-one (85 mg, 0.5 mmol) and 3,5-dimethyl-4-(3-morpholin-4-yl-propyl)-1H-pyrrole-2-carbaldehyde (125 mg, 0.5 mmol) in ethanol (4 mL) was added 0.1 to 0.2 mL of piperidine. The mixture was stirred at room temperature for 20 hours. The yellow precipitate was filtered after cooled with an ice bath, washed with cold ethanol, and dried to give 89 mg (45%) of 4-chloro-5-[3,5-dimethyl-4-(3-morpholin-4-yl-propyl)-1H-pyrrol-2-ylmethylene]-5,7-dihydro-pyrrolo[2,3-d]pyrimidin-6-one.

The title compound (10% yield) was prepared from 4-chloro-5-[3,5-dimethyl-4-(3-morpholin-4-yl-propyl)-1H-pyrrol-2-ylmethylene]-5,7-dihydro-pyrrolo[2,3-d]pyrimidin-6-one and 3-chloro-4-fluoro-phenylamine according to the procedure described for Example 12.

5.8. Example 8

SYNTHESIS OF 4-(3-CHLORO-4-FLUORO-PHENYLAMINO)-5-(5-METHYL-3H-IMIDAZOL-4-YLMETHYLENE)-5,7-DIHYDRO-PYRROLO[2.3-D]PYRIMIDIN-6-ONE (FORMULA 8)

4-Chloro-5,7-dihydro-pyrrolo[2,3-d]pyrimidin-6-one (1 eq.) was condensed with 5-methyl-3H-imidazole-4-carbaldehyde (1 eq.) at room temperature to give (76.9%) of 4-chloro-5-(5-methyl-3H-imidazol-4-ylmethylene)-5,7-dihydro-pyrrolo[2,3-d]pyrimidin-6-one.

The title compound (23% yield) was prepared from 4-chloro-5-(5-methyl-3H-imidazol-4-ylmethylene)-5,7-dihydro-pyrrolo[2,3-d]pyrimidin-6-one and 3-chloro-4-fluoro-phenylamine according to the procedure described for Example 12 without the conversion to the HCl salt. $^1$H NMR (360 MHz, DMSO-d$_6$) δ 13.45 (br s, 1H, NH), 11.76 (br s, 1H, NH), 9.19 (s, 1H), 8.31 (s, 1H, H-vinyl), 7.92 (s, 1H), 7.73 (m, 1H), 7.45 (m, 2H), 7.36 (m, 1H), 2.33 (s, 3H$_7$CH$_3$). MS 371.4 [M$^+$+1].

5.9. Example 9

SYNTHESIS OF 4-(3-CHLORO-4-FLUORO-PHENYLAMINO)-5-(3,5-DIMETHYL-1H-PYRROL-2-YLMETHYLENE)-5,7-DIHYDRO-PYRROLO[2,3-D]PYRIMIDIN-6-ONE (FORMULA 9)

4-Chloro-5,7-dihydro-pyrrolo[2,3-d]pyrimidin-6-one (1 eq.) was condensed with 3,5-dimethyl-1H-pyrrole-2-carbaldehyde (1 eq.) at room temperature to give (44.5%) of 4-chloro-5-(3,5-dimethyl-1H-pyrrol-2-ylmethylene)-5,7-dihydro-pyrrolo[2,3-d]pyrimidin-6-one.

The title compound (57% yield) was prepared from 4-chloro-5-(3,5-dimethyl-1H-pyrrol-2-ylmethylene)-5,7-dihydro-pyrrolo[2,3-d]pyrimidin-6-one and 3-chloro-4-fluoro-phenylamine according to the procedure described for Example 12 without the conversion to the HCl salt. $^1$H NMR (360 MHz, DMSO-d$_6$) δ 13.10 (br s, 1H, NH), 11.60 (br s, 1H, NH), 9.10 (s, 1H), 8.27 (s, 1H, H-vinyl), 7.70 (m, 1H), 7.3–7.4 (m, 3H), 6.04 (br s, 1H), 2.33 (s, 3H, CH$_3$), 2.16 (s, 3H, CH$_3$). MS 384.3 [M$^+$+1].

5.10. Example 10

SYNTHESIS OF 4-METHYL-5-[4-(4-METHYL-PIPERAZIN-1-YL)-6-OXO-6,7-DIHYDRO-PYRROLO[2,3-D]PYRIMIDIN-5-YLIDENEMETHYL]-1H-PYRROLE-2-CARBOXYLIC ACID (2-MORPHOLIN-4-YL-ETHYL)-AMIDE (FORMULA 10)

The title compound (47% yield) was prepared from 5-(4-chloro-6-oxo-6,7-dihydro-pyrrolo[2,3-d]pyrimidin-5-ylidenemethyl)-4-methyl-1H-pyrrole-2-carboxylic acid (2-morpholin-4-yl-ethyl)-amide and 1-methylpiperazine according to the procedure described for Example 14. $^1$H NMR (300 MHz, DMSO-d$_6$) δ 13.37 (br s, 1H, NH), 11.83 (br s, 1H, NH), 10.56 (v br s, 1H), 8.45 (v br s, 1H), 8.38 (s, 1H, H-vinyl), 7.09 (s, 1H), 6.87 (s, 1H), 3.4–3.6 (m, 10H, 5×CH$_2$), 2.85 (m, 4H, 2×CH$_2$), 2.4–2.6 (m, 6H, 3×CH$_2$), 2.49 (under DMSO, 3H, CH$_3$), 2.31 (s, 3H, CH$_3$). MS 481.3 [M$^+$+1].

5.11. Example 11

SYNTHESIS OF 5-(5-METHYL-3H-IMIDAZOL-4-YLMETHYLENE)-4-(4-METHYL-PIPERAZIN-1-YL)-5,7-DIHYDRO-PYRROLO[2,3-D]PYRIMIDIN-6-ONE (FORMULA 11)

The title compound (49% yield) was prepared from 4-chloro-5-(5-methyl-3H-imidazol-4-ylmethylene)-5,7-dihydro-pyrrolo[2,3-d]pyrimidin-6-one and 1-methylpiperazine according to the procedure described for Example 14. MS-EI 325 [M+].

5.12. Example 12

SYNTHESIS OF 5-[4-(1-BENZYL-1H-INDOL-5-YLAMINO)-6-OXO-6,7-DIHYDRO-PYRROLO[2,3-D]PYRIMIDIN-5-YLIDENEMETHYL]-1H-PYRROLE-2-CARBOXYLIC ACID (2-MORPHOLIN-4-YL-ETHYL)-AMIDE HYDROCHLORIDE (FORMULA 12)

A mixture of 5-(4-chloro-6-oxo-6,7-dihydro-pyrrolo[2,3-d]pyrimidin-5-ylidenemethyl)-1H-pyrrole-2-carboxylic acid (2-morpholin-4-yl-ethyl)-amide, 1-benzyl-1H-indol-5-ylamine and p-toluenesulfonic acid (5 mg) in 2 mL of 1-methyl-2-pyrrodinone and 2-methoxyethyl ether (1:3) was heated at 170–185° C. for 7 to 15 hours. The reaction mixture was evaporated to dryness and purified by reversed phase HPLC, then dissolved in 2N HCl and acetonitrile and freeze-dried to give 13.5 mg (42%) of the title compound. MS 589.3 [M++1].

5.13. Example 13

SYNTHESIS OF 5-(4-MORPHOLIN-4-YL-6-OXO-6,7-DIHYDRO-PYRROLO[2,3-D]PYRIMIDIN-5-YLIDENEMETHYL)-1H-PYRROLE-2-CARBOXYLIC ACID (2-MORPHOLIN-4-YL-ETHYL)-AMIDE (FORMULA 13)

The title compound (35% yield) was prepared from 5-(4-chloro-6-oxo-6,7-dihydro-pyrrolo[2,3-d]pyrimidin-5-ylidenemethyl)-1H-pyrrole-2-carboxylic acid (2-morpholin-4-yl-ethyl)-amide and morpholine according to the procedure described for Example 14. MS-EI 453 [M+].

5.14. Example 14

SYNTHESIS OF 5-(5-METHYL-3H-IMIDAZOL-4-YLMETHYLENE)-4-MORPHOLIN-4-YL-5,7-DIHYDRO-PYRROLO[2,3-D]PYRIMIDIN-6-ONE (FORMULA 14)

A mixture of 4-chloro-5-(5-methyl-3H-imidazol-4-ylmethylene)-5,7-dihydro-pyrrolo[2,3-d]pyrimidin-6-one (26 mg, 0.1 mmol) and morpholine (100 mg, 1.15 mmol) in ethanol (1.5 mL) was heated in a sealed tube at 10° C. for 3 hours. The reaction solution was evaporated to dryness and treated with cold ethanol. The yellow precipitate was filtered to give 22 mg (70.5%) of the title compound. MS-EI 312 [M+].

5.15. Example 15

SYNTHESIS OF 5-[4-(3-CHLORO-4-FLUORO-PHENYLAMINO)-6-OXO-6,7-DIHYDRO-PYRROLO[2,3-D]PYRIMIDIN-5-YLIDENEMETHYL]-1H-PYRROLE-2-CARBOXYLIC ACID (2-MORPHOLIN-4-YL-ETHYL)-AMIDE (FORMULA 15)

4-Chloro-5,7-dihydro-pyrrolo[2,3-d]pyrimidin-6-one (1 eq.) was condensed with 5-formyl-1H-pyrrole-2-carboxylic acid (2-morpholin-4-yl-ethyl)-amide (1 eq.) and triethylamine in ethanol at room temperature to give (92.5%) of 5-(4-chloro-6-oxo-6,7-dihydro-pyrrolo[2,3-d]pyrimidin-5-ylidenemethyl)-1H-pyrrole-2-carboxylic acid (2-morpholin-4-yl-ethyl)-amide.

The title compound (16% yield) was prepared from 5-(4-chloro-6-oxo-6,7-dihydro-pyrrolo[2,3-d]pyrimidin-5-ylidenemethyl)-1H-pyrrole-2-carboxylic acid (2-morpholin-4-yl-ethyl)-amide and 3-chloro-4-fluoro-phenylamine according to the procedure described for Example 12 without the conversion to HCl salt. MS 512.3 [M+1].

5.16. Example 16

SYNTHESIS OF 5-[4-(3-ETHYNYL-PHENYLAMINO)-6-OXO-6,7-DIHYDRO-PYRROLO[2,3-D]PYRIMIDIN-5-YLIDENEMETHYL]-1H-PYRROLE-2-CARBOXYLIC ACID (2-MORPHOLIN-4-YL-ETHYL)-AMIDE HYDROCHLORIDE (FORMULA 16)

The title compound (20% yield) was prepared from 5-(4-chloro-6-oxo-6,7-dihydro-pyrrolo[2,3-d]pyrimidin-5-ylidenemethyl)-1H-pyrrole-2-carboxylic acid (2-morpholin-4-yl-ethyl)-amide and 3-ethynylaniline according to the procedure described for Example 12. MS 484.3 [M++1].

5.17. Example 17

SYNTHESIS OF 5-[4-(3-ETHYNYL-PHENYLAMINO)-6-OXO-6,7-DIHYDRO-PYRROLO[2,3-D]PYRIMIDIN-5-YLIDENEMETHYL]-4-METHYL-1H-PYRROLE-2-CARBOXYLIC ACID (2-MORPHOLIN-4-YL-ETHYL)-AMIDE (FORMULA 17)

The title compound (15% yield) was prepared from 5-(4-chloro-6-oxo-6,7-dihydro-pyrrolo[2,3-d]pyrimidin-5-ylidenemethyl)-4-methyl-1H-pyrrole-2-carboxylic acid (2-morpholin-4-yl-ethyl)-amide and 3-ethynylaniline according to the procedure described for Example 12 without the conversion to HCl salt. MS 498.2 [M++1].

5.18. Example 18

SYNTHESIS OF 5-[3,5-DIMETHYL-4-(3-MORPHOLIN-4-YL-PROPYL)-1H-PYRROL-2-YLMETHYLENE]-4-(3-ETHYNYL-PHENYLAMINO)-5,7-DIHYDRO-PYRROLO[2,3-D]PYRIMIDIN-6-ONE (FORMULA 18)

The title compound (7% yield) was prepared from 4-chloro-5-[3,5-dimethyl-4-(3-morpholin-4-yl-propyl)-1H-pyrrol-2-ylmethylene]-5,7-dihydro-pyrrolo[2,3-d]pyrimidin-6-one and 3-ethynylaniline according to the procedure described for Example 12 without the conversion to HCl salt. MS 483.3 [M++1].

5.19. Example 19

SYNTHESIS OF 3-{5-[4-(3-CHLORO-4-FLUORO-PHENYLAMINO)-6-OXO-6,7-DIHYDRO-PYRROLO[2,3-D]PYRIMIDIN-5-YLIDENEMETHYL]-2,4-DIMETHYL-1H-PYRROL-3-YL}-PROPIONIC ACID (FORMULA 19)

To a solution of 4-chloro-7H-pyrrolo[2,3-d]pyrimidine (767.9 mg, 5 mmol) and 3-chloro-4-fluoro-phenylamine (873.4 mg, 6 mmol) in 25 mL of dry DMF under nitrogen was added silver trifluoromethanesulfonate (1.54 g, 6 mmol). The mixture was stirred at 95° C. for 15 hours. The cooled reaction was diluted with ethyl acetate (70 mL) and filtered through celite, washed thoroughly with ethyl acetate. The filtrate was washed with brine (5×). The brine was extracted with ethyl acetate which was then washed with brine. The combined ethyl acetate was dried (magnesium sulfate), concentrated and purified to give 1.22 g (93%) of (3-chloro-4-fluoro-phenyl)-(7H-pyrrolo[2,3-d]pyrimidin-4-yl)-amine as an off-white solid. m.p. 274–275° C. $^1$H NMR (360 MHz, DMSO-d$_6$) δ 11.78 (br s, 1H, NH), 9.41 (s, 1H), 8.31 (s, 1H), 8.28 (m, 1H), 7.79 (m, 1H), 7.37 (t, 1H), 7.25 (m, 1H), 6.76 (m, 1H). MS 263.4 [M$^+$+1].

To a stirred solution of (3-chloro-4-fluoro-phenyl)-(7H-pyrrolo[2,3-d]pyrimidin-4-yl)-amine (26.3 mg, 0.1 mmol) in one mL of t-butanol was added portionwise 64 mg (0.2 mmol) of pyridinium bromide perbromide (PBPB). The reaction mixture was stirred at room temperature for 4 hours. The reaction was diluted with ethyl acetate, washed with water, aqueous sodium sulfate, brine, dried and concentrated to give 5,5-dibromo-4-(3-chloro-4-fluoro-phenylamino)-5,7-dihydro-pyrrolo[2,3-d]pyrimidin-6-one (used in the next step without any purification).

A mixture of 5,5-dibromo-4-(3-chloro-4-fluoro-phenylamino)-5,7-dihydro-pyrrolo[2,3-d]pyrimidin-6-one (from above), zinc dust in 2 mL of acetic acid was stirred at room temperature for one hour. The reaction was diluted with ethyl acetate and filtered. The filtrate was washed with water, sodium bicarbonate and brine, dried, concentrated and purified to give 11.2 mg (combined yield of 40% for the 2 steps) of 4-(3-chloro-4-fluoro-phenylamino)-5,7-dihydro-pyrrolo[2,3-d]pyrimidin-6-one as an off-white solid. $^1$H NMR (300 MHz, DMSO-d$_6$) δ 11.08 (br s, 1H, NH), 9.02 (s, 1H), 8.33 (s, 1H), 8.02 (m, 1H), 7.58 (m, 1H), 7.35 (t, 1H), 3.45 (s, 2H, CH$_2$). MS 279.3 [M$^+$1].

A mixture of 4-(3-chloro-4-fluoro-phenylamino)-5,7-dihydro-pyrrolo[2,3-d]pyrimidin-6-one (6.3 mg, 0.0226 mmol), 3-(5-formyl-2,4-dimethyl-1H-pyrrol-3-yl)-propionic acid (4.9 mg, 0.0249 mmol) and piperidine (4 drops) in ethanol (1 mL) was stirred at room temperature for 24 hours. The reaction was concentrated and purified (reversed phase HPLC) to give 5.2 mg (51%) of the title compound. MS 456.4 [M$^+$+1].

5.20. Example 20

SYNTHESIS OF 4-(3-CHLORO-4-FLUORO-PHENYLAMINO)-7-METHYL-5,7-DIHYDRO-PYRROLO[2,3-D]PYRIMIDIN-6-ONE

In this specific method of the invention, the title compound is prepared according to Scheme 5:

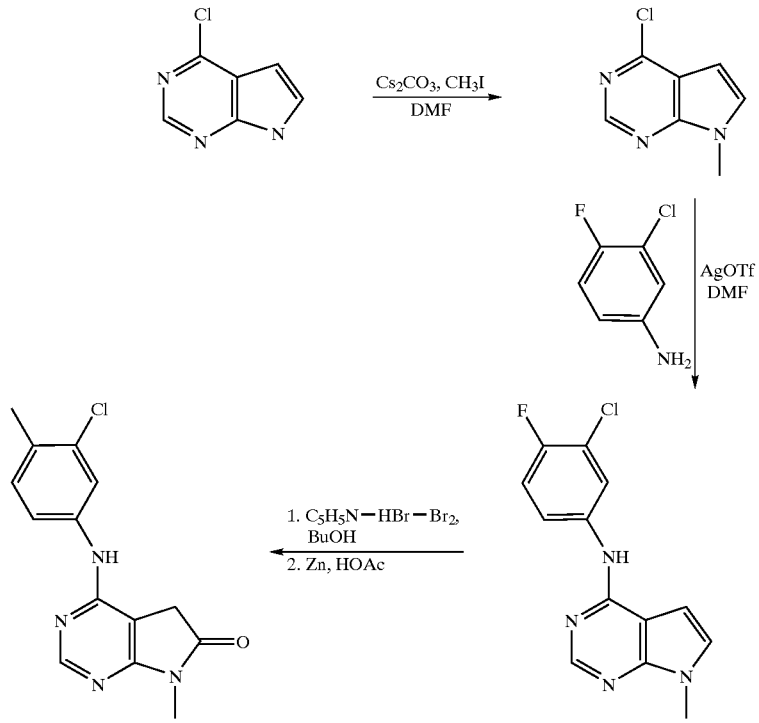

Scheme 5

According to Scheme 5, cesium carbonate (968 mg, 3 mmol) followed by methyl iodide (1 g, 7.1 mmol) was added to a solution of 4-chloro-7H-pyrrolo[2,3-d]pyrimidine (121 mg, 0.79 mmol) in DMF (5 mL). The mixture was stirred at room temperature for 6 hours. The reaction was poured into water and extracted with ethyl acetate. The organic layer was washed with brine, dried, concentrated and column chromatographed to give 116 mg (88%) of 4-chloro-7-methyl-7H-pyrrolo[2,3-d]pyrimidine as a white solid. $^1$H NMR (360 MHz, DMSO-d$_6$) 8.62 (s, 1H), 7.71 (s, 1H), 6.62 (s, 1H), 3.84 (s, 3H, CH$_3$).

A mixture of 4-chloro-7-methyl-7H-pyrrolo[2,3-d]pyrimidine (398.8 mg, 2.4 mmol) and 3-chloro-4-fluoro-phenylamine (378 mg, 2.6 mmol) in DMF (6 mL) was stirred at room temperature for 2 minutes. To it was added silver triflate (672 mg, 2.6 mmol), the mixture was then stirred at 90° C. for 2 hours. The reaction was then diluted with ethyl acetate and filtered off the precipitate, washing the precipitate with 10% ammonia solution. The filtrate was extracted with ethyl acetate, dried and concentrated. The residue was triturated with ethyl acetate and filtered to give 549.1 mg,(83%) of(3-chloro-4-fluoro-phenyl)-(7-methyl-7H-pyrrolo[2,3-d]pyrimidin-4-yl)-amine as an off-white solid. $^1$H NMR (300 MHz, DMSO-$d_6$) 9.48 (s, 1H, NH), 8.35 (s, 1H), 8.29 (dd, J=2.7 & 6.8 Hz, 1H), 7.75–7.80 (m, 1H), 7.37 (t, J=9.3 Hz, 1H), 7.30 (d, J=3.1 Hz, 1H), 6.77 (d, J=3.1 Hz, 1H), 3.75 (s, 3H, CH$_3$). MS 277 [M$^+$1].

PBPB (2.8 g, 7.8 mmol) was added portionwise to the (3-chloro-4-fluoro-phenyl)-(7-methyl-7H-pyrrolo[2,3-d]pyrimidin-4-yl)-amine (1.08 g, 3.9 mmol) suspended in tert-butanol (20 mL) and acetic acid (10 mL). After stirring at room temperature for 18 hours, to the mixture was added zinc dust (760 mg, 11.7 mmol) portionwise and stirring was continued for overnight. The precipitate was filtered off and the filtrate was concentrated. The residue was triturated with little water and the precipitate was collected by vacuum filtration, washed with little ethyl acetate and dried to give 1.12 g (98%) of 4-(3-chloro-4-fluoro-phenylamino)-7-methyl-5,7-dihydro-pyrrolo[2,3-d]pyrimidin-6-one as a tan colored solid. $^1$H NMR (DMSO-$d_6$) 9.07 (s, 1H, NH), 8.42 (s, 1H), 8.01 (d, J=2.6 & 7.2 Hz, 1H), 7.56 (m, 1H), 7.34 (t, J=9.1 Hz, 1H), 3.48 (s, 2H, CH$_2$), 3.07 (s, 3H, CH$_3$).

5.21. Example 21

SYNTHESIS OF 4-(3-CHLORO-4-FLUORO-PHENYLAMINO)-5-[3,5-DIMETHYL-4-(3-OXO-3-PYRROLIDIN-1-YL-PROPYL)-1H-PYRROL-2-YLMETHYLENE]-5,7-DIHYDRO-PYRROLO[2,3-D]PYRIMIDIN-6-ONE (FORMULA 24)

A mixture of 4-(3-chloro-4-fluoro-phenylamino)-5,7-dihydro-pyrrolo[2,3-d]pyrimidin-6-one (70 mg, 0.25 mmol), 3,5-dimethyl-4-(3-oxo-3-pyrrolidin-1-yl-propyl)-1H-pyrrole-2-carbaldehyde (64.6 mg, 0.26 mmol) and piperidine (3 drops) in ethanol was stirred at room temperature under nitrogen for 2 days. The precipitate was collected by vacuum filtration, washed with ethanol and dried to give 65 mg (51%) of the title compound. $^1$H NMR (300 MHz, DMSO-$d_6$) δ 13.18 (br s, 1H, NH), 11.61 (br s, 1H, NH), 9.13 (brs, 1H), 8.26 (s, 1H), 7.70 (dd, J=2.4 & 6.9 Hz, 1H), 7.31–7.42 (m, 3H), 3.25 (m, 4H, 2×CH$_2$), 2.63 (t, J=7.5 Hz, 2H, CH$_2$), 2.35 (m, 2H, CH$_2$), 2.31 (s, 3H, CH$_3$), 2.12 (s, 3H, CH$_3$), 1.76 (m, 4H, 2×CH$_2$). MS 509 [M$^+$+1].

5.22. Example 22

SYNTHESIS OF 4-(3-CHLORO-4-FLUORO-PHENYLAMINO)-5-{3-METHYL-5-[3-(4-METHYL-PIPERAZIN-1-YL)-3-OXO-PROPYL]-1H-PYRROL-2-YLMETHYLENE}-5,7-DIHYDRO-PYRROLO[2,3-D]PYRIMIDIN-6-ONE (FORMULA 25)

To a solution of 3-(5-formyl-4-methyl-1H-pyrrol-2-yl)-propionic acid (271.8 mg, 1.5 mmol) in DMF (4 mL) was added HOBt (243.2 mg, 1.8 mmol), EDC (345.1 mg, 1.8 mmol) and then 1-methylpiperazine (0.2 mL, 1.8 mmol). The mixture was stirred at room temperature under nitrogen for overnight. The reaction was poured into sat. sodium bicarbonate (50 mL) and extracted with ethyl acetate. The combined organic layer was dried, concentrated and column chromatographed (MeOH/DCM) to give 325.2 mg (82%) of 3-methyl-5-[3-(4-methyl-piperazin-1-yl)-3-oxo-propyl]-1H-pyrrole-2-carbaldehyde as a white solid.

A mixture of 4-(3-chloro-4-fluoro-phenylamino)-5,7-dihydro-pyrrolo[2,3-d]pyrimidin-6-one (70 mg, 0.25 mmol), 3-methyl-5-[3-(4-methyl-piperazin-1-yl)-3-oxo-propyl]-1H-pyrrole-2-carbaldehyde (79 mg, 0.3 mmol) and piperidine (3 drops) in ethanol (2 mL) was stirred in an oil bath at 65° C. for 2 hours. The reaction was cooled at room temperature for overnight. The precipitate was collected by vacuum filtration, washed with ethanol (5×) and dried to give 88.9 mg (68%) of the title compound. $^1$H NMR (360 MHz, DMSO-$d_6$) δ 13.15 (s, 1H, NH), 11.55 (br s, 1H, NH), 9.08 (s, 1H), 8.27 (s, 1H), 7.69 (dd, J=2.5 & 6.9 Hz, 1H), 7.30–7.40 (m, 3H), 6.08 (d, J=2.23 Hz, 1H), 3.43 (m, 4H, 2×CH$_2$), 2.89 (t, J=7.4 Hz, 2H, CH$_2$), 2.68 (t, J=7.4 Hz, 2H, CH$_2$), 2.24 (m, 4H, 2×CH$_2$), 2.16 (s, 6H, 2×CH$_3$). MS 524 [M$^+$+1].

5.23 Example 23

SYNTHESIS OF 4-(3-CHLORO-4-FLUORO-PHENYLAMINO)-5-[3-METHYL-5-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 26)

To a suspension of 5-formyl-4-methyl-1H-pyrrole-2-carboxylic acid (4 g, 26 mmol) in DMF (80 mL) was added morpholine (1.9 mL, 31 mmol), followed by EDAC (5.9 g, 31 mmol), HOBt (4.2 g, 31 mmol) and triethylamine (8 mL, 62 mmol). The reaction mixture was stirred at room temperature for 2 days. The precipitate was filtered off, washing with hexane and the filtrate was then concentrated, diluted with water and extracted with ethyl acetate (2×100 mL). The aqueous layer was adjusted to pH=9 using sodium carbonate and extracted again. The combined organic layer was concentrated and re-suspended in ethyl acetate. The resulting precipitate was collected by vacuum filtration to give 3 g of solid. The filtrate was purified by column chromatographed to give 1.2 g of the solid. Total yield collected was 4.2 g (73%) of 3-methyl-5-(morpholine-4-carbonyl)-1H-pyrrole-2-carbaldehyde as a light yellow solid. $^1$H NMR (30 MHz, DMSO-$d_6$) δ 12.24 (br s, 1H, NH), 9.71 (s, 1H, CHO), 6.39 (5, 1H), 3.59 (br s, 8H, 4×CH$_2$), 2.29 (s, 3H, CH$_3$).

A mixture of 4-(3-chloro-4-fluoro-phenylamino)-5,7-dihydro-pyrrolo[2,3-d]pyrimidin-6-one (93 mg, 0.33 mmol), 3-methyl-5-(morpholine-4-carbonyl)-1H-pyrrole-2-carbaldehyde (73 mg, 0.33 mmol), and piperidine (1 drop) in ethanol (2 mL) was stirred at room temperature for 3 days. The precipitate was collected by vacuum filtration, washed with ethanol and dried to give 110.3 mg (69%) of the title compound. $^1$H NMR (360 MHz, DMSO-$d_6$) δ 13.43 (br s, 1H, NH), 11.74 (br s, 1H, NH), 9.23 (br s, 1H), 8.33 (s, 1H), 7.73 (dd, J=2.5 & 6.7 Hz, 1H), 7.44 (m, 1H), 7.32–7.37 (m, 2H), 6.61 (d, J=2.28 Hz, 1H), 3.69 (m, 4H, 2×CH$_2$), 3.65 (m, 4H, 2×CH$_2$), 2.22 (s, 3H, CH$_3$). MS 483 [M$^+$].

5.24. Example 24

SYNTHESIS OF 3-{2-[4-(3-CHLORO-4-FLUORO-PHENYLAMINO)-6-OXO-6,7-DIHYDRO-PYRROLO[2,3-D]PYRIMIDIN-5-YLIDENEMETHYL]-5-ISOPROPYL-1H-PYRROL-3-YL}-PROPIONIC ACID (FORMULA 27)

A mixture of 4-(3-chloro-4-fluoro-phenylamino)-5,7-dihydro-pyrrolo[2,3-d]pyrimidin-6-one (70 mg, 0.25 mmol), 3-(2-formyl-5-isopropyl-1H-pyrrol-3-yl)-propionic acid (54.4 mg, 0.26 mmol) and piperidine (3 drops) in ethanol (2 mL) was stirred at room temperature for 2 days. The precipitate was collected by vacuum filtration, washed with water, 1N HCl, water and finally ethanol, dried in vacuum oven to give 83 mg (71%) of the title compound. $^1$H NMR (300 MHz, DMSO-$d_6$) δ 13.44 (br s, 1H, NH), 12.15 (br s, 1H, COOH), 11.69 (br s, 1H, NH), 9.02 (br s, 1H), 8.29 (s, 1H), 7.77 (dd, J=2.5 & 6.4 Hz, 1H), 7.47 (s, 1H), 7.43 (m, 1H), 7.33 (t, J=8.9 Hz, 1H), 6.14 (d, J=2 Hz, 1H), 3.01 (m, 1H, CH(CH$_3$)$_2$), 2.83 (t, J=7.2 Hz, 2H, CH$_2$), 2.48 (m, 2H, CH$_2$), 1.21.27 (d, J=6.8 Hz, 6H, CH(CH$_3$)$_2$). MS 469 [M$^+$+1].

5.25 Example 25

SYNTHESIS OF 5-[4-(3-CHLORO-4-FLUORO-PHENYLAMINO)-6-OXO-6,7-DIHYDRO-PYRROLO[2,3-D]PYRIMIDIN-5-YLIDENEMETHYL]-2,4-DIMETHYL-1H-PYRROLE-3-CARBOXYLIC ACID (2-DIETHYLAMINO-ETHYL)-AMIDE (FORMULA 28)

A mixture of 4-(3-chloro-4-fluoro-phenylamino)-5,7-dihydro-pyrrolo[2,3-d]pyrimidin-6-one (66 mg, 0.24 mmol), 5-formyl-2,4-dimethyl-1H-pyrrole-3-carboxylic acid (2-diethylamino-ethyl)-amide (63.7 mg, 0.24 mmol) and piperidine (1 drop) in ethanol (2 mL) was stirred at room temperature for 3 days. The precipitate was collected by vacuum filtration, washed with ethanol and dried to give 78.5 mg (62%) of the title compound. $^1$H NMR (360 MHz, DMSO-$d_6$) δ 13.33 (br s, 1H, NH), 11.61 (br s, 1H, NH), 9.17 (br s, 1H), 8.29 (s, 1H), 7.69 (dd, J=2.5 & 6.5 Hz, 1H), 7.35 (m, 4H), 3.29 (m, 2H, CH$_2$), 2.5 (m, 6H, N(CH$_2$CH$_3$)$_2$ & CH$_2$), 2.45 (s, 3H, CH$_3$), 2.25 (s, 3H, CH$_3$), 0.96 (t, J=7 Hz, 6H, N(CH$_2$CH$_3$)$_2$). MS 526 [M$^+$+1].

5.26. Example 26

SYNTHESIS OF 4-(3-CHLORO-4-FLUORO-PHENYLAMINO)-5-[3-METHYL-4-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 29)

A mixture of 4-(3-chloro-4-fluoro-phenylamino)-5,7-dihydro-pyrrolo[2,3-d]pyrimidin-6-one (70 mg, 0.25 mmol), 3-methyl-4-(4-methyl-piperazine-1-carbonyl)-1H-pyrrole-2-carbaldehyde (70.7 mg, 0.3 mmol) and piperidine (3 drops) in ethanol (2 mL) was stirred at room temperature for 4 days. The precipitate was collected by vacuum filtration, washed with ethanol to give 63 mg (51%) of the title compound as a yellow solid. $^1$H NMR (360 MHz, DMSO-$d_6$) δ 13.29 (br s, 1H, NH), 11.73 (br s, 1H, NH), 9.16 (br s, 1H), 8.31 (s, 1H), 7.72 (dd, J=2.7 & 6.5 Hz, 1H), 7.46 (d, J=2.7 Hz, 1H), 7.43 (m, 1H), 7.40 (s, 1H), 7.34 (t, J=9.05 Hz, 1H), 3.49 (m, 4H, 2×CH$_2$), 2.29 (m, 4H, 2×CH$_2$), 2.19 (s, 3H, CH$_3$), 2.18 (s, 3H, CH$_3$). MS 496 [M$^+$+1].

5.27. Example 27

SYNTHESIS OF 4-(3-CHLORO-4-FLUORO-PHENYLAMINO)-5-[3,5-DIMETHYL-4-(3-MORPHOLIN-4-YL-3-OXO-PROPYL)-1H-PYRROL-2-YLMETHYLENE]-5,7-DIHYDRO-PYRROLO[2,3-D]PYRIMIDIN-6-ONE (FORMULA 30)

A mixture of 4-(3-chloro-4-fluoro-phenylamino)-5,7-dihydro-pyrrolo[2,3-d]pyrimidin-6-one (86 mg, 0.31 mmol), 3,5-dimethyl-4-(3-morpholin-4-yl-3-oxo-propyl)-1H-pyrrole-2-carbaldehyde (83 mg, 0.31 mmol) and piperidine (1 drop) in ethanol (2 mL) was stirred at room temperature for 3 days. The precipitate was collected by vacuum filtration, washed with ethanol and dried to give the title compound. MS 525 [M$^+$+1].

5.28. Example 28

SYNTHESIS OF 4-(3-CHLORO-4-FLUORO-PHENYLAMINO)-5-[3-METHYL-4-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 31)

A mixture of 4-(3-chloro-4-fluoro-phenylamino)-5,7-dihydro-pyrrolo[2,3-d]pyrimidin-6-one (70 mg, 0.25 mmol), 3-methyl-4-(morpholine-4-carbonyl)-1H-pyrrole-2-carbaldehyde (66.7 mg, 0.3 mmol) and piperidine (3 drops) in ethanol (2 mL) was stirred at room temperature for 4 days. The precipitate was collected by vacuum filtration, washed with ethanol and dried to give 39 mg (32%) of the title compound. $^1$H NMR (360 MHz, DMSO-$d_6$) δ 13.30 (br s, 1H, NH), 11.69 (br s, 1H, NH), 9.16 (br s, 1H), 8.31 (s, 1H), 7.72 (dd, J=2.8 & 6.7 Hz, 1H), 7.46 (d, J=2.8 Hz, 1H), 7.43 (m, 1H), 7.41 (s, 1H), 7.35 (t, J=9 Hz, 1H), 3.59 (m, 4H, 2×CH$_2$), 3.51 (m, 4H, 2×CH$_2$), 2.21 (s, 3H, CH$_2$). MS 483 [M$^+$+1].

5.29. Example 29

SYNTHESIS OF 5-[4-(3-CHLORO-4-FLUORO-PHENYLAMINO)-7-METHYL-6-OXO-6,7-DIHYDRO-PYRROLO[2,3-D]PYRIMIDIN-5-YLIDENEMETHYL]-4-METHYL-1H-PYRROLE-2-CARBOXYLIC ACID (2-MORPHOLIN-4-YL-ETHYL)-AMIDE (FORMULA 32)

A mixture of 4-(3-chloro-4-fluoro-phenylamino)-7-methyl-5,7-dihydro-pyrrolo[2,3-d]pyrimidin-6-one (244 mg, 0.83 mmol), 5-formyl-4-methyl-1H-pyrrole-2-carboxylic acid (2-morpholin-4-yl-ethyl)-amide (1.2 equiv.) and piperidine (1 drop) in ethanol and DMF (2 mL) was stirred at 90° C. for 2 hours. The reaction was diluted with water and the precipitate was collected by vacuum filtration, washed with water, ethyl acetate and hexane and dried to give 138.5 mg (31%) of the title compound. $^1$H NMR (300 MHz, DMSO-$d_6$) δ 13.39 (br s, 1H, NH), 9.29 (br s, 1H), 8.38 (m, 2H), 7.72 (m 1H), 7.39 (s, 1H, H-vinyl), 7.34 (m, 2H), 6.81 (s, 1H), 3.56 (m, 4H, 2×CH$_2$), 3.35 (m, 2H, CH$_2$), 3.31 (s, 3H, CH$_3$), 2.45 (m, 2H, CH$_2$), 2.41 (m, 4H, 2×CH$_2$), 2.20 (s, 3H, CH$_3$). MS 540 [M$^+$1].

5.30. Example 30

SYNTHESIS OF 4-(3-CHLORO-4-FLUORO-PHENYLAMINO)-5-[5-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 33)

A mixture of 4-(3-chloro 4-fluoro-phenylamino)-5,7-dihydro-pyrrolo[2,3-d]pyrimidin-6-one (70 mg, 0.25 mmol), 5-(morpholine-4-carbonyl)-1H-pyrrole-2-carbaldehyde (62.5 mg, 0.3 mmol) and piperidine (3 drops) in ethanol (2 mL) was stirred at room temperature for 4 days. The precipitate was collected by vacuum filtration, washed with ethanol and dried to give 69 mg (59%) of the title compound. $^1$H NMR (360 MHz, DMSO-$d_6$) δ 13.41 (br s, 1H, NH), 11.65 (br s, 1H, NH), 8.81 (br s, 1H, NH), 8.28 (s, 1H), 7.76 (s, 1H), 7.75 (m, 1H), 7.53 (m, 1H), 7.38 (t, J=9.05. Hz, 1H), 6.91 (d, J=3.6 Hz, 1H), 6.76 (d, J=3.6 Hz, 1H), 3.71 (m, 4H, 2×CH$_2$), 3.65 (m, 4H, 2×CH$_2$). MS 469 [M$^+$+1].

5.31. Example 31

SYNTHESIS OF 4-(3-CHLORO-4-FLUORO-PHENYLAMINO)-7-METHYL-5-[3-METHYL-5-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 34)

A mixture of 4-(3-chloro-4-fluoro-phenylamino)-7-methyl-5,7-dihydro-pyrrolo[2,3-d]pyrimidin-6-one (116 mg, 0.4 mmol), 3-methyl-5-(morpholine-4-carbonyl)-1H-pyrrole-2-carbaldehyde (130 mg) and piperidine (1 drop) in ethanol (2 mL) was stirred at 90° C. for 2 hours. The reaction was diluted with water and the precipitate was collected by vacuum filtration, washed with water, ethyl acetate and hexane and dried to give 141 mg (74%) of the title compound. $^1$H NMR (300 MHz, DMSO-d$_6$) δ 13.42 (br s, 1H, NH), 9.29 (br s, 1H), 8.38 (s, 1H), 7.72 (m, 1H), 7.34–7.41 (m, 3H), 6.6 (s, 1H), 3.67 (m, 4H, 2×CH$_2$), 3.65 (m, 4H, 2×CH$_2$), 3.29 (s, 3H, CH$_3$), 2.20 (s, 3H, CH$_3$). MS 497 [M$^+$+1].

5.32. Example 32

SYNTHESIS OF 4-(3-CHLORO-4-FLUORO-PHENYLAMINO)-5-[4-METHYL-5-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 35)

Acetic acid (360 mL) and water (300 ml) was added to a solution of ethyl 3,5-dimethyl-2-pyrrolecarboxylate (5 g, 29.9 mmol) in THF (300 ML). The mixture was cooled to −10 to −5° C. for 30 minutes. To the mixture was then added ceric ammonium nitrate (CAN, 67.21 g, 122.6 mmol) over a period of 30 minutes. The mixture was stirred at −10 to −5° C. for 1.5 hours. The reaction was diluted with water (800 mL) and extracted with dichloromethane (3×). The combined extracts were washed with sodium bicarbonate solution until the aqueous layer was basic, dried and concentrated. The residue was purified on a silica gel column (10% EtOAc in hexane) to give 2.4 g (44%) of 5-formyl-3-methyl-1H-pyrrole-2-carboxylic acid ethyl ester as a white solid. $^1$H NMR (300 MHz, DMSO-d$_6$) δ 12.61 (br s, 1H, NH), 9.64 (s, 1H, CHO), 6.78 (s, 1H), 4.27 (q, J=7.17 Hz, 2H, OCH$_2$CH$_3$), 2.26 (s, 3H, CH$_3$), 1.30 (t, J=7.17 Hz, 3H, OCH$_2$CH$_3$). MS 182 [M$^+$+1].

Lithium hydroxide (8.73 g, 36.44 mmol) was added to the 5-formyl-3-methyl-1H-pyrrole-2-carboxylic acid ethyl ester (1.32 g, 7.27 mmol) in methanol (27 mL) and water (9 mL). The mixture was stirred at room temperature for over the weekend. The reaction was diluted with water (10 mL), evaporated most of the methanol and washed with ether. The aqueous layer was acidified with 1N HCl (37 mL) to pH=2, extracted with ethyl acetate. Washed with brine, dried and concentrated. The residue was washed with dichloromethane and filtered to give 0.98 g (88%) of 5-formyl-3-methyl-1H-pyrrole-2-carboxylic acid as a tan solid. $^1$H NMR (360 MHz, DMSO-d$_6$) δ 12.87 (br s, 1H, COOH), 12.41 (br s, 1H, NH), 9.63 (s, 1H, CHO), 6.74 (s, 1H), 2.26 (s, 3H, CH$_3$).

To a solution of 5-formyl-3-methyl-1H-pyrrole-2-carboxylic acid (306.3 mg, 2 mmol) in DMF 5 mL was added HOBt (324.3 mg, 2.4 mmol), EDC (460.1 mg, 2.4 mmol) and then 1-methylpiperazine (0.27 mL, 2.4 mmol). The mixture was stirred at room temperature under nitrogen for overnight. The reaction was diluted with ethyl acetate and washed with sodium bicarbonate. The aqueous layer was extracted several times with ethyl acetate. The combined organic layer was washed with brine, dried, concentrated and column chromatographed (MeOH/DCM) to give 310 mg (66%) of 4-methyl-5-(4-methyl-piperazine-1-carbonyl)-1H-pyrrole-2-carbaldehyde as a light yellow foam solid. $^1$H NMR (360 MHz, DMSO-d$_6$) 12.20 (br s, 1H, NH), 9.47 (s, 1H, CHO), 6.80 (s, 1H), 3.58 (m, 4H, 2×CH$_2$), 3.44 (m, 4H, 2×CH$_2$), 2.03 (s, 3H, CH$_3$).

A mixture of 4-(3-chloro-4-fluoro-phenylamino)-5,7-dihydro-pyrrolo[2,3-d]pyrimidin-6-one (70 mg, 0.25 mmol), 4-methyl-5-(4-methyl-piperazine-1-carbonyl)-1H-pyrrole-2-carbaldehyde (70.6 mg, 0.3 mmol) and piperidine (3 drops) in ethanol (2 mL) was stirred at room temperature for 4 days. The precipitate was collected by vacuum filtration, washed with ethanol and dried to give 89.1 mg (72%) of the title compound. $^1$H NMR (360 MHz, DMSO-d$_6$) δ 13.13 (br s, 1H, NH), 11.74 (br s, 1H, NH), 8.77 (br s, 1H, NH), 8.27 (s, 1H), 7.75 (dd, J=2.7 & 6.5 Hz, 1H), 7.71 (s, 1H), 7.52 (m, 1H), 7.38 (t, J=8.85 Hz, 1H), 6.74 (s, 1H), 3.52 (m, 4H, 2×CH$_2$), 2.37 (m, 4H, 2×CH$_2$), 2.21 (s, 3H, CH$_3$), 2.14 (s, 3H, CH$_3$). MS 496 [M$^+$+1].

5.33. Example 33

SYNTHESIS OF 4-(3-CHLORO-4-FLUORO-PHENYLAMINO)-7-METHYL-5-[3-METHYL-5-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 36)

A mixture of 4-(3-chloro-4-fluoro-phenylamino)-7-methyl-5,7-dihydro-pyrrolo[2,3-d]pyrimidin-6-one (80 mg, 0.27 mmol), 3-methyl-5-(4-methyl-piperazine-1-carbonyl)-1H-pyrrole-2-carbaldehyde (1.2 equiv.) and piperidine (1 drop) in ethanol (2 mL) was stirred at 90° C. for 2 hours. The reaction was diluted with water and the precipitate was collected by vacuum filtration, washed with water, ethyl acetate and hexane and dried to give 120.5 mg (72%) of the title compound. $^1$H NMR (300 MHz, DMSO-d$_6$) δ 13.42 (br s, 1H, NH), 9.32 (brs, 1H), 8.40 (s, 1H), 7.71 (m, 1H), 7.35–7.41 (m, 3H), 6.60 (s, 1H), 3.69 (m, 14H, 2×CH$_2$), 3.30 (s, 3H, CH$_3$), 2.35 (m, 4H, 2×CH$_2$), 2.21 (s, 3H, CH$_3$), 2.20 (s, 3H, CH$_3$). MS 510 [M$^+$+1].

5.34. Example 34

SYNTHESIS OF 4-(3-CHLORO-4-FLUORO-PHENYLAMINO)-5-[4-METHYL-5-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 37)

To a solution of 5-formyl-3-methyl-1H-pyrrole-2-carboxylic acid (306.3 mg, 2 mmol) in DMF (5 mL) was added HOBt (324.3 mg, 2.4 mmol), EDC (460.1 mg, 2.4 mmol) and then morpholine (0.21 mL, 2.4 mmol). The mixture was stirred at room temperature under nitrogen for overnight. The reaction was diluted with ethyl acetate and washed with sodium bicarbonate. The aqueous layer was extracted several times with ethyl acetate. The combined organic layer was washed with brine, dried, concentrated and column chromatographed (MeOH/DCM) to give 395 mg (89%) of 4-methyl-5-(morpholine-4-carbonyl)-1H-pyrrole-2-carbaldehyde as a light yellow foam solid. $^1$H NMR (360 MHz, DMSO-$d_6$) δ 12.18 (br s, 1H, NH), 9.46 (s, 1H, CHO), 6.79 (s, 1H), 3.43 (m, 4H, 2×CH$_2$), 2.29 (m, 4H, 2×CH$_2$), 2.17 (s, 3H, CH$_3$), 2.01 (s, 3H, CH$_3$).

A mixture of 4-(3-chloro-4-fluoro-phenylamino)-5,7-dihydro-pyrrol[2,3-d]pyrimidin-6-one (70 mg, 0.25 mmol), 4-methyl-5-(morpholine-4-carbonyl)-1H-pyrrole-2-carbaldehyde (66.7 mg, 0.3 mmol) and piperidine (3 drops) in ethanol (2 mL) was stirred at room temperature for 4 days. The precipitate was collected by vacuum filtration, washed with ethanol and dried to give 105 mg (87%) of the title compound. $^1$H NMR (360 MHz, DMSO-$d_6$) δ 13.16 (br s, 1H, NH), 11.74 (br s, 1H, NH), 8.78 (br s, 1H), 8.27 (s, 1H), 7.74 (dd, J=2.2 & 6.5 Hz, 1H), 7.71 (s, 1H), 7.52 (m, 1H), 7.38 (t, J=9.1 Hz, 1H), 6.74 (s, 1H), 3.65 (m, 4H, 2×CH$_2$z), 3.54 (m, 4H, 2×CH$_2$), 2.15 (s, 3H, CH$_3$). MS 483 [M$^+$+1].

5.35. Example 35

SYNTHESIS OF 4-(3-CHLORO-4-FLUORO-PHENYLAMINO)-5-(3,5-DIMETHYL-1H-PYRROL-2-YLMETHYLENE)-7-METHYL-5,7-DIHYDRO-PYRROLO[2,3-D]PYRIMIDIN-6-ONE (FORMULA 38)

4-(3-Chloro-4-fluoro-phenylamino)-7-methyl-5,7-dihydro-pyrrolo[2,3-d]pyrimidin-6-one (100 mg, 0.34 mmol) was condensed with 3,5-dimethyl-1H-pyrrole-2-carbaldehyde (50 mg, 0.41 mmol) and piperidine (2 drops) in ethanol (3 mL) at 80° C. for 2 hours to give 50 mg (37%) of the title compound. $^1$H NMR (300 MHz, DMSO-$d_6$) δ 13.07 (br s, 1H, NH), 9.18 (s, 1H), 8.34 (s, 1H), 7.69 (m, 1H), 7.35 (s, 1H), 7.30–7.40 (m, 2H), 6.05 (s, 1H), 3.32 (s, 3H, CH$_3$), 2.34 (s, 3H, CH$_3$), 2.16 (s, 3H, CH$_3$). MS 398 [M$^+$+1].

5.36 Example 36

SYNTHESIS OF 4-(3-CHLORO-4-FLUORO-PHENYLAMINO)-5-[3-METHYL-5-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 39)

To a suspension of 5-formyl-4-methyl-1H-pyrrole-2-carboxylic acid (1.53 g, 10 mmol) in DMF (20 mL) was added 1-methylpiperazine (1.2 g, 12 mmol), followed by 1-ethyl-3-(3-dimethylaminopropyl)carboiimide hydrochloride (EDAC, 2.3 g, 12 mmol), 1-hydroxybenzotriazole (HOBt, 1.6 g, 12 mmol) and triethylamine (3.2 mL, 24 mmol). The reaction mixture was stirred at room temperature for 2 days. The reaction was concentrated, diluted with water and extracted with ethyl acetate (5×). The combined ethyl acetate was concentrated to a volume of 20 mL and triturated with hexane (10 mL). The resulting solid was collected by vacuum filtration to give 1.6 g (68%) of 3-methyl-5-(4-methyl-piperazine-1-carbonyl)-1H-pyrrole-2-carbaldehyde as a yellow solid. $^1$N NMR (300 MHz, DMSO-$d_6$) δ 12.21 (s, 1H, NH), 9.7 (s, 1H, CHO), 6.35 (s, 1H), 3.58 (m, 4H 2×CH$_2$), 2.30 (m, 7H, 2×CH$_2$ & CH$_3$), 2.18 (s, 3H, CH$_3$). MS 236 [M$^+$1].

A mixture of 4-(3-chloro-4-fluoro-phenylamino)-5,7-dihydro-pyrrolo[2,3-d]pyrimidin-6-one (70 mg, 0.25 mmol) and 3-methyl-5-(4-methyl-piperazine-1-carbonyl)-1H-pyrrole-2-carbaldehyde (70.6 mg, 0.30 mmol) and piperidine (3 drops) in ethanol was stirred at room temperature for 4 days. The precipitate was collected by vacuum filtration, washed with ethanol and dried to give 124 mg (100%) of the title compound. $^1$H NMR (360 MHz, DMSO-$d_6$) δ 13.41 (s, 1H, NH), 11.77 (br s, 1H, NH), 9.22 (br s, 1H), 8.32 (s, 1H), 7.72 (dd, J=2.7 & 6.6 Hz, 1H), 7.42 (m, 1H), 7.32–7.37 (m, 2H), 6.58 (d, J=1.8 Hz, 1H), 3.68 (m, 4H, 2×CH$_2$), 2.36 (m, 4H, 2×CH$_2$), 2.22 (s, 3H, CH$_3$), 2.20 (s, 3H, CH$_3$). MS 496 [M$^+$+1].

5.37. Example 37

SYNTHESIS OF 3-{5-[4-(3-CHLORO-4-FLUORO-PHENYLAMINO)-7-METHYL-6-OXO-6,7-DIHYDRO-PYRROLO[2,3-D]PYRIMIDIN-5-YLIDENEMETHYL]-2,4-DIMETHYL-1H-PYRROL-3-YL}-PROPIONIC ACID (FORMULA 40)

4-(3-Chloro-4-fluoro-phenylamino)-7-methyl-5,7-dihydro-pyrrolo[2,3-d]pyrimidin-6-one (100 mg, 0.34 mmol) was condensed with 3-(5-formyl-2,4-dimethyl-1H-pyrrol-3-yl)-propionic acid (80 mg, 0.41 mmol) and piperidine (2 drops) in ethanol (3 mL) at 80° C. for 2 hours to give 36 mg (23%) of the title compound. $^1$H NMR (300 MHz, DMSO-$d_6$) δ 13.15 (br s, 1H, NH), 12.07 (br s, 1H, COOH), 9.18 (s, 1H), 8.33 (s, 1H), 7.71 (m, 1H), 7.40 (s, 1H), 7.30–7.39 (m, 2H), 3.32 (s, 3H, CH$_3$), 2.63 (m, 2H, CH$_2$), 2.35 (m, 2H, CH$_2$), 2.33 (s, 3H, CH$_3$), 2.13 (s, 3H, CH$_3$).

5.38. Example 38

SYNTHESIS OF 4-(3-CHLORO-4-FLUORO-PHENYLAMINO)-5-[3,5-DIMETHYL-4-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 41)

A mixture of 4-(3-chloro-4-fluoro-phenylamino)-5,7-dihydro-pyrrolo[2,3-d]pyrimidin-6-one (70 mg, 0.25 mmol), 3,5-dimethyl-4-(4-methyl-piperazine-1-carbonyl)-1H-pyrrole-2-carbaldehyde (74.8 mg, 0.3 mmol) and piperidine (3 drops) in ethanol (2 mL) was stirred at room temperature for 4 days. The precipitate was collected by vacuum filtration, washed with ethanol and dried to give 102 mg (80%) of the title compound. $^1$H NMR (360 MHz, DMSO-$d_6$) δ 13.27 (br s, 1H, NH), 11.66 (br s, 1H, NH), 9.12 (br s, 1H), 8.29 (s, 1H), 7.71 (m, 1H), 7.40 (m, 1H), 7.31–7.36 (m, 2H), 3.43 (m, 4H, 2×CH$_2$), 2.30 (s, 3H, CH$_3$), 2.27 (m, 4H, 2×CH$_2$), 2.18 (s, 3H, CH$_3$), 2.12 (s, 3H, CH$_3$). MS 510 [M$^+$+1].

5.39. Example 39

SYNTHESIS OF 3-{5-[4-(3-CHLORO-4-FLUORO-PHENYLAMINO)-7-METHYL-6-OXO-6,7-DIHYDRO-PYRROLO[2,3-D PYRIMIDIN-5-YLIDENEMETHYL]-4-METHYL-1H-PYRROL-2-YL}-PROPIONIC ACID (FORMULA 42)

4-(3-Chloro-4-fluoro-phenylamino)-7-methyl-5,7-dihydro-pyrrolo[2,3-d]pyrimidin-6-one (100 mg, 0.34 mmol) was condensed with 3-(5-formyl-4-methyl-1H-pyrrol-2-yl)-propionic acid (62 mg, 0.41 mmol) and piperidine (2 drops) in ethanol (3 mL) stirred at 80° C. for 2 hours to give 31 mg (20%) of the title compound. $^1$H NMR (360 MHz, DMSO-$d_6$) δ 13.14 (br s, 1H, NH), 9.14 (s, 1H), 8.34 (s, 1H), 7.69 (m, 1H), 7.30–7.40 (m, 3H), 6.08 (s, 1H), 3.32 (s, 3H, CH$_3$), 2.89 (m, 2H, CH$_2$), 2.53 (m, 2H, CH$_2$), 2.16 (s, 3H, CH$_3$).

5.40. Example 40

SYNTHESIS OF 4-(3-CHLORO-4-FLUORO-PHENYLAMINO)-5-[3,5-DIMETHYL-4-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 43)

A mixture of 4-(3-chloro-4-fluoro-phenylamino)-5,7-dihydro-pyrrolo[2,3-d]pyrimidin-6-one (70 mg, 0.25 mmol), 3,5-dimethyl-4-(morpholine-4-carbonyl)-1H-pyrrole-2-carbaldehyde (70.9 mg, 0.3 mmol) and piperidine (3 drops) in ethanol (2 mL) was stirred at room temperature for 4 days. The precipitate was collected by vacuum filtration, washed with ethanol and dried to give 98.5 mg (79%) of the title compound. $^1$H NMR (360 MHz, DMSO-$d_6$) δ 13.28 (br s, 1H, NH), 11.68 (br s, 1H, NH), 9.12 (br s, 1H), 8.29 (s, 1H), 7.71 (m, 1H), 7.40 (m, 1H), 7.31–7.36 (m, 2H), 3.56 (m, 4H, 2×CH$_2$), 3.45 (m, 4H, 2×CH$_2$), 2.31 (s, 3H, CH$_3$), 2.14 (s, 3H, CH$_3$). MS 497 [M$^+$+1].

5.41. Example 41

SYNTHESIS OF 4-(3-CHLORO-4-FLUORO-PHENYLAMINO)-5-[3,5-DIMETHYL-4-(3-MORPHOLIN-4-YL-PROPYL)-1H-PYRROL-2-YLMETHYLENE]-7-METHYL-5,7-DIHYDRO-PYRROLO[2,3-D]PYRIMIDIN-6-ONE (FORMULA 44)

A mixture of 4-(3-chloro-4-fluoro-phenylamino)-7-methyl-5,7-dihydro-pyrrolo[2,3-d]pyrimidin-6-one (100 mg, 0.34 mmol), 3,5-dimethyl-4-(3-morpholin-4-yl-propyl)-1H-pyrrole-2-carbaldehyde (85 mg, 0.34 mmol) and piperidine (2 drops) in ethanol (3 mL) was stirred at 80° C. for 1 hour. The reaction was concentrated and column chromatographed to give 46 mg (26%) of the title compound as a light yellow solid. $^1$H NMR (300 MHz, DMSO-$d_6$) δ 13.14 (br s, 1H, NH), 9.17 (s, 1H), 8.33 (s, 1H), 7.68 (m, 1H), 7.35 (s, 1H, H-vinyl), 7.32 (m, 2H), 3.55 (m, 4H, 2×CH$_2$), 3.30 (s, 3H, CH$_3$), 2.40 (m, 2H, CH$_2$), 2.31 (s, 3H, CH$_3$), 2.30 (m, 4H, 2×CH$_2$), 2.20 (m, 2H, CH$_2$), 2.10 (s, 3H, CH$_3$), 1.55 (m, 2H, CH$_2$).

5.42. Example 42

SYNTHESIS OF 4-(3-CHLORO-4-FLUORO-PHENYLAMINO)-5-[5-(4-METHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 45)

A mixture of 4-(3-chloro-4-fluoro-phenylamino)-5,7-dihydro-pyrrolo[2,3-d]pyrimidin-6-one (70 mg, 0.25 mmol), 5-(4-methyl-piperazine-1-carbonyl)-1H-pyrrole-2-carbaldehyde (66.4 mg, 0.3 mmol) and piperidine (3 drops) in ethanol (2 mL) was stirred at room temperature for 4 days. The precipitate was collected by vacuum filtration, washed with ethanol and dried to give 101.5 mg (84%) of the title compound. $^1$H NMR (360 MHz, DMSO-$d_6$) δ 13.39 (br s, 1H, NH), 11.74 (br s, 1H, NH), 8.81 (br s, 1H), 8.28 (s, 1H), 7.76 (s, 1H), 7.75 (m, 1H), 7.53 (m, 1H), 7.39 (t, J=8.9 Hz, 1H), 6.91 (m, 1H), 6.74 (m, 1H), 3.70 (m, 4H, 2×CH$_2$), 2.37 (m, 4H, 2×CH$_2$), 2.21 (s, 3H, CH$_3$). MS 482 [M$^+$+1].

5.43. Example 43

SYNTHESIS OF 5-[3-METHYL-5-(MORPHOLINE-4-CARBONYL)-1H-PYRROL-2-YLMETHYLENE]-4-(1-PHENYL-ETHYLAMINO)-5,7-DIHYDRO-PYRROLO[2,3-D]PYRIMIDIN-6-ONE (FORMULA 46)

A mixture of 4-chloro-5-[3-methyl-5-(morpholine-4-carbonyl)-1H-pyrrol-2-ylmethylene]-5,7-dihydro-pyrrolo[2,3-d]pyrimidin-6-one (37 mg, 0.1 mmol) and (R)-(+)-1-phenylethylamine (121 mg, 1 mmol) in 2-methoxyethanol (0.5 mL) was heated at 110–120° C. for 1.5 hours. The reaction was diluted with water and filtered. The precipitate was washed with water, little ethanol, ethyl acetate, hexane and dried to give 38.1 mg (81%) of the title compound as a yellow solid. MS 459 [M$^+$+1].

5.44. Example 44

SYNTHESIS OF 5-[4-(3-CHLORO-4-FLUORO-PHENYLAMINO)-6-OXO-6,7-DIHYDRO-PYRROLO[2,3-D]PYRIMIDIN-5-YLIDENEMETHYL]-4-METHYL-1H-PYRROLE-2-CARBOXYLIC ACID (FORMULA 47)

A mixture of 4-(3-chloro-4-fluoro-phenylamino)-5,7-dihydro-pyrrolo[2,3-d]pyrimidin-6-one (70 mg, 0.25 mmol), 5-formyl-4-methyl-1H-pyrrole-2-carboxylic acid (45.9 mg, 0.3 mmol) and piperidine (3 drops) in ethanol (2 mL) was stirred at room temperature for 4 days The precipitate was collected by vacuum filtration, washed with ethanol and dried, then washed with 1N HCl (3×), water (5×) and dried to give 88.8 mg (86%) of the title compound. $^1$H NMR (360 MHz, DMSO-$d_6$) δ 13.55 (br s, 1H, NH), 11.84 (br s, 1H, NH), 9.28 (s, 1H), 8.34 (s, 1H), 7.74 (m, 1H), 7.43 (m, 1H), 7.41 (s, 1H), 7.38 (t, J=9.1 Hz, 1H), 6.74 (d, J=2.15 Hz, 1H), 2.22 (s, 3H, CH$_3$). MS 414 [M$^+$+1].

5.45. Example 45

SYNTHESIS OF 5-[3-METHYL-5-(MORPHOLINE-4-CARBONYL)-1H-PYRROL-2-YLMETHYLENE]-4-PIPERIDIN-1-YL-5,7-DIHYDRO-PYRROLO[2,3-D]PYRIMIDIN-6-ONE (FORMULA 48)

A mixture of 4-chloro-5,7-dihydro-pyrrolo[2,3-d]pyrimidin-6-one (169 mg, 1 mmol), 3-methyl-5-(morpholine-4-carbonyl)-1H-pyrrole-2-carbaldehyde (222 mg, 1 mmol) and piperidine (2 drops) in ethanol (3 mL) was heated to reflux for overnight. The precipitate was collected by vacuum filtration, washed with ethyl acetate/hexane and dried to give 332.2 mg (79%) of the title compound as a yellow solid. MS 423 [M$^+$+1].

5.46. Example 46

SYNTHESIS OF 3-{5-[4-(3-CHLORO-4-FLUORO-PHENYLAMINO)-6-OXO-6,7-DIHYDRO-PYRROLO[2,3-D]PYRIMIDIN-5-YLIDENEMETHYL]-4-METHYL-1H-PYRROL-2-YL}-PROPIONIC ACID (FORMULA 49)

Sodium tert-butoxide (1.37 g, 14.3 mmol) was added to the dry tert-butoxycarbonylmethyl)triphenylphosphonium bromide (6.56 g, 14.3 mmol) in THF (anhydrous, 30 mL) under nitrogen. The mixture was stirred at room temperature for 30 minutes. To the mixture was added 5-formyl-3-methyl-1H-pyrrole-2-carboxylic acid ethyl ester (2.36 g, 13 mmol) in THF (35 mL). The mixture was then stirred at room temperature under nitrogen for overnight. The solid was filtered off and the filtrate was concentrated followed by column chromatograph (10% EtOAc in hexane) to give 2.95 g (81%) of 5-(2-tert-butoxycarbonyl-vinyl)-3-methyl-1H-pyrrole-2-carboxylic acid ethyl ester. $^1$H NMR (300 MHz, DMSO-$d_6$) δ 11.85 (br s, 1H, NH), 7.35 (d, J=15.7 Hz, 1H), 6.73 (s, 1H), 6.41 (d, J=15.7 Hz, 1H), 4.23 (q, J=7.1 Hz, 2H, OCH$_2$), 2.22 (s, 3H, CH$_3$), 1.44 (s, 9H, 3×CH$_3$), 1.28 (t, J=7.1 Hz, 3H, OCH$_2$CH$_3$). MS 279 [M$^+$].

A solution of 5-(2-tert-butoxycarbonyl-vinyl)-3-methyl-1H-pyrrole-2-carboxylic acid ethyl ester (2.48 g) in ethyl acetate (60(mL) and ethanol (30 mL) was hydrogenated using 1% palladium on carbon at room temperature for overnight to give 2.49 g (100%) of 5-(2-tert-butoxycarbonyl-ethyl)-3-methyl-1H-pyrrole-2-carboxylic acid ethyl ester as a white solid. $^1$H NMR (300 MHz, DMSO-d$_6$) δ 11.12 (br s, 1H, NH), 5.74 (d, J=2.3 Hz, 1H), 4.17 (q, J=7.1 Hz, 2H, OCH$_2$), 2.71 (t, J=7.5 Hz, 2H, CH$_2$), 2.47 (t, J=7.5 Hz, 2H, CH$_2$), 2.18 (s, 3H, CH$_3$), 1.36 (s, 9H, 3×CH$_3$), 1.28 (t, J=7.1 Hz, 3H, OCH$_2$CH$_3$). MS 282 [M$^+$+1].

Lithium hydroxide (1.02 g, 42.65 mmol) was added to a suspension of 5-(2-tert-butoxycarbonyl-ethyl)-3-methyl-1H-pyrrole-2-carboxylic acid ethyl ester (2.4 g, 8.53 mmol) in methanol (50 mL) and water (12 mL). Ethanol (4 mL) was added to the mixture (to aid solvation of the starting material) and it was stirred at room temperature for overnight. The reaction was diluted with water (20 mL), concentrated (to remove most of the alcohol) and extracted with ether. The aqueous layer was the acidified to pH=2 using 1N HCl (43 mL) and extracted with ethyl acetate (2×). The combined extract was then washed with brine, dried and concentrated to give 1.89 g of 5-(2-carboxy-ethyl)-3-methyl-1H-pyrrole-2-carboxylic acid ethyl ester as a white solid.

A mixture of 5-(2-carboxy-ethyl)-3-methyl-]H-pyrrole-2-carboxylic acid ethyl ester (1.8 g, 8 mmol) and lithium hydroxide (1.94 g, 8 mmol) in THF (40 mL) and water (48 mL) was stirred at room temperature for 2 days then in an oil bath of 80° C. for 4 hours. The reaction was cooled to room temperature, acidified to pH 2 using concentrated HCl, extracted with ethyl acetate. The organic layer was then dried and concentrated-to give 1.32 g of 5-(2-carboxy-ethyl)-3-methyl-1H-pyrrole-2-carboxylic acid.

A solution of 5-(2-carboxy-ethyl)-3-methyl-1H-pyrrole-2-carboxylic acid (1.3 g, 6.59 mmol) in trifluoroacetic acid (6 mL) was stirred at room temperature for 10 minutes. It was then cooled to 0° C. and to it was added triethyl orthoformate (6 mL). The mixture was stirred at 0° C. for 10 minutes and at room temperature for 10 minutes. The reaction was poured into water (50 mL) and extracted with ethyl acetate. The extract was dried and concentrated to give 1.2 g of 3-(5-formyl-4-methyl-1H-pyrrol-2-yl)-propionic acid as a brown solid. $^1$H NMR (300 MHz, DMSO-d$_6$) δ 12.17 (br s, 1H), 11.50 (br s, 1H), 9.44 (s, 1H, CHO), 5.85 (s, 1H), 2.74 (t, J=7.4 Hz, 2H, CH$_2$), 2.54 (t, J=7.4 Hz, 2H, CH$_2$), 2.23 (s, 3H, CH$_3$). MS 182 [M$^+$+1].

A mixture of 4-(3-chloro-4-fluoro-phenylamino)-5,7-dihydro-pyrrolo[2,3-d]pyrimidin-6-one (70 mg, 0.25 mmol), 3-(5-formyl-4-methyl-1H-pyrrol-2-yl)-propionic acid (54.4 mg, 0.3 mmol) and piperidine (3 drops) in ethanol (2 mL) was stirred at room temperature for 4 days. The reaction was concentrated, the residue was dissolved in water and acidified with 1N HCl to pH=2. The resultant solid was then washed with water, ethanol and dried to give 93.9 mg (85%) of the title compound. $^1$H NMR (360 MHz, DMSO-d$_6$) δ 13.18 (br s, 1H, NH), 12.19 (br s, 1H, COOH), 11.61 (br s, 1H, NH), 9.09 (s, 1H), 8.27 (s, 1H), 7.70 (m, 1H), 7.39 (m, 1H), 7.30–7.35 (m, 2H), 6.07 (s, 1H), 2.90 (t, J=7.2 Hz, 2H, CH$_2$), 2.60 (t, J=7.2 Hz, 2H, CH$_2$), 2.16 (s, 3H, CH$_3$). MS 442 [M$^+$+1].

5.47. Example 47

SYNTHESIS OF 4-(INDAN-4-YLAMINO)-5-[3-METHYL-5-(MORPHOLINE-4-CARBONYL)-1H-PYRROL-2-YLMETHYLENE]-5,7-DIHYDRO-PYRROLO[2,3-D]PYRIMIDIN-6-ONE (FORMULA 50)

A mixture of 4-chloro-5-[3-methyl-5-(morpholine-4-carbonyl)-1H-pyrrol-2-ylmethylene]-5,7-dihydro-pyrrolo[2,3-c]pyrimidin-6-one (50 mg, 0.13 mmol), 5-aminoindan (178.12 mg, 1.3 mmol) in 2-methoxyethapol (0.6 mL) was heated at 110–120° C. for 8 hours and extracted with ethyl acetate/water. The organic layer was concentrated, the residue was triturated with acetone and filtered to give 29 mg of a yellow solid. The mother liquor was concentrated and column chromatographed to give 10.1 mg of the product. Total yield was 39.1 mg (64%) of the title compound as a yellow solid. $^1$H NMR (300 MHz, DMSO-d$_6$) δ 13.42 (br s, 1H, NH), 11.74 (br s, 1H, NH), 9.11 (br s, 1H), 8.27 (s, 1H, H-vinyl), 7.25 (br s, 1H, NH), 7.04–7.15 (m, 3H), 6.57 (d, J=2.2 Hz, 1H), 3.63 (m, 8H, 4×CH$_2$), 2.79 (m, 4H, 2×CH$_2$), 2.08 (s, 3H, CH$_3$), 1.99 (m, 2H, CH$_2$). MS 471 [M$^+$+1].

5.48. Example 48

SYNTHESIS OF {5-[4-(3-CHLORO-4-FLUORO-PHENYLAMINO)-6-OXO-6,7-DIHYDRO-PYRROLO[2,3-D]PYRIMIDIN-5-YLIDENEMETHYL]-2,4-DIMETHYL-1H-PYRROL-3-YL}-ACETIC ACID (FORMULA 51)

A mixture of 4-(3-chloro-4-fluoro-phenylamino)-5,7-dihydro-pyrrolo[2,3-d]pyrimidin-6-one (70 mg, 0.25 mmol), (5-formyl-2,4-dimethyl-1H-pyrrol-3'-yl)-acetic acid (54.3 mg, 0.3 mmol) and piperidine (3 drops) in ethanol (2 mL) was stirred at room temperature for 1 day. The reaction was concentrated, the residue was suspended in 1N HCl. The precipitate was filtered, washed with water, suspended in hot ethyl acetate, filtered and dried to give 42 mg (38%) of the title compound. $^1$H NMR (300 MHz, DMSO-d$_6$) δ 13.21 (br s, 1H, NH), 12.17 (br s, 1H, COOH), 11.65 (s, 1H, NH), 9.13 (s, 1H), 8.26 (s, 1H), 7.71 (m, 1H), 7.3–7.4 (m, 3H), 3.37 (s, 2H, CH$_2$), 2.3 (s, 3H, CH$_3$), 2.10 (s, 3H, CH$_3$), MS 442 [M$^+$+1].

5.49 Example 49

SYNTHESIS OF 4-(3-CHLORO-4-FLUORO-PHENYLAMINO)-5-[5-(3,5-DIMETHYL-PIPERAZINE-1-CARBONYL)-3-METHYL-1H-PYRROL-2-YLMETHYLENE]-5,7-DIHYDRO-PYRROLO[2,3-D]PYRIMIDIN-6-ONE (FORMULA 52)

A mixture of 4-(3-chloro-4-fluoro-phenylamino)-5,7-dihydro-pyrrolo[2,3-d]pyrimidin-6-one (70 mg, 0.25 mmol), 5-(3,5-dimethyl-piperazine-1-carbonyl)-3-methyl-1H-pyrrole-2-carbaldehyde (74.8 mg, 0.3 mmol) and piperidine (3 drops) in ethanol (2 mL) was stirred at room temperature for overnight. The precipitate was collected by vacuum filtration, washed with ethanol and dried to give 93.1 mg (73%) of the title compound as a yellow solid. $^1$H NMR (360 MHz, DMSO-d$_6$) δ 13.39 (br s, 1H, NH), 11.75 (br s, 1H, NH), 9.23 (br s, 1H), 8.32 (s, 1H), 7.73 (dd, J=2.6 & 6.7 Hz, 1H), 7.41 (m, 1H), 7.33–7.38 (m, 2H), 6.57 (d, J=2 Hz, 1H), 4.22 (m, 2H, CH$_2$), 2.68 (m, 2H, CH$_2$), 2.52 (m, 2H, 2×CH), 2.22 (s, 3H, CH$_3$), 0.99 (d, J=6 Hz, 6H, 2×CH$_3$), 0.98 (s, 3H, CH$_3$). MS 510 [M$^+$+1].

5.50. Example 50

SYNTHESIS OF 4-(3-CHLORO-4-FLUORO-PHENYLAMINO)-5-[3-METHYL-5-(3,4,5-TRIMETHYL-PIPERAZINE-1-CARBONYL)-1H-PYRROL-2-YLMETHYLENE]-5,7-DIHYDRO-PYRROLO[2,3-D]PYRIMIDIN-6-ONE (FORMULA 53)

4-(3-Chloro-4-fluoro-phenylamino)-5,7-dihydro-pyrrolo[2,3-d]pyrimidin-6-one was condensed with 3-methyl-5-(3, 4,5-trimethyl-piperazine-1-carbonyl)-1H-pyrrole-2-carbaldehyde to give the title compound. $^1$H NMR (360 MHz, DMSO-$d_6$) δ 13.41 (br s, 1H, NH), 11.78 (br s, 1H, NH), 9.23 (br s, 1H), 8.33 (s, 1H), 7.72 (dd, J=2.5 & 6.5 Hz, 1H), 7.43 (m, 1H), 7.33–7.38 (m, 2H), 6.58 (m, 1H), 4.19 (m, 2H, CH$_2$), 2.78 (m, 2H), 2.23 (s, 3H, CH$_3$), 2.18 (s, 3H, CH$_3$), 2.11 (m, 2H), 1.06 (d, J=6.6 Hz, 6H, 2×CH$_3$). MS 524 [M$^+$+1].

5.51. Example 51

SYNTHESIS OF 4-(3-CHLORO-4-FLUORO-PHENYLAMINO)-5-[5-(4-ETHYL-PIPERAZINE-1-CARBONYL)-3-METHYL-1H-PYRROL-2-YLMETHYLENE]-5,7-DIHYDRO-PYRROLO[2,3-D]PYRIMIDIN-6-ONE (FORMULA 54)

A mixture of 4-(3-chloro-4-fluoro-phenylamino)-5,7-dihydro-pyrrolo[2,3-d]pyrimidin-6-one (70 mg, 0.25 mmol), 5-(4-ethyl-piperazine-1-carbonyl)-3-methyl-1H-pyrrole-2-carbaldehyde (74.8 mg, 0.3 mmol) and piperidine (3 drops) in ethanol (2 mL) was stirred at room temperature for overnight. The precipitate was collected by vacuum filtration, washed with ethanol and dried to give 93 mg (73%) of the title compound. $^1$H NMR (300 MHz, DMSO-$d_6$) δ 3.40 (br s, 1H, NH), 11.81 (br s, 1H, NH), 9.28 (br s, 1H), 8.33 (s, 1H), 7.72 (m, 1H), 7.33–7.45 (m, 3H), 6.58 (m, 1H), 3.68 (m, 4H, 2×CH$_2$), 2.31–2.42 (m, 6H), 2.22 (s, 3H, CH$_3$), 1.01 (t, J=7.2 Hz, 3H, CH$_2$CH$_3$). MS 510 [M$^+$+1].

5.52. Example 52

SYNTHESIS OF 4-(3-CHLORO-4-FLUORO-PHENYLAMINO)-5,7-DIHYDRO-PYRROLO[2,3-D]PYRIMIDIN-6-ONE (FORMULA 55)

To a solution of 4-chloro-7H-pyrrolo[2,3-d]pyrimidine (767.9 mg, 5 mmol) and 3-chloro-4-fluoro-phenylamine (873.4 mg, 6 mmol) in 25 mL of dry DMF under nitrogen was added silver trifluoromethanesulfonate (1.54 g, 6 mmol). The mixture was stirred at 95° C. for 15 hours. The cooled reaction was diluted with ethyl acetate (70 mL) and filtered through celite, washed thoroughly with ethyl acetate. The filtrate was washed with brine (5×). The brine was extracted with ethyl acetate which was then washed with brine. The combined ethyl acetate was dried (magnesium sulfate), concentrated and purified to give 1.22 g (93%) of (3-chloro-4-fluoro-phenyl)-(7H-pyrrolo[2,3-d]pyrimidin-4-yl)-amine as an off-white solid. m.p. 274–275° C. $^1$H NMR (360 MHz, DMSO-$d_6$) δ 11.78 (br s, 1H, NH), 9.41 (s, 1H), 8.31 (s, 1H), 8.28 (m, 1H), 7.79 (m, 1H), 7.37 (t, 1H), 7.25 (m, 1H), 6.76 (m, 1H). MS 263.4 [M$^+$+1].

To a stirred solution of (3-chloro-4-fluoro-phenyl)-(7H-pyrrolo[2,3-d]pyrimidin-4-yl)-amine (26.3 mg, 0.1 mmol) in one mL of t-butanol was added portionwise 64 mg (0.2 mmol) of pyridinium bromide perbromide (PBPB). The reaction mixture was stirred at room temperature for 4 hours. The reaction was diluted with ethyl acetate, washed with water, aqueous sodium sulfate, brine, dried and concentrated to give 5,5-dibromo-4-(3-chloro-4-fluoro-phenylamino)-5,7-dihydro-pyrrolo[2,3-d]pyrimidin-6-one (used in the next step without any purification).

A mixture of 5,5-dibromo-4-(3-chloro-4-fluoro-phenylamino)-5,7-dihydro-pyrrolo[2,3-d]pyrimidin-6-one (from above), zinc dust in 2 mL of acetic acid was stirred at room temperature for one hour. The reaction was diluted with ethyl acetate and filtered. The filtrate was washed with water, sodium bicarbonate and brine, dried, concentrated and purified to give 11.2 mg (combined yield of 40% for the 2 steps) of 4-(3-chloro-4-fluoro-phenylamino)-5,7-dihydro-pyrrolo[2,3-d]pyrimidin-6-one as an off-white solid. $^1$H NMR (300 MHz, DMSO-$d_6$) δ 11.08 (br s, 1H, NH), 9.02 (s, 1H), 8.33 (s, 1H), 8.02 (m, 1H), 7.58 (m, 1H), 7.35 (t, 1H), 3.45 (s, 2H, CH$_2$). MS 279.3 [M$^+$+1].

5.53. Example 53

SYNTHESIS OF 5-[4-(3-CHLORO-4-FLUORO-PHENYLAMINO)-7-MORPHOLIN-4-YLMETHYL-6-OXO-6,7-DIHYDRO-PYRROLO[2,3-D]PYRIMIDIN-5-YLIDENEMETHYL]-4-METHYL-1H-PYRROLE-2-CARBOXYLIC ACID (2-MORPHOLIN-4-YL-ETHYL)-AMIDE (FORMULA 56)

To the suspension of 5-[4-(3-Chloro-4-fluoro-phenylamino)-6-oxo-6,7-dihydro-pyrrolo[2,3-d]pyrimidin-5-ylidenemethyl]-4-methyl-1H-pyrrole-2-carboxylic acid (2-morpholin-4-yl-ethyl)-amide (170 mg, 0.32 mmol) in EtOH-Dioxane-DMF (2:2:1) (10 mL) was added N,N'-dimorpholinomethane (0.5 mL). The mixture was stirred at 100° C. for 18 hours and then cooled to room temperature. The product was crystallized out, filtered, washed by methanol, and dried under high vacuum to provide pure 5-[4-(3-chloro-4-fluoro-phenylamino)-7-morpholin-4-ylmethyl-6-oxo-6,7-dihydro-pyrrolo[2,3-d]pyrimidinylidenemethyl]-4-methyl-1H-pyrrole-2-carboxylic acid (2-morpholin-4-yl-ethyl)-amide (130 mg, 65%). MS 625 [M$^+$+1].

5.54. Example 54

SYNTHESIS OF 4-(3-CHLORO-4-FLUORO-PHENYLAMINO)-5-{1-[5-(MORPHOLINE-4-CARBONYL)-THIOPHEN-2-YL]-METHYLIDENE}-5,7-DIHYDRO-PYRROLO[2,3-D]PYRIMIDIN-6-ONE (FORMULA 57)

The mixture of 4-(3-chloro-4-fluoro-phenylamino)-5,7-dihydro-pyrrolo[2,3-d]pyrimidin-6-one (90 mg, 0.32 mmol), 5-(morpholine-4-carbonyl)-thiophene-2-carbaldehyde (82 mg, 0.36 mmol), and triethylamine (2 drops) in ethanol (3 mL) was heated at 90° C. oil bath for 2 hours, and cooled to room temperature. The solvent was evaporated and the residue was purified on a silica gel column eluting with methylene chloride-methanol (98:2 and 95:5) to provide pure 4-(3-chloro-4-fluoro-phenylamino)-5-{1-[5-(morpholine-4-carbonyl)-thiophen-2-yl]-methylidene}-5,7-dihydro-pyrrolo[2,3-d]pyrimidin-6-one (41 mg, 28%). MS 486 [M$^+$+1].

5.55. Example 55

SYNTHESIS OF 4-(3-CHLORO-4-FLUORO-PHENYLAMINO)-5-[1-(2-CHLORO-4-HYDROXY-PHENYL)-METHYLIDENE]-5,7-DIHYDRO-PYRROLO[2,3-D]PYRIMIDIN-6-ONE (FORMULA 58)

The mixture of 4-(3-chloro-4-fluoro-phenylamino)-5,7-dihydro-pyrrolo[2,3-d]pyrimidin-6-one (100 mg, 0.36 mmol), 2-chloro-4-hydroxy-benzaldehyde (84.5 mg, 0.54 mmol), and piperidine (3 drops), in ethanol (3 mL) was heated at 60° C. oil bath for 4 hours, and cooled to room temperature. The product was crystallized out, filtered, washed by ethanol, and dried under high vacuum to provide pure 4-(3-chloro-4-fluoro-phenylamino)-5-[-(2-chloro-4- hydroxy-phenyl)-methylidene]-5,7-dihydro-pyrrolo[2,3-d]pyrimidin-6-one. $^1$H NMR (400 MHz, DMSO-d$_6$) d 11.52 (br s, 1H), 10.45 (br s, 1H), 8.42 (s, 1H), 8.35 (br s, 1H), 7.65 (s, 1H), 7.11 (t, 1H), 6.96 (m, 1H), 6.79 (m, 1H), 6.72 (d, 1H), 6.66 (m, 1H), 6.56 (dd, 1H). MS 418 [M++1].

5.56. Example 56

Assay for Modulation of PDGFR Activity

Using the following reagents, supplies, and methods, the ability of the compounds of the invention to modulate the in vitro activity of the PDGFR can be readily determined in an enzyme-linked immunosorbent assay (ELISA).
Reagents and Supplies All ELISA reactions are performed in Corning 96-well ELISA plates (Corning, Catalog #25805-96). Monoclonal anti-PDGFR antibody (28D4C10) is stored at −20° C. in 50 mL tubes prior to use. Antibody isolation methods employed herein are commonly known in the art, such as those described in Harlow and Lane (Harlow, E. and Lane, D., 1988, "Antibodies: A Laboratory Manual", Cold Spring Harbor Laboratory Press, Cold Spring Harbor, N.Y.).

The dilution buffer is Dulbecco's Phosphate-Buffered Saline ((PBS); Gibco, Catalog #450-1300EB). Alternatively, PBS can be made, including magnesium, by using the following reagents in the following protocol. In order to make a one liter 10× stock solution of PBS, first add approximately 900 mL dH$_2$O to a 1 liter graduated cylinder to which is added 2.013 grams of KCl, 1.916 grams of KH$_2$PO$_4$ (monobasic), 80.65 grams of NaCl, and 11.50 grams of Na$_2$HPO$_4$ (dibasic). Stir the mixture, and when dissolved, bring the solution to pH 7.2 with HCl. Finally, add 1.017 grams of MgCl$_2$-6H$_2$O (anhydrous), and bring the volume to 1 liter dH$_2$O. Note that PBS can be left at room temperature, but 4° C. is the preferred storage temp.

TBST buffer (TBS+0.1% Triton X-100) is used at a final 1× working concentration. The buffer is prepared by adding about 900 mL dH$_2$O to a 1 liter graduated cylinder, and adding 6.057 grams of Tris and 8.766 grams of NaCl and stirring. When the reagents are dissolved, the mixture is brought to pH 7.2 with HCl. Next, 1 mL of Triton X-100 is added and the volume is brought to 1 liter with dH$_{22}$. Alternatively one can use a stock solution of TBS which, is pre-made and stored at 4° C., and to which is added Triton X-100 to a final concentration of 0.1%, with stirring until the detergent is dissolved. Note that TBST can be left at room temperature, but 4° C. is the preferred storage temperature.

The ELISA Blocking Buffer is prepared by weighing out 5 grams of Non-fat Instant Milk (Carnation) and pouring 100 mL of PBS (see above) into a clean beaker. Next, add the Instant milk to the PBS and stir at room temperature until the milk has dissolved. One hundred mL of ELISA Blocking Buffer (also "blocking buffer") is enough for about 6 assay plates. When stored at 4° C., this solution is stable for 1 to 2 weeks.

Lysates from PDGFR-β expressing NIH3T3 cells are obtained and stored at −80° C. in 1 mL aliquots. PDGFR-β expression in eukaryotic cells is well known in the art. Lysates are prepared by the following method. Place carrier dishes in ice trays, and after cooling, remove the media and replace with ice cold PBS. Remove the PBS and repeat. Aspirate left-over PBS if necessary and add 4 mL of ice cold HNTG lysis buffer (described below in Example 58) with a pipettor to each dish. Let sit on ice for 5–10 minutes and then scrape the cells with a rubber policeman. Take up lysate with a pipettor and add to a 30 mL centrifuge tube on ice. Vortex the tubes for 30–60 seconds and then centrifuge for 10 minutes at 7000 rpm in a J-20 rotor which has been precooled to below 0° C. Recover the supernatants and combine them in a 250 mL tube and place on ice. Perform protein determination to measure the total quantity of protein per mL of solution. Aliquot the lysate into 1 mL fractions and store at −80° C.

A 1× working solution of TBS buffer is prepared by adding 900 mL of dH$_2$O to a 1 liter graduated cylinder, and adding 6.057 grams of Tris and 8.766 grams of NaCl and stirring. When all reagents have dissolved, the solution is adjusted to pH 7.2 with HCl and the volume is brought to 1 liter dH$_2$O. A 10× stock solution can be made by multiplying the amounts by 10 (but keeping the final volume of 1 liter). This stock is then diluted 10 fold with dH$_2$O and its pH adjusted to 7.2. Note that TBS can be kept at room temperature, but is best stored at 4° C.

To make 1 liter of a 1× working solution of TBS+10% DMSO, add about 850 mL dH$_2$O to a 1 liter graduated cylinder and then add 6.057 grams of Tris and 8.766 grams of NaCl and stir. When all reagents have dissolved, pH the solution to pH 7.2 with HCl. Next, add 100 mL of DMSO and bring the volume to 1 liter with dH$_2$O. Alternatively add 25 mL DMSO to 225 mL TBS (see above). Note that the TBS will now only be 0.9×, but this should not effect the assay.

To make 1 mM Stock solution of 1 mM Adenosine-5'-triphosphate (ATP, from Equine muscle) add 2.75 mg ATP (Sigma, Catalog #A-5394) to 5 mL of dH$_2$O, and vortex. Note that larger volumes of stock solution can be prepared so long as the same ratio of ATP to dH$_2$O is used. Also note this reagent should be made up immediately prior to use and kept on ice.

A stock solution of 1 M MnCl$_2$ is prepared by adding 19.79 grams of MnCl$_2$ to 100 ml dH$_2$O and stirring until dissolved. The solution is then filtered, sterilized and stored in 1 ml aliquots at −80° C.

The 10× Kinase Buffer is composed of the following parts:

| Reagent | Stock solution | Amount per 10 mL | Working Concentration |
| --- | --- | --- | --- |
| Tris | 1 M | 250 μL | 25 mM |
| NaCl | 5 M | 200 μL | 100 mM |
| MnCl$_2$ | 1 M | 100 μL | 10 mM |
| TX-100 | 100% | 10 μL | 0.1% |
| DTT | 100 mM | 50 μL | 0.5 mM |

Ten milliliters of kinase buffer mix is sufficient for about 12.5 assay plates. To make Kinase Buffer, dilute 1.0 mL 10× Kinase Buffer to a final volume of 8.0 mL with water.

NUNC 96-well V bottom polypropylene plates (Applied Scientific, Catalog #AS-72092) are used for mixing the test drugs and the lysates.

An Ethylenediamine-tetraacetic acid (EDTA) 500 mM stock solution is prepared as follows: 1) Add about 70 mL dH$_2$O to a 250 mL beaker; 2) Add 14.12 g of EDTA; 3) With pH probe in beaker, add 10 N NaOH dropwise (EDTA will not dissolve until pH is around 7.0), and note that as EDTA dissolves, the pH will fall so more NaOH may need to be added; 4) When all EDTA is dissolved, adjust the pH to 8.0; 5) Transfer to 100 mL graduated cylinder, bring volume to 100 mL with dH$_2$O. To make 200 mM working solution add 30 mL dH$_2$O to 20 mL 500 mM EDTA (above).

Rabbit polyclonal anti-phosphotyrosine serum is generated as described by *Methods of Enzymology*, 201:65–79 (1991), and is stored at −80° C. in 0.1 mL aliquots. Antiserum is stable for several weeks when thawed and stored at 4° C. Goat anti-rabbit IgG peroxidase conjugate is commercially available (Biosource, Catalog #AL10404) is commercially available.

The developing reagent, which includes 2,2'-azino-bis (3-ethylbenzthiazoline-6-sulfonic acid) (ABTS) (Sigma, Catalog #A-1888) is prepared as follows. Add about 900 mL dH$_2$O to a 1 liter graduated cylinder. Add 19.21 grams of Citric Acid and 35.49 grams of Na$_2$HPO$_4$ and pH to 4.0 with phosphoric acid. Add ABTS and cover with foil. Let dissolve for about 0.5 hour and filter the solution. Note that the solution must be kept in the dark at 4° C. until ready to use.

Hydrogen peroxide 30% solution is conunonly available (Fisher, Catalog #H325). This should be stored in the dark at 4° C. until ready to use.

An ABTS/H$_2$O$_2$ formulation consists of 15 mL ABTS solution (above) and 2 µL H$_2$O$_2$. Prepare 5 minutes before use and leave at room temperature. Take out ABTS about 60 minutes prior to use and warm to room temperature, or warm quickly by placing tube in 37° C. water bath. Add 3 µL H$_2$O$_2$ prior to use.

0.2 M HCl is prepared by mixing 98.3 mL of dH$_2$O with 1.7 mL of HCl. This solution is stored at room temperature.

Procedure

Coat Corning 96 well ELISA plates with 0.5 µg per well 28D4C10 antibody in a volume of 100 µl PBS overnight, at 4° C. and remove unbound antibody, 28D4C10, from wells by inverting plate to remove liquid. Wash 1× with distilled H$_2$O by filling wells. Pat the plate on a paper towel to remove excess liquid.

Add 150 µL of Blocking Buffer to each well. Incubate for 30 minutes at room temperature, with shaking and wash plate 3× with deionized water, then once with TBST. Pat plate on a paper towel to remove excess liquid and bubbles Dilute lysate in PBS (10 mg lysate/100 µL PBS). Add 100 µL of diluted lysate to each well. Shake at room temperature for 60 min. Wash plate 3× with deionized water, then once with TBST. Pat plate on a paper towel to remove excess liquid and bubbles.

Add 80 µL Kinase Buffer to ELISA plate containing captured PDGFR.

Dilute drugs/extracts 1:10 (unless specified otherwise) in TBS+10% DMSO in 96-well polypropylene plates. (i.e., 10 µL compound+90 µL (TBS+10% DMSO)). Add 10 µL diluted drugs/extracts to ELISA plate. To control wells (wells which do not receive any drug) add 10 µL of TBS+10% DMSO. Incubate for 30 minutes while shaking at room temperature.

Add 10 mL 25 µM ATP directly to all wells except negative control well which does not receive ATP. (100 µL final volume in well with 2.5 µM ATP final concentration in well.) Incubate 30 minutes while shaking.

After 30 minutes stop reaction with addition of 10 µL of 200 mM EDTA pH 8.0 for 20 mM final in well. Wash 4× with deionized water, twice with TBST.

Add 100 µL per well of anti-phosphotyrosine mab (1:10,000 dilution in TBST). Incubate 30–45 minutes at room temperature, with shaking. Wash plate 3× with deionized water, then once with TBST. Pat plate on a paper towel to remove excess liquid and bubbles.

Add 100 µL per well of biosource Goat anti-rabbit IgG peroxidase conjugate (1:6,000 dilution in TBST). Incubate 30 minutes at room temperature with shaking. Wash plate 3× with deionized water, then once with TBST. Pat plate on a paper towel to remove excess liquid and bubbles.

Add 100 µL of ABTS/H$_2$O$_2$ solution to each well. Incubate 10 to 30 minutes while shaking. Remove any bubbles. If necessary stop reaction with the addition of 100 µL of 0.2M HCl per well Read assay on Dynatech MR7000 ELISA reader. Test Filter: 410 nM; Reference Filter: 630 nM.

A preferred template for the placement of controls in this experiment is provided below:

|   | 1 | 2 | 3 | 4 | 5 | 6 | 7 | 8 | 9 | 10 | 11 | 12 |
|---|---|---|---|---|---|---|---|---|---|----|----|----|
| A | POS |   |   |   |   |   |   |   |   |    |    | NEG |
| B | POS |   |   |   |   |   |   |   |   |    |    | NEG |
| C | POS |   |   |   |   |   |   |   |   |    |    | NEG |
| D | POS |   |   |   |   |   |   |   |   |    |    | NEG |
| E | NEG |   |   |   |   |   |   |   |   |    |    | POS |
| F | NEG |   |   |   |   |   |   |   |   |    |    | POS |
| G | NEG |   |   |   |   |   |   |   |   |    |    | POS |
| H | NEG |   |   |   |   |   |   |   |   |    |    | POS |

5.57. Example 57

Assay for Modulation of GST-FLK1 Activity

Using the following reagents, supplies, and method, the ability of compounds of the invention to affect the in vitro activity of Gst-Flk1 on the poly glutamic acid, tyrosine (pEY) peptide in a high throughput screening assay.

Reagents and Supplies

Assays are performed in Corning 96-well ELISA plates (Corning, Catalog #25805-96), using the pEY 4: 1, lyophilizate (Sigma, Catalog #P0275) as a substrate for FLK1. Prepare 1 mg/mL pEY in sterile PBS and store in 1 mL aliquots at −20° C.

Coat 2 µg/well of pEY in 100 µPBS at room temperature for 2 hours or 4° C. overnight. Cover plates well to prevent evaporation. Store at 4° C. for 7 to 10 days.

PBS Buffer is prepared by adding to a 1 liter graduated cylinder, about 900 mL dH$_2$O and 0.2 g of KH$_2$PO$_4$, 1.15 g of Na$_2$HPO$_4$, 0.2 g of KCl, and 8.0 g of NaCl. When all reagents have dissolved, pH to 7.2 with HCl, and bring volume to 1 liter dH$_2$O. A 10× stock solution can be made by multiplying the amounts by 10 (but keeping the final volume of 1 liter). This stock is then diluted 10 fold with dH$_2$O and its pH adjusted to 7.2. Note that PBS can be kept at room temperature, but is best stored at 4° C.

PBS-Tw Buffer is prepared as above, except prior to bringing the volume to 1 liter, 1 mL of tween-20 is added. Note that TBS-Tw can be left at room temperature, but 4° C. is the preferred storage temp.

TBB Blocking Buffer is prepared by adding to a 1 liter graduated beaker, about 900 mL dH$_2$O 1.21 g of Tris, 8.77 g of NaCl, and 1 mL of Tween-20. When all reagents have dissolved, bring pH to 7.2 with HCl. Next, add 10 g of BSA, and stir until dissolved. Bring volume to 1 liter with dH$_2$O and filter the solution to remove any particulate matter, before storing at 4° C. A 10× stock solution can be made by multiplying the amounts by 10 (but keeping the final volume of 1 liter). This stock is then diluted 10 fold with dH$_2$O. Filter the solution to remove any particulate matter, and store at 4° C. Note that when stored at 4° C., this solution is stable for about 4 to 8 weeks.

A PBS+1% BSA solution is prepared by adding to a 1 liter graduated beaker about 990 mL PBS. Next, 10 grams of BSA is added and stir until dissolved. Bring volume to 1 liter with PBS and filter the solution to remove any particulate matter, before storing at 4° C. Note that when stored at 4° C., this solution is stable for about 4 to 8 weeks.

HEPES buffer is commercially available (GIBCO, Catalog #15630-080).

GST-Flk1cd is purified from sf9 recombinant baculovirus transformation and stored at −80° C. in 100 µL aliquots (use 5 ng (0.005 μg)/well in kinase dilution buffer, KDB). The transformation is prepared as follows. GST-fusion proteins of Flk-1(cd) is produced in the baculovirus expression system using pFBG2T as the transfer vector. This plasmid contains the GST coding sequence, amplified by PCR as a BamHI/BglII fragment and cloned into the BamHI site of pFastBac-1 (GIBCO-BRL). The portion of Flk-1 cDNA encoding amino acids 812–1346 is amplified by PCR as a NotI/SphI fragment and ligated downstream of and in-frame with the GST coding sequence in pFBG2T. Recombinant viruses are produced following standard protocols (GIBCO-BRL, FastBac manual). For protein production Sf9 cells are infected following standard procedures (King, L. A. and Possee, R. D. "The Baclovirus Expression System. A Laboratory Guide," Chapman and Hall, London (1992)) and fusion proteins purified by affinity chromatography on glutathione-sepharose (Sigma).

A solution of $dH_2O$+4% DMSO is prepared by mixing 10 mL of DMSO with 240 mL $dH_2O$ and stirring.

Adenosine-5'-triphosphate (from Equine muscle) 10 mM ATP (Sigma, Catalog #A-5394) is prepared by adding 5 mL of $dH_{20}$ to 27.5 mg ATP vortexing. Note that any amount of ATP can be used provided it is kept in the same ATP to $dH_2O$ ratio. Also note this reagent can be stored at −20° C. in small aliquots to be taken out just prior to use and kept on ice. Do not freeze/thaw aliquots; discard any unused portion.

A stock solution of 1 M $MnCl_2$ is prepared by adding 19.79 grams of $MnCl_2$ to 10 mL of $dH_2O$ and stirring. Once the $MnCl_2$ has dissolved, filter sterilize and store at −20° C. A working stock of 40 mM $MnCl_2$ is prepared by mixing 96 mL of $dH_2O$ and 4 mL of $MnCl_2$ from the 1 M stock solution immediately prior to use.

One hundred mL of kinase buffer mix is enough for about 40 assay plates. Kinase Dilution Buffer (KDB) is prepared by mixing 88.56 mL of $dH_2O$ with 10 mL of 1M Hepes pH 7.5, 1 mL of 5M NaCl, 40 ml of 100 mM sodium vanadate and 0.4 mL of 5% BSA (in $dH_2O$).

One hundred mL of kinase buffer mix is enough for about 40 assay plates. Kinase assays are performed in NUNC 96-well V bottom polypropylene plates (Applied Scientific, Catalog #AS-72092).

Ethylenediamine-tetraacetic acid (EDTA) is prepared as in Example 56.

1° and 2° Antibody Dilution Buffer is prepared by mixing 89.5 mL of PBSTw with 0.5 mL of milk in PBS, 1 mL of 10 mM Sodium vanadate and 10 mL of 5% BSA in PBS.

Anti-phosphotyrosine rabbit polyclonal antisera and goat anti-rabbit HRP conjugate are commercially available (Biosource, catalog #A110404).

ABTS Solution is prepared as in Example 56.

Hydrogen peroxide 30% solution (Fisher, Catalog #H325). Store in the dark at 4° C. until ready to use.

ABTS/$H_2O_2$ is prepared as in Example 56. Take out ABTS about 60 minutes prior to use and warm to room temperature. Or warm quickly by placing tube in 37° C. water bath. Add 3 μL $H_2O_2$ prior to use.

0.2 M HCl as described above and store at room temperature.

Procedure

Coat Corning 96 well ELISA plates with 2 μg of polyEY peptide in sterile PBS. Remove unbound liquid from wells by inverting plate. Wash 1×TBSTw. Pat the plate on a paper towel to remove excess liquid.

Add 100 μL of 1% BSA in PBS to each well. Incubate for 1 hour at room temperature, with shaking. Repeat removal of unbound liquid from wells by inverting plate. Wash 1×TBSTw. Pat the plate on a paper towel to remove excess liquid.

Soak wells with 50 mM Hepes pH 7.5 using 150 μL/well.

Dilute drugs with the extracts at 4× the desired final assay concentration in $dH_2O$+4% DMSO (unless specified otherwise) in NUNC 96-well polypropylene plates. Always add the larger volume of water to the smaller volume of compound to ensure rapid mixing. Add 25 μL diluted drugs/extracts to ELISA plate. To control wells (wells which do not receive any drug) add 25 μL of $dH_2O$+4% DMSO.

Dilute GST-Flk1 0.005 μg (5 ng)/well in KDB. For 50 mL KDB add 100 μL of 0.050 mg/mL GST-Flk1 enzyme. This is enough for a 10 assay plate. Add 50 μL of diluted enzyme to each well. Add 25 μL 0.5 M EDTA to negative control wells.

Add 25 μL of 40 mM $MnCl_2$ with 4×ATP (2 μM) directly to all wells (100 μL final volume in well with 0.5 μM ATP final concentration in well.) Incubate for 15 minutes while shaking at room temperature. After 15 minutes stop reaction with addition of 25 μL of 500 mM EDTA pH 8.0 for 50 mM final in well. Wash 3× with TBSTw and pat plate on paper towel to remove excess liquid.

Add 100 μL per well of anti-phosphotyrosine antisera (1:10,000 dilution in antibody dilution buffer). Incubate 90 minutes at room temperature, with shaking. Wash 1× with TBSTw and pat plate on paper towel to remove excess liquid.

Add 100 μL per well of goat anti-rabbit HRP conjugate (1:6,000 dilution in antibody dilution buffer). Incubate 90 minutes at room temperature with shaking. Wash 3×TBSTw. Pat the plate on a paper towel to remove excess liquid.

Add 100 μL at room temperature. ABTS/$H_2O_2$ solution to each well. Incubate 15 to 30 minutes while shaking. Remove any bubbles. If necessary stop reaction with the addition of 100 μL of 0.2M HCl per well.

Read assay on Dynatech MR7000 ELISA reader: Test Filter: 410 nM; Reference Filter: 630 nM. A preferred template for the placement of controls in this experiment is provided above in Example 56.

5.58. Example 58

Assay for Modulation of HER-2 Activity

Using the following reagents, supplies, and method, the ability of compounds of the invention to affect the activity of HER-2 in whole cells in an ELISA format can be assigned.

Materials and Reagents

Tissue Culture

Liquid culture media, DMEM, (GIBCO, Catalog #11965-092), and heat inactivated Fetal Bovine Serum (FBS), (GIBCO, Catalog #16000-044) are commercially available. Trypsin, (GIBCO, Catalog #25200-056), L-Glutamine stored in 6 mL aliquots at −20° C. (GIBCO, Catalog #25030-081), and HEPES, (GIBCO, Catalog #15630-080) are also commercially available.

Growth Media is prepared by adding to a 500 mL bottle of DMEM, 10% heat inactivated FBS (55 mL), 10 mL HEPES and 5.5 mL L-Glutamine. Starvation Media is prepared by adding to a 500 mL bottle of DMEM, 0.5% heat inactivated FBS (2.5 mL), 10 mL HEPES and 5.5 mL L-Glutamine.

Flat Bottom 96-well Tissue Culture Micro Titer Plates, (Corning, Catalog #25860), 15 cm Tissue Culture Dishes, (Corning, Catalog #08757 148), Corning 96-well ELISA Plates, (Corning, Catalog #25805-96), NUNC 96-well V bottom polypropylene plates (Applied Scientific, Catalog #AS-72092), and Costar Transfer Cartridges for the Transtar 96, Catalog #76 10 are all commercially available.

SUMO1 is a monoclonal anti-EGFR antibody. More specifically, SUMO1 is ascites-derived anti-EGFR monoclonal antibody produced by the hybridoma clone mAb188 (*PNAS* 86: 925–929 (1989)). The antibody is purified by conventional means using Protein A-agarose as described (Harlow, E. and Lane, D., 1988, "Antibodies: A Laboratory Manual", Cold Spring Harbor Laboratory Press, Cold Spring Harbor, N.Y.).

PBS (GIBCO, Catalog #450-1300EB), is obtained from a commercial supplier or prepared as described in Example 56.

TEST Buffer is prepared in a stock solution by adding 6.057 grams of Tris, and 8.766 grams of NaCl to 900 mL of $dH_2O$ and pH to 7.2.1 mL of Triton X-100 is next added to the $dH_2O$ and the mixture is brought to 1 L with $dH_2O$. 5% Blocking Buffer is prepared by weighing 5 grams of Non-fat Instant and pouring 100 mL of TEST (see above) into a clean beaker. Next add instant milk to TEST, stir at room temperature until the milk has dissolved. Note that when stored at 4° C., this solution is stable for 1 to 2 weeks.

The EGF Ligand: EG.-201, (Shinko American, Japan) is conmuercially available. Store powder vials (100 μg/vial) at 4° C., EGF Ligand at a stock concentration of 16.5 μM is prepared by resuspending all of the powder in the vial with 100 μL of 10 mM HCl and adding 100 μL of 10 mM NaOH. Then add 800 μL of PBS to the vial and transfer to an eppendorf tube for storage at −20° C. Note that for best results, make up one EGF vial right before use. Resuspended EGF is typically stable at −20° C. for several weeks.

A stock solution of 5×KNTG Lysis Buffer is prepared by mixing 23.83 grams of HEPES and 43.83 grams of NaCl in 350 mL of $dH_2O$. The mixture is brought to pH 7.2 and 500 mL of glycerol and 100 mL of Triton X-100 are added. The volume is brought to 1 L with $dH_2O$, and stirred to the reagents.

1×HNTG* buffer is prepared by mixing 2 mL of HNTG with 100 μL of 1 mM $Na_3VO_4$, 240 μL of 25 mM $Na_4P_2O_7$ and 100 mL of 5 mM EDTA. The mix is brought to 10 mL with $dH_2O$.

Prepare EDTA as described in Example 56.

A 0.1 M $Na_3VO_4$ stock solution is prepared by adding about 90 mL $dH_2O$ to a 250 mL beaker and then adding $Na_3VO_4$. With pH probe in beaker, pH to 10 (turns orange) and then bring to a boil by microwaving for about 1 minute (solution turns clear). Cool to room temperature and put in water bath. Check pH and bring to pH 10 before boiling and cooling until pH remains at 10. Use HCl or NaOH to adjust pH and make 1 mL aliquots to keep at −80° C.

A 0.2 M $Na_4P_2O_7$ stock solution (Fisher, Catalogue #5390) is prepared by adding 8.92 grams to 100 mL of $dH_2O$. Filter the solution prior to use.

Rabbit polyclonal antiserum specific for phosphotyrosine (anti-Ptyr antibody) is generated as described by *Methods of Enzymology*, 201:65–79 (1991).

Affinity purified antiserum, goat anti-rabbit IgG antibody, peroxidase conjugate is commercially available (Biosource antibody Cat #AL10404).

ABTS Solution is prepared as in Example 56.

Hydrogen peroxide 30% solution (Fisher, Catalog #H325). Store in the dark at 4° C. until ready to use.

ABTS/$H_2O_2$ is prepared as in Example 56. Take out ABTS about 60 minutes prior to use and warm to room temperature. Or warm quickly by placing tube in 37° C. water bath. Add 3 μL $H_2O_2$ prior to use.

0.2 M HCl as described above and store at room temperature.

Procedure

A. Pre-coating ELISA Plate

Coat Corning 96 well ELISA plates with SUMO1 at 1.0 μg per well in PBS, 100 μL final volume/well, overnight at 4° C. Coated plates are good for up to 10 days when stored at 4° C. If necessary, plates may be coated at room temperature for two hours while shaking.

On day of use, remove coating buffer and wash plate 3 times with deionized water and once with TEST buffer. Note that all washes should be done in this manner, unless otherwise specified. Add 100 μL of blocking buffer to each well. Incubate plate, shaking, at room temperature for 30 minutes. Just prior to use, wash plate as described above.

B. Seeding Cells

EGFR/HER-2chimera/#T3-C7 cell lines are used for this assay. Choose dishes having 80–90% confluence for the experiment. Collect cells by trypsinization and centrifuge at 1000 rpm at room temperature for 5 minutes.

Resuspend cells in starve medium and count with trypan blue. Only viability above 90% is acceptable. Seed cells in starve medium at a density of 2,500 cells per well, 90 μL per well, in a 96 well microtiter plate. Incubate seeded cells in 5% $CO_2$ at 37° C. overnight. Start the assay two days after seeding.

C. Assay Procedures

Primary Screening

Samples are diluted directly into a polypropylene plate containing starve-DMEM (non-sterile is okay). This dilution will be 1:10 or greater, depending on the samples being screened. The same amount of DMSO is put into the control wells. All cells are then transferred to the cell plate at a 1:10 dilution (10 μL of sample and media into 90 μL of starve media). The final DMSO concentration will be 1% or lower.

Secondary Screening

Ten samples are put into wells 2–11 of row A of the NUNC 96 well polypropylene plate. These wells contain straight starve-DMEM. For a 1:10 dilution, one would put 10 μL of drug into 90 μL of media. The rest of the wells (including the controls) will have a DMSO/media mixture. The percentage of DMSO in this mixture is determined by the first dilution factor, in this case 1:10. The DMSO concentration is therefore 10%. An equal amount of drug and media from row A is put into row B, containing DMSO and media. The same amount is then taken out and put into row C. This is repeated for all rows. These are 1:2 dilutions. All wells are then transferred to the cell plate at a 1:10 dilution (10 μL of sample and media into 90 μL of starve-DMEM. The final DMSO concentration will be 1% or lower.

Incubate in 5% $CO_2$ at 37° C. for 2 hours and in the incubation period, prepare EGF ligand by diluting stock EGF (16.5 μM) in warm DMEM (non-sterial is okay) to 150 μM and prepare fresh HNTG* sufficient for 100 uL per well and place on ice.

After a 2 hour incubation with the drug, add prepared EGF ligand to cells at 50 μL per well, for a final concentration of 50 nM. Positive control wells (8) receive the same amount of EGF. Negative controls do not receive EGF. Incubate at 37° C. for 10 minutes.

Remove drug, EGF, and DMEM by dumping in sink. Wash cells once with PBS.

Transfer HNTG* to cells, 100 μL per well. Place on ice for 5 minutes. Meanwhile, remove blocking buffer from ELISA plate and wash as described above. With a pipette tip securely fitted to a micropipettor, scrape cells from plate and homogenize cell material by repeatedly aspirating and dispensing the HNTG* lysis buffer. Transfer lysate to a coated, blocked, washed ELISA plate. Alternatively, one may use a Costar transfer cartridge to transfer lysate to the ELISA plate. Incubate, shaking, at room temperature for one hour.

Remove lysate by dumping in sink, then wash as described earlier. Transfer freshly diluted anti-phosphotyrosine (anti-Ptyr) antibody (1:3000 in TEST) to ELISA plate, 100 µL per well. Incubate, shaking, at room temperature, for 30 minutes.

Remove anti-Ptyr antibody by dumping in sink, then wash as described earlier. Transfer freshly diluted BIOSOURCE antibody to ELISA plate, (1:8000 in TEST), 100 µL per well. Incubate, shaking, at room temperature for 30 minutes.

Remove BIOSOURCE antibody by dumping in sink, then wash as described earlier. Transfer freshly prepared ABTS/$H_2O_2$ solution to ELISA plate, 100 mL per well. Incubate 5–10 minutes while shaking. Remove any bubbles and if necessary, stop reaction with the addition of 100 µL of 0.2 M HCl per well.

Read assay on Dynatech MR7000 ELISA reader. Test Filter: 410 nM; Reference Filter: 630 nM. A preferred template for the placement of controls in this experiment is provided below:

|   | 1 | 2 | 3 | 4 | 5 | 6 | 7 | 8 | 9 | 10 | 11 | 12 |
|---|---|---|---|---|---|---|---|---|---|----|----|----|
| A | POS | | | | | | | | | | | POS |
| B | POS | | | | | | | | | | | POS |
| C | POS | | | | | | | | | | | POS |
| D | POS | | | | | | | | | | | POS |
| E | NEG | | | | | | | | | | | NEG |
| F | NEG | | | | | | | | | | | NEG |
| G | NEG | | | | | | | | | | | NEG |
| H | NEG | | | | | | | | | | | NEG |

5.59. Example 59

Assay for Inhibition of CDK2

Using the following reagents, supplies, and method, the ability of compounds of the invention to assay for modulation of the in vitro kinase activity of human cdk2/cyclin A in a Scintillation Proximity Assay (SPA).

Reagents and Supplies

Assays are performed in Wallac 96-well polyethylene terephthalate (flexi) plates (Wallac, Catalog #1450-401). Amersham Redivue [$\gamma^{33}$P] ATP (Amersham, Catalog #AH 9968).

Beads for the assay are Amersham streptavidin coated polyvinyltoluene SPA beads (Amersham, Catalog #RPNQ0007). Reconstitute beads in PBS without magnesium or calcium, at 20 mg/mL. Store reconstituted beads at 4° C.

Activated cdk2/cyclin A enzyme complex is purified from Sf9 cells and stored at −80° C. in 200 µL aliquots. Human cdk2/cyclin A protein is expressed, activated, and purified from baculovirus infected sf9 cells as described previously. (*J. Mol. Biol.*, 230:1317–1319 (1993)).

The substrate is a biotinylated peptide substrate (Debtide), which is a peptide biotin-X-PKTPKKAKKL dissolved in $dH_2O$ at a concentration of 5 mg/mL and stored at −80° C. in 100 µL aliquots.

The Peptide/ATP mixture is prepared by mixing 9.979 mL $dH_2O$ with 0.00125 mL of cold 10 mM ATP, 0.010 mL of 5 mg/mL Debtide, and 0.010 mL of 10 µCi/mL $\gamma^{33}$P ATP.

A 2.5× kinase buffer is prepared by mixing 8.85 mL of $dH_2O$ with 0.625 mL of 1M Tris pH 7.4, 0.25 mL of 1M $MgCl_2$, 0.25 mL of 10% NP40, and 0.025 mL of 1M DTT. Ten milliliters of kinase buffer mix is sufficient for about 4.5 assay plates.

10 mM Adenosine-5'-triphosphate (from Equine muscle) ATP (Sigma, Catalog #A-5394) is prepared as in Example 57. Note that this reagent can be stored at −20° C. in small aliquots to be taken out just prior to use and kept on ice. Do not freeze/thaw aliquots; discard any unused portion.

PBS (Dulbecco's Phosphate-Buffered Saline) without magnesium or calcium (Gibco, Catalog #14 190-144) is purchased from a commercial supplier or prepared as in Example 57 and a stock solution of 500 mM EDTA is prepared as in Example 56.

Prior to the experiment, prepare the following stock solution:

| Reagent | Stock solution | Amount per 10 mL | Working Concentration |
|---|---|---|---|
| PBS | | 9.25 mL | |
| ATP | 100 mM | 0.005 mL | 50 µM |
| EDTA | 0.5 M | 0.1 mL | 5 mM |
| TritonX-100 | 10% | 0.1 mL | 0.1% |
| SPA beads | 20 mg/mL | 1.25 mL | 0.5 mg/well (200 µL) |

Procedure

Prepare solutions of inhibitors at 5× the desired final concentration in 5% DMSO. Add 10 µL to each well. For negative controls, add 10 µL 5% DMSO.

Dilute 5 µL of cdk2/cyclin A solution into 2.1 mL 2× kinase buffer (per plate) and add 20 µL enzyme per well. This can be added using a hand pipette or by using the Titertek Multidrop. Note that the enzyme can be freeze/thawed, but this results in loss of some activity. For each freeze/thaw cycle, double the amount of enzyme used in the assay. Also, the enzyme should be thawed quickly (e.g., in the palm of one's hand) and be kept on ice prior to use in the assay. Add 10 µL of 0.5 M EDTA to the negative control wells.

To start kinase reaction, add 20 µL of peptide/ATP mixture using either a hand pipette or the Titertek Multidrop. Let sit on benchtop behind shield for one hour. No shaking is necessary and is not recommended when using Flexiplates (plates are not easy to add/remove from shaker).

Add 200 µL stop solution per well using either the Titertek Multidrop or hand pipette. Let stand at least 10 minutes. Spin plate approximately 2300 rpm for 3–5 minutes. Count plate on Trilux reader.

A preferred template for the placement of controls in this experiment is shown above in Example 56.

5.60 Example 60

Assay for Modulation of EGFR Activity

Using the following reagents, supplies, and method, the ability of compounds of the invention to modulate the in vitro activity of EGFR can be readily determined in an ELISA.

Reagents and Supplies

Reactions are performed in Corning 96-well ELISA plates (Corning, Catalog #25805-96).

SUMO1 is a monoclonal anti-EGFR antibody stored at −20° C., in 1 mL aliquots and is described in Example 58.

PBS (Gibco, Catalog #450-1300EB) is purchased from a commercial source or made as described in Example 56.

TBS Buffer is prepared as in Example 56, and Triton X-100 is added to a 0.1% Blocking Buffer is prepared as in Example 57.

A431 mouse cell lysate is stored at −80° C. (ATCC, Catalog µe #HB-9629).

TBS+10% DMSO is prepared as in Example 56.

A 1.0 mM ATP stock solution and a 1 M $MnCl_2$ stock solution are prepared as described above.

ATP/$MnCl_2$ phosphorylation mix is prepared by adding 300 µL of 1.0 mM ATP and 500 mL of 1M $MnCl_2$ to 9.2 mL of $dH_2O$ and mixing. Ten mL of phosphorylation mix is enough for about 6 assay plates. Note that the mixture should be made fresh and kept on ice immediately before use, and that although the preferred ATP is fresh from powder stock, any remaining stock solution of ATP may be frozen at −20° C. in small aliquots to be used at a later time.

NUNC 96-well V bottom polypropylene plates are used for the reactions (Applied Scientific, Catalog #AS-72092).

EDTA is prepared as described in Example 56.

Rabbit polyclonal anti-phosphotyrosine serum is prepared as described above and stored at −80° C., 1 mL aliquots. Thaw 1 mL vial and aliquot in smaller volumes to store at −80° C. Antiserum is stable for several weeks when thawed and stored at 4° C. Goat anti-rabbit IgG peroxidase conjugate (Biosource, Catalog #AL10404) is commercially available.

ABTS Solution is prepared as described in Example 56.

Hydrogen peroxide 30% solution is commercially available (Fisher, Catalog #H325). Store in the dark at 4° C. until ready to use.

ABTS/$H_2O_2$ is prepared as in Example 56.

Take out ABTS about 60 minutes prior to use and warm to room temperature. Or warm quickly by placing tube in 37° C. water bath. Add 3 mL $H_2O_2$ prior to use.

0.2 M HCl as described above and store at room temperature.

Procedure

Coat Corning 96 well ELISA plates with 0.5 µg per well with SUMO1 in a volume of 100 µL PBS overnight, at 4° C. Remove unbound SUMO1 from wells by inverting plate to remove liquid. Wash 1× with distilled $H_2O$ by filling wells. Pat the plate on a paper towel to remove excess liquid.

Add 150 µL of Blocking Buffer to each well. Incubate for 30 minutes at room temperature, with shaking. Wash plate 3× with deionized water, then once with TBST. Pat plate on a paper towel to remove excess liquid and bubbles.

Dilute lysate in PBS (7 µg lysate/100 mL PBS) and add 100 µL of diluted lysate to each well. Shake at room temperature for 60 minutes. Wash 1× with distilled $H_2O$ by filling wells. Pat the plate on a paper towel to remove excess liquid.

Add 120 µL TBST to ELISA plate containing captured EGFR.

Dilute drugs/extracts 1:10 (unless specified otherwise) in TBST in 96-well polypropylene plates. (i.e., 10 µL compound+90 µL TBST). Add 13.5 µL diluted drugs/extracts to ELISA plate. To control wells (wells which do not receive any drug) add 13.5 µL of TBST+10% DMSO. Incubate for 30 minutes while shaking at room temperature.

Add 15 µL phosphorylation mix directly to all wells except negative control well which does not receive ATP/$MnCl_2$. Approximately 150 µL final volume in well with 3 uM ATP/5 mM $MnCl_2$ final concentration in well. Incubate 5 minutes while shaking. Note that this is a timed event. It is critical that ATP/$MnCl_2$ phosphorylates the receptor for only 5 minutes. It is best to add the ATP/$MnCl_2$ with an automated 96 place pipettor workstation, then 5 minutes later stop the reaction with EDTA using the same workstation. Alternatively, addition can be performed using a 12 channel pipettor 1 row at a time, leaving 20 seconds between each row so that the reaction may be stopped with EDTA exactly 5 minutes later (this depends on the number of plates being phosphorylated in one batch). Shake between each addition.

After 5 minutes, to stop the reaction, add 16.5 µL of 200 nM EDTA pH 8.0 for 20 mM final in well, shaking continuously between each addition. This is done using either the same work station as above, or the same timing method employed with the 12 channel pipettor. After the EDTA has been added, shake for 1 minute. Wash 4× with deionized water, twice with TBST.

Add 100 µL per well of anti-phosphotyrosine (1:3000 dilution in TBST). Incubate 30–45 minutes at room temperature, with shaking. Wash 1× with distilled $H_2O$ by filling wells. Pat the plate on a paper towel to remove excess liquid.

Add 100 µL per well of biosource Goat anti-rabbit IgG peroxidase conjugate (1:2000 dilution in TBST). Incubate 30 minutes at room temperature, with shaking. Wash 1× with distilled $H_2O$ by filling wells. Pat the plate on a paper towel to remove excess liquid.

Add 100 µL of ABTS/$H_2O_2$ solution to each well. Incubate 5 to 10 minutes while shaking. Remove any bubbles. If necessary stop reaction with the addition of 100 µL of 0.2M HCl per well.

Read assay on Dynatech MR7000 ELISA reader. Test Filter: 410 nM; Reference Filter: 630 nM. A preferred template for the placement of controls in this experiment is shown above in Example 56.

5.61. Example 61

Kinase Inhibition of Selected Compounds

Using methods such as those described above, the ability of selected compounds of the invention to inhibit the activity of the kinases FlkGST, EGFR, PDGFR, cdk2SPA, and HER-2 are provided below:

| Compound Formula | bio FlkGST $IC_{50}$ (Mm) | bio EGFR $IC_{50}$ (µM) | bio PDGFR $IC_{50}$ (µM) | cdk2SPA $IC_{50}$ (µM) | HER-2 kinase $IC_{50}$ (µM) |
|---|---|---|---|---|---|
| 3 | 0.06 | 0.51 | >100 | >10 | 0.272 |
| 4 | 0.33 | 0.006 | >100 | >10 | 0.16 |
| 5 | >20 | >20 | >100 | | 61.16 |
| 6 | 3.31 | 0.001 | >100 | | 0.13 |
| 7 | 3.24 | 0.16 | 85.96 | | 0.04 |
| 8 | 15.93 | 0.06 | 16.39 | 2.62 | 0.1 |
| 9 | 16.49 | 0.04 | >100 | | 0.01 |
| 10 | >20 | >20 | >100 | | >100 |
| 11 | >20 | >20 | 28.14 | 0.01 | >100 |
| 12 | 0.78 | 0.004 | >100 | | 0.28 |
| 13 | >20 | 19.07 | >100 | | >100 |
| 14 | >20 | >20 | >100 | 0.04 | >100 |
| 15 | >20 | 0.02 | >100 | | 0.13 |
| 16 | 9.28 | 0.1 | >20 | | 1.02 |
| 17 | 16.22 | 0.02 | >20 | | 0.1 |
| 18 | 4.18 | 0.18 | 15.29 | | 0.03 |
| 19 | 1.05 | 0.17 | 12.75 | | |
| 24 | 2.73 | 0.89 | >20 | | |
| 25 | 5.12 | 0.058 | | | 11.92 |
| 26 | 15.16 | 0.16 | >20 | | |
| 27 | 5.3 | 0.15 | >20 | | 0.64 |
| 28 | 8.07 | 0.21 | >20 | | 0.16 |
| 29 | 14.88 | 0.45 | >20 | | |
| 30 | 13.87 | 0.77 | >20 | | |
| 31 | 19.42 | 0.21 | >20 | | 0.37 |
| 32 | 13.5 | 7.14 | >20 | | 18.74 |
| 33 | 18.68 | 0.9 | >20 | | |
| 34 | 14.73 | >20 | >20 | | >20 |
| 35 | >20 | 0.4 | >20 | | 0.59 |
| 36 | >20 | 17.39 | >20 | | >20 |
| 37 | 11.99 | 0.24 | >20 | | 1.07 |
| 38 | 5.98 | 5.6 | | | |

-continued

| Compound Formula | bio FlkGST IC$_{50}$ (Mm) | bio EGFR IC$_{50}$ ($\mu$M) | bio PDGFR IC$_{50}$ ($\mu$M) | cdk2SPA IC$_{50}$ ($\mu$M) | HER-2 kinase IC$_{50}$ ($\mu$M) |
|---|---|---|---|---|---|
| 39 | >20 | 0.004 | >20 | | |
| 40 | >20 | 4.2 | | | |
| 41 | >20 | 0.54 | >20 | | |
| 42 | 13.17 | 10.43 | | | |
| 43 | 13.09 | 0.86 | >20 | | |
| 44 | 13.76 | >20 | | | |
| 45 | 6.61 | 0.05 | >20 | | |
| 46 | 7.41 | 0.0012 | | | |
| 47 | 10.16 | 0.036 | >20 | | |
| 48 | >20 | >20 | | | |
| 49 | 17.25 | 0.005 | >20 | | 1.8 |
| 50 | 3.46 | 0.377 | | | |
| 51 | 7.15 | 0.038 | | | 0.86 |
| 52 | 1.62 | 0.0011 | | | |
| 53 | 4.68 | <0.156 | | | |
| 54 | >20 | <0.156 | | | |

From these data, it is readily apparent that preferred compounds of the invention are capable of inhibiting the activities of a variety of different kinases. It is further apparent that particular compounds are capable of exhibiting highly selective inhibition. For example, the hydrochloride salt of compound 6 (i.e., 5-[4-(1-benzyl-1H-indol-5-ylamino)-6-oxo-6,7-dihydro-pyrrolo[2,3-d]pyrimidin-5-ylidenemethyl]-4-methyl-1H-pyrrole-2-carboxylic acid (2-morpholin-4-yl-ethyl)-amide hydrochloride) inhibits EGFR at very low concentrations, yet exhibits relatively little effect on the activity of PDGFR.

5.62 Example 62

Oral Formulation

Hard gelatin capsule dosage forms containing kinase inhibitors of the invention can be prepared using the following ingredients:

| Component | 5 mg capsule | 10 mg capsule | 20 mg capsule |
|---|---|---|---|
| Kinase Inhibitor | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The kinase inhibitor is sieved and blended with the excipients listed. The mixture is filled into suitably sized two-piece hard gelatin capsules using suitable machinery and methods well known in the art. See, e.g., *Remington's Pharmaceutical Sciences*, 16th or 18th Editions, each incorporated herein in its entirety by reference. Other doses can be prepared by altering the fill weight and, if necessary, changing the capsule size to suit. Any of the stable, non-lactose hard gelatin capsule formulations above can be formed.

Compressed tablet dosage forms of kinase inhibitors can be prepared using the following ingredients:

| Component | 5 mg capsule | 10 mg capsule | 20 mg capsule |
|---|---|---|---|
| Kinase Inhibitor | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The kinase inhibitor is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths can be prepared by altering the ratio of the active ingredient to the excipient(s) or modifying the table weight.

The embodiments of the invention described above are intended to be merely exemplary, and those skilled in the art will recognize, or will be able to ascertain using no more than routine experimentation, numerous equivalents of the specific materials and procedures. All such equivalents are considered to be within the scope of the invention and are encompassed by the appended claims. All patents, patent applications and publications cited herein are incorporated by reference in their intirety.

What is claimed is:

1. A compound of Formula 1

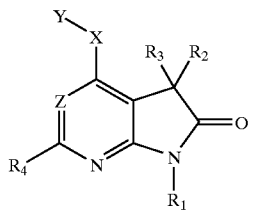

or a pharmaceutically acceptable salt or solvate thereof, wherein:

$R_1$ is H or methyl;

each of $R_2$ and $R_3$ is independently H, halogen, ($C_1$–$C_3$) alkyl, or ($C_1$–$C_3$)alkoxy; or $R_2$ and $R_3$ taken together form an optionally substituted methylindene selected from the group consisting of;

1a-1n:

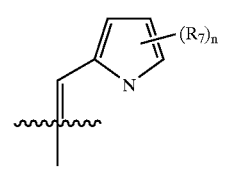

1a

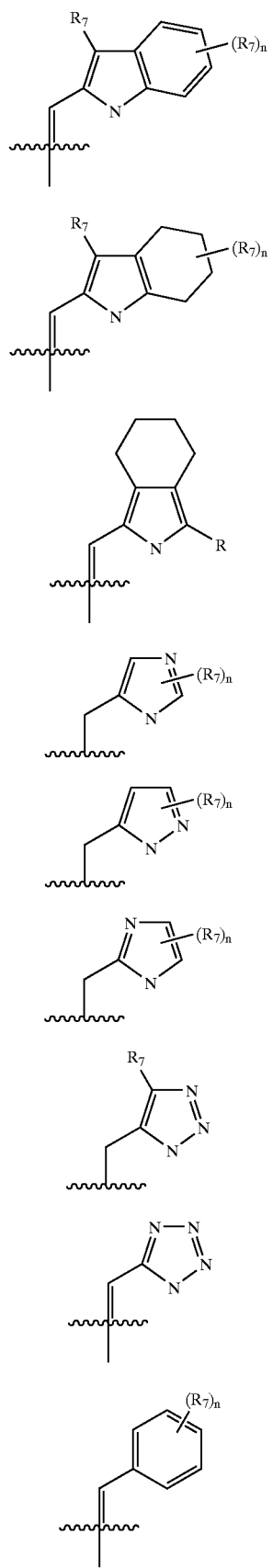

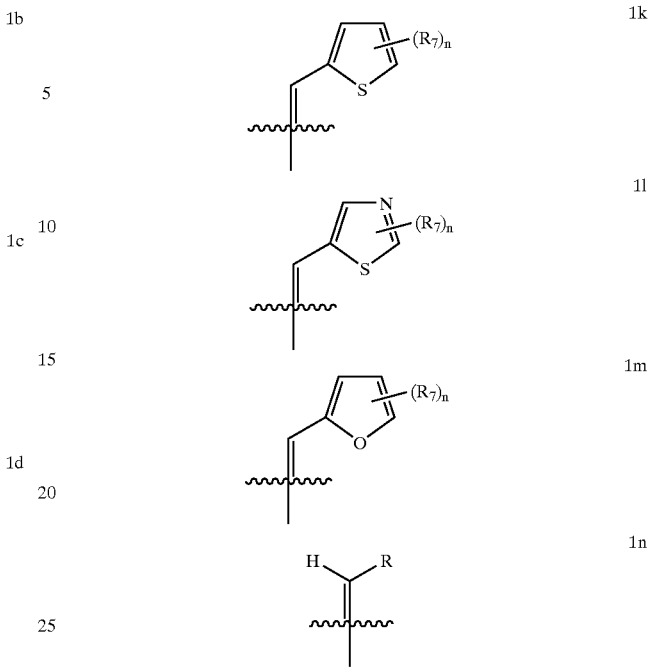

wherein:

n is an integer of 0–3;

each $R_7$ is independently H, alkyl, carboxylic acid, amine, halogen, nitro, cyano, $X_1$, $X_2$—$(C-C_4)$alkyl-$R_8$, $X_2$—$(C_1-C_4)$alkenyl-$R_8$, or $X_2$—$(C_1-C_4)$alkynyl-$R_8$;

$X_1$ is —C(O)NR$_9$—, —NR$_9$C(O)—, —C(O)O—, C(O)R$_{11}$, —OC(O)—, —O—, —NR$_9$—, —S—, —S(O$_2$), or —S(O$_2$)NR$_9$—;

$X_2$ is a chemical bond, —C(O)NR$_9$—, —NR$_9$C(O)—, —C(O)O—, C(O)R$_{11}$, —OC(O)—, —O—, —NR$_9$—, —S—, —S(O$_2$), or —S(O$_2$)NR$_9$—;

$R_8$ is selected from the group consisting of hydrogen, dialkylamino, carboxyl, hydoxyl, alkoxy, sulfonamide, urea, carbamate, diol, alkylsulphonyl, and $R_{10}$;

$R_9$ is H or (C$_1$–C$_3$)alkyl;

$R_{10}$ is an optionally substituted 5- or 6-membered saturated, unsaturated, or aromatic heterocycle comprising from 1 to 4 heteroatoms; and $R_{11}$ is an optionally substituted 5- to 6-membered saturated heterocyclic ring;

$R_4$ is H, methyl, trifluoromethyl, (C$_1$–C$_4$)alkyl, alkoxy, amido, amino, or optionally substituted aryl;

X is a chemical bond, ethynyl, —O—, —S—, —S(O)—, —S(O$_2$)—, —NR$_5$C(O)—, or —NR$_5$—, wherein $R_5$ is H, methyl, or substituted methylene;

Y is a 5- to 10-membered mono or bicyclic, saturated, unsaturated, or aromatic ring comprising 0–3 heteroatoms and optionally substituted; and Z is N or CR$_6$, wherein $R_6$ is H, halogen, nitro, cyano, alkoxyl, sulfonamide, amino, or amide.

2. The compound of claim 1 wherein X is a chemical bond, —O—, —S—, or —NR$_5$—.

3. The compound of claim 1 wherein Y is selected from the group consisting of phenyl, indolyl, indolinyl, 1H-indazolyl, 2,3-dihydro-1H-indazolyl, 1H-benzimidazolyl, 2,3-dihydro-1H-benzimidazolyl, benzotriazolyl, pyridyl, pyrimidyl, 4-substituted piperazin- 1-yl, morpholino, piperidinyl, pyrrolidin-1-yl, furanyl, thiophenyl, pyrrolyl, pyrazolyl, imidazolyl, pyridopyrrolyl, pyridazopyrrolyl, pyrimidopyrrolyl, pyrazopyrrolyl, and pyridofuranyl.

4. The compound of claim 1 wherein $R_2$ and $R_3$ are both H, halogen, or methyl.

5. The compound of claim 1 wherein $R_2$ and $R_3$ are taken together to form a ring selected from the group consisting of 1,3-dioxolane, 1,3-dioxane, cyclopropyl, cyclobutyl, cyclopentyl, and cyclohexyl.

6. The compound of claim 1 wherein $R_7$ is $X_2$—($C_1$-$C_4$)alkyl-$R_8$, $X_2$—($C_1$-$C_4$)alkenyl-$R_8$, or $X_2$—($C_1$-$C_4$)alkynyl-$R_8$, and $R_8$ is selected from the group consisting of alkylsulfonyl, alkoxy, carboxyl, morpholino, 1-alkyl-piperazin-4-yl, pyrrolidinyl, piperidinyl, pyridyl, imidazolo, triazolo, tetrazolo, and thiazolo.

7. The compound of claim 1 wherein $R_4$ is H, methyl, or trifluoromethyl.

8. The compound of claim 1 wherein $R_1$ is $CH_3$ or $R_3$ and $R_2$ do not form an optionally substituted methylindene.

9. A compound selected from the group consisting of:

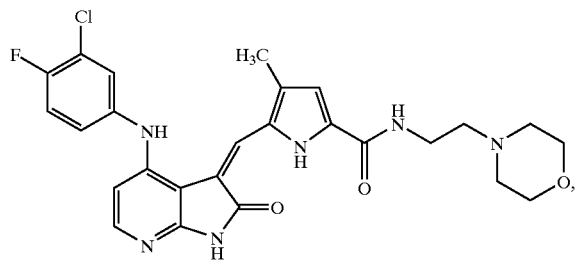

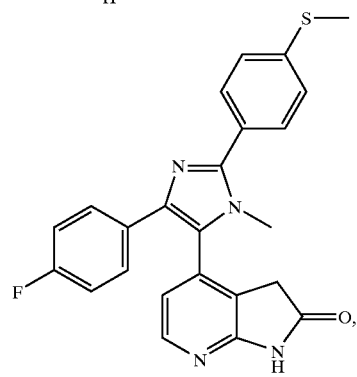

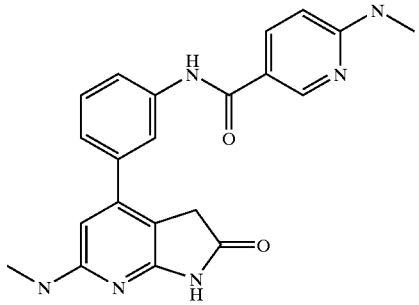

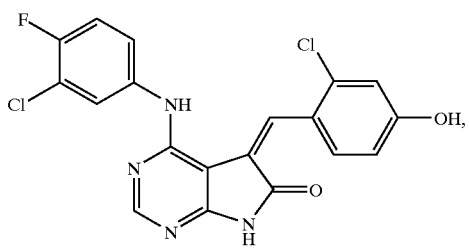

, and and pharmaceutically acceptable salts or solvates, thereof.

10. A pharmaceutical composition comprising a compound of claim 1, or a pharmaceutically acceptable salt or solvate, thereof, and a pharmaceutically acceptable carrier.

11. The pharmaceutical composition comprising a compound of claim 9 and a pharmaceutical acceptable carrier or excipient.

12. The pharmaceutical composition of claim 10 which is suitable for oral, transdermal, topical, parenteral, or mucosal administration.

* * * * *